US008461085B2

(12) United States Patent
Weston et al.

(10) Patent No.: US 8,461,085 B2
(45) Date of Patent: Jun. 11, 2013

(54) BIOHERBICIDE FROM *FESTUCA* SPP

(75) Inventors: Leslie A. Weston, Trumansburg, NY (US); Cecile Bertin, Montreal (CA); Frank Schroeder, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 1423 days.

(21) Appl. No.: 11/815,823

(22) PCT Filed: Feb. 8, 2006

(86) PCT No.: PCT/US2006/004431
§ 371 (c)(1),
(2), (4) Date: Nov. 28, 2007

(87) PCT Pub. No.: WO2006/086474
PCT Pub. Date: Aug. 17, 2006

(65) Prior Publication Data
US 2008/0261815 A1    Oct. 23, 2008

Related U.S. Application Data

(60) Provisional application No. 60/650,834, filed on Feb. 8, 2005.

(51) Int. Cl.
*A01N 37/10*    (2006.01)
*A01N 39/02*    (2006.01)

(52) U.S. Cl.
USPC .......................................... 504/314; 504/317

(58) Field of Classification Search
None
See application file for complete search history.

(56) References Cited

U.S. PATENT DOCUMENTS

| | | | |
|---|---|---|---|
| 4,002,459 | A | 1/1977 | Johnson et al. |
| 4,282,371 | A | 8/1981 | Rothgery |
| 5,395,951 | A | 3/1995 | Nagasampagi et al. |
| PP9,555 | P | 5/1996 | Morrison |
| 5,538,890 | A | 7/1996 | Sands et al. |
| 5,633,450 | A | 5/1997 | Suslow et al. |
| 5,939,359 | A | 8/1999 | Engel et al. |
| 5,985,648 | A | 11/1999 | Shamoun et al. |
| 6,020,288 | A | 2/2000 | Nonomura et al. |
| PP11,373 | P | 5/2000 | Riordan et al. |
| 6,107,279 | A | 8/2000 | Estruch et al. |
| 6,121,521 | A | 9/2000 | Desai |
| 2005/0043178 | A1 | 2/2005 | Vivanco et al. |

FOREIGN PATENT DOCUMENTS
WO    2005/077171 A1    8/2005

OTHER PUBLICATIONS

Fujii(The use of allelopathic chemicals in sustainable agriculture, Proceedings of the Plant Growth Regulator Society of America, 1995, 22nd, 31-38).*
Fujii(Allelopathy of velvetbean: determination and identification of L-Dopa as a candidate of allelopathic substances, Biologically Active Natural Products: Agrochemicals, [the Symposi um held at the 214th American Chemical Society National Meeting], Las Vegas, Nev., 1997(1999) Meeting Date 1997, 33-47).*
Fujii et al.,(Allelopathy of velvetbean: its discrimination and identification of L-Dopa as a candidate of allelopathic substances, JARQ, 1992, vol. 25 No. 4, 238-47).*
Fujii et al.(L-3,4-dihydroxyphenylalanine as an allelochemical candidate from *Mucuna pruriens*(L.) DC. Var. utilis, Agricultural and Biological Chemistry, 1991, vol. 55 No. 2, 617-18).*
International Search Report and Written Opinion for Corresponding International Application PCT/US06/04431 (mailed Oct. 24, 2006).
Netzly et al., "Roots of *Sorghum* Exude Hydrophobic Droplets Containing Biologically Active Components," Crop Sci. 26:775-778 (1986).
Bertin et al., "Are Fine Leaf Fescue Species Differentially Weed Suppressive?," Weed Science Society of America Annual Meeting, Feb. 9-12, 2003 (Jacksonville, FL).
Bertin et al., "Further Evaluation of Allelopathic Potential of Fine Leaf Fescue," 56th Annual Meeting of the Northeastern Weed Science Society, Jan. 7-10, 2002 (Philadelphia, PA).
Robinson et al., "Transformation of the Bioherbicide *Colletotrichum gloeosporioides* f. sp. *Aeschynomene* by Electroporation of Germinated Conidia," Curr. Genet. 36:98-104 (1999).
Gonzalez et al., "Inhibition of a Photosystem II Electron Transfer Reaction by the Natural Product Sorgoleone," J. Agric. Food Chem. 45:1415-1421 (1997).
Nimbal et al., "Herbicidal Activity and Site of Action of the Natural Product Sorgoleone," Pesticide Biochem. Physiol. 54:73-83 (1996).
Bertin et al., "Laboratory Assessment of the Allelopathic Effects of Fine Leaf Fescues," J. Chem. Ecol. 29 (8):1919-1937 (2003).
Rimando et al., "A New Photosystem II Electron Transfer Inhibitor from Sorghum bicolor," J. Nat. Prod. 61:927-930 (1998).
Alvarez-Morales et al., "Chemotaxis of *Azospirillum lipoferum* and *Azospirillum brasiliensis* Toward Root Exudates of Gramineae," Rev. Latin-amer Microbiol. 22(3):131-135 (1980).
Bertin et al., "Evaluation of Potential Allelopathic Effects of Fine Fescue (*Festuca rubra*) Accessions on Turf Weeds," Northeastern Weed Science Society Proceedings 55:33 (2001) (abstract only).

* cited by examiner

*Primary Examiner* — Alton Pryor
(74) *Attorney, Agent, or Firm* — LeClairRyan

(57) ABSTRACT

The present invention relates to methods of using m-tyrosine compounds from *Festuca* species for inhibiting weed growth and enhancing growth of non-weed plants. The present invention also relates to methods of identifying plants having herbicidal properties.

44 Claims, 27 Drawing Sheets

BIOHERBICIDE FROM *FESTUCA* SPP

This application claims the benefit of U.S. Provisional Patent Application Ser. No. 60/650,834, filed Feb. 8, 2005.

This invention was developed with Federal government funding under U.S. Department of Agriculture CSREES Hatch Grant No. NYC-14532. The U.S. Government may have certain rights in this invention.

FIELD OF THE INVENTION

The present invention relates to methods of using m-tyrosine compounds from *Festuca* spp. for inhibiting weed growth and enhancing growth of non-weed plants. The present invention also relates to methods of identifying plants having herbicidal properties.

BACKGROUND OF THE INVENTION

The presence of turfgrass in a landscape directly impacts the quality of human life from a visual, functional and recreational point of view. In the United States, there are currently greater than 12 million hectares of turfgrass including lawns, parks, golf courses, sod farms, industrial and institutional grounds, and highway right-of ways. In New York State alone, over 3.4 million hectares have been established in turfgrass. In all turf settings, especially lawn and roadside turf, weeds are a key pest problem. A substantial pesticide market (over two billion U.S. dollars) currently exists for control of weeds, insects, and diseases in private and commercial turfgrass settings in the United States. Although herbicides continue to be the predominant form of weed management in commercial turf settings, herbicide use in public and private landscapes is increasingly challenged by environmental and health concerns (Mortensen et al., "The Role of Ecology in the Development of Weed Management Systems: An Outlook," *Weed Res.* 40:49-62 (2000)). Consequently, turfgrass stakeholders, including homeowners and turf managers, are seeking alternative weed management tools (Matteson, P., "The '50% Pesticide Cuts' in Europe: a Glimpse of Our Future?," *Am. Entomol.* 41:210-220 (1995). One preventive strategy to minimize weed infestation is the use of appropriate turf mixtures or cultivars that are well adapted to a given setting. Weeds are much less likely to invade a well managed turf in optimal condition, maintained with appropriate cultural practices including timely mowing, fertilization, and irrigation (Bertin, "Alternate Weed Management Strategies for Landscape and Turf Settings," in Inderjit, Ed., *Weed Biology and Management*, Dordrecht/Boston/London: Kluwer Academic Publishers, pp. 403-422 (2004)).

Biological and organic approaches for weed management in turf have often not provided effective long-term control of turf weeds (Bertin, "Alternate Weed Management Strategies for Landscape and Turf Settings," in Inderjit, Ed., *Weed Biology and Management*, Dordrecht/Boston/London: Kluwer Academic Publishers, pp. 403-422 (2004)). Although plant pathogenic organisms have been evaluated for selective control of turf weeds, few, if any, commercial biocontrol products for weed management are currently available. Evaluation of organic products for weed management in turf has shown that most products do not provide selective, or cost-effective long-term weed suppression. Weed removal by mulching, cultivation, flame-burning, and steaming can be utilized in landscapes, but is cost prohibitive and sometimes injurious to turf (Bertin, "Alternate Weed Management Strategies for Landscape and Turf Settings," in Inderjit, Ed., *Weed Biology and Management*, Dordrecht/Boston/London: Kluwer Academic Publishers, pp. 403-422 (2004); Weston L. A., "Developing Natural Pest Control Products for Turf," *Cornell University Turfgrass Times* pp. 1-7 (1999)). Organic products such as acetic acid or clove oil-based products will result in significant turf injury. Corn gluten meal can provide some initial preemergent weed suppression but many studies have shown inconsistent control (Bertin, "Alternate Weed Management Strategies for Landscape and Turf Settings," in Inderjit, Ed., *Weed Biology and Management*, Dordrecht/Boston/London: Kluwer Academic Publishers, pp. 403-422 (2004)).

Weed management in turfgrass settings. Weed infestation often leads to lower crop yields in agriculture, less efficient land use, and poor crop quality (Ashton et al., "Weed Science Principles and Practices," Third Edition (1991)). In agronomic crops, specific problems caused by weedy plants constitute several billion dollars of annual yield loss in the United States alone. The green industry, including private and commercial landscape projects such as golf courses, parks, and athletic fields has experienced significant expansion over the last decade. In a typical city in the United States, 70% of the total turfgrass acreage consists of residential lawns (Cockerham et al., "The Size, Scope, and Importance of the Turfgrass Industry," in Gibeault et al., Eds., *Turfgrass Water Conservation*, University of California, Riverside: Division of Agriculture and Natural Resources, pp. 7-12 (1985)). In turfgrass settings, the traditional definition of a weed is often expanded to any plant that is unwanted because of its disruptive effect on the aesthetic appearance, stabilizing capacity, or overall utility of a turf (Turgeon, A. J., "Turfgrass Management," Upper Saddle River, N.J.: Charles Stewart, 356 p. (1996)). Uniformity is one of the key components of turfgrass quality. A different leaf width and/or shape, growth habit, or color will substantially disrupt the uniformity of a turf (Beard, J. B., "Turfgrass: Science and Culture," Englewood Cliffs, N.J.: Prentice Hall (1973)). In addition to detracting from aesthetic appearance and uniformity, weeds also compete with desirable turfgrass species for light, soil moisture and nutrients, and carbon dioxide (Beard, J. B., "Turfgrass: Science and Culture," Englewood Cliffs, N.J.: Prentice Hall (1973)).

Weed management in turfgrass settings is generally limited to those methods involving prevention of propagule dispersal and those limiting infestation including mechanical and chemical controls (Beard, J. B., "Turfgrass: Science and Culture," Englewood Cliffs, N.J.: Prentice Hall (1973)). Sanitary practices resulting in prevention of infestation include the use of weed free sod, soil and sand, equipment cleaning to remove propagules and mowing of weed-infested adjacent fields to prevent weed seed dispersal. Weed encroachment into an established turf is minimized when appropriate management practices create a dense, vigorous sward. Utilization of the proper turf species, mowing height and frequency, soil fertility and pH level, irrigation frequency and intensity, disease, insect and nematode controls, and aeration of compacted areas can result in a dense and vigorous turf. Mechanical weed control in turf, including removal of weeds either by hand or by spading, is a labor intensive control method, even though it can be effectively used for broadleaf weeds on relatively small turf areas (Beard, J. B., "Turfgrass: Science and Culture," Englewood Cliffs, N.J.: Prentice Hall (1973)).

Pest management in green settings can be intensive as zero tolerance for pests is often the case, with multiple applications of herbicides utilized to manage weeds. Concerns over the long-term effects of synthetic chemicals in agriculture and the green industry have led to research focused on the discovery of natural products for pest management and development of alternative pest management strategies based on biological control for landscape and turf settings (Bertin et al., "Alternate Weed Management Strategies for Landscape and Turf Settings," In derjit, in *Weed Biology and Management*, Inderjit, Ed., Dordrecht/Boston/London: Kulwer Academic Publishers, pp. 403-422 (2004); Cardellina, J. H., "Natural Products in the Search for New Agrochemicals," in Cutler., H. G., Ed., *Biologically Active Natural Products: Potential Use in Agriculture*, Washington, D.C.: American Chemical Society, pp. 305-315 (1988); Duke, S. O., "Weeding with Transgenes," *Trends Biotech.* 21:192-195 (2003)). Turf industry officials need to stay apprised of efforts to impose non-chemical or organic maintenance protocols as well as the science and regulations concerning pesticide use. The United States Golf Association (USGA) has invested $25 million in turfgrass and environmental research since 1983, much of which has focused on the development of turfgrass species requiring less pesticide, fertilizer, and water, and best management practices aimed at reducing risk to the environment. Chemical manufacturers have also continued to develop reduced-risk products for safer alternatives to many older pesticides. The development of alternative products and holistic management solutions presents some exciting opportunities and challenges for agricultural science researchers.

Alternative Weed Management Strategies. The use of pathogenic organisms to control weeds has not proven particularly effective due to problems in obtaining consistent control and difficulty in developing the appropriate mode of release for biocontrol organisms (Bertin et al., "Laboratory Assessment of the Allelopathic Effects of Fine Leaf Fescues," *J. Chem. Ecol.* 29:1919-1937 (2003)). Certain biological agents such as viruses, bacteria and fungi can selectively kill the target weed without injuring the turf. The likelihood of finding organisms with both the selectivity and the ability to be stored for long-term periods of time for use as commercial herbicides are small. One organism that has recently received great attention in the turf industry is *Xanthomonas campestris* pv. *poannua*. This bacterium selectively controls annual bluegrass (*Poa annua* L.), a serious weed in managed turfgrass stands, including golf courses. The main limitations of the formulated product containing the bacteria are its short shelf life and the fact that it appears to work better on annual biotypes of *Poa* than on the more abundant perennial types. Working with living organisms requires the development of specific techniques for successful application and control. Research has been conducted to scale up production of *X. campestris* as well as determination of appropriate storage conditions (Jackson et al., "Growth Requirements for Production of Stable Cells of the Bioherbicidal Bacterium *Xanthomonas campestris*," *J. Ind. Microb. Biotech.* 21:237-241 (1998)).

The use of natural products as bioherbicides for weed control is also receiving increased attention (Duke et al., "Chemicals From Nature for Weed Management," *Weed Sci.* 50:138-151 (2002); Duke et al., "Strategies for the Use of Natural Products for Weed Management," *J. Pesticide Sci.* 27:298-306 (2002)). In 1984, Rice, E. L., "Allelopathy," Orlando: Academic Press, xi, 422 p. (1984) suggested that the use of plant-derived compounds as natural herbicides is an environmentally-sound option for weed management. Recently, corn or wheat gluten meal has been studied for use as a preemergent bioherbicide for turf and landscape settings (Bingamen et al., "Greenhouse Screening of Corn Gluten Meal as a Natural Control Product for Broadleaf and Grassy Weeds," *Hort. Sci.* 30:1256-1259 (1995); Gough et al., "Wheat Gluten Meal Inhibits Germination and Growth of Broadleaf and Grassy Weeds," *HortSci.* 34:269-270 (1999); Unruh et al., "Herbicidal Effects of the Dipeptide Alanyl-Alanine on Perennial Ryegrass (*Lolium perenne* L.) Seedlings," *Crop Sci.* 37:208-211 (1997)).

Corn gluten meal contains 10% nitrogen by weight, a relatively high percentage of available nitrogen. It is a pre-emergent material only and has no post-emergent effects on weeds that are already established. Corn gluten meal could be considered as a natural weed-and-feed material for turf, as it purportedly inhibits the establishment of germinating weeds while acting as a fertilizer. Radicle damage in germinating weed seed appears to be localized to the meristematic region resulting in inhibition of root elongation. Among the weeds reportedly controlled with pre-emergent applications of the product are crabgrass (*Digitaria* sp.), dandelion (*Taraxacum officinale* W.), smartweed (*Polygonum* sp.), redroot pigweed (*Amaranthus retroflexus* L), purslane (*Portulaca oleracea* L), lambsquarters (*Chenopodium album* L), foxtail (*Setaria* sp.), and barnyardgrass (*Echinochloa crus-galli* (L.) Beauv) (Gough et al., "Wheat Gluten Meal Inhibits Germination and Growth of Broadleaf and Grassy Weeds," *HortSci.* 34:269-270 (1999)). Both powder and pelleted formulations are available.

In turf situations, corn gluten meal is often applied at 20 lb/1000 square feet (Gough et al., "Wheat Gluten Meal Inhibits Germination and Growth of Broadleaf and Grassy Weeds," *HortSci.* 34:269-270 (1999)). Potential problems with corn gluten meal can arise, depending on the availability of soil moisture and microbial activity, both of which reduce product efficacy. The other drawback is the higher cost of corn gluten meal as compared to other standard fertilizers and weed and feed products. The generally low specific activity of the active ingredients associated with corn gluten meal including alaninyl-alanine, a dipepetide isolated from corn gluten meal, may also lead to inconsistent results in field applications. Sensitive species purportedly exhibit damage to cellular membranes, altered cell nuclei and mitotic structures, and an overall loss of cytoplasmic integrity. Treated root tips were reported to exhibit extreme cell wall abnormalities including uneven thickening and breakage, especially in the epidermal and subepidermal cells (Unruh et al., "Mitotic and Ultrastructure Changes in Root Merestems of Grass Seedlings Treated with Alaninyl-Alanine," *Crop Sci.* 37:1870-1874 (1997)).

The present invention is directed to overcoming these and other deficiencies in the art.

SUMMARY OF THE INVENTION

The present invention relates to a method of inhibiting weed growth. This method involves providing an m-tyrosine compound having a formula of Formula I or a salt of the m-tyrosine compound of Formula I:

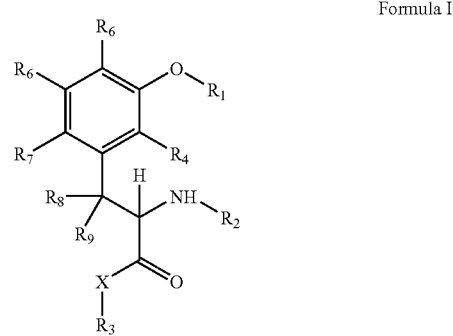

Formula I where:

R₁ and R₂ are independently selected from the group consisting of H, sulfonate, sulfonamide, phosphonate, alkyl, alkenyl, alkynyl, alkoxy, alkoxycarbonyl, saccharide, cycloalkyl, heterocycloalkyl, aryl, and heteroaryl, wherein each of phosphonate, alkyl, alkenyl, alkynyl, alkoxy, alkoxycarbonyl, saccharide, cycloalkyl, heterocycloalkyl, aryl, and heteroaryl is either substituted or unsubstituted;

R₃ is selected from the group consisting of H, alkyl, alkenyl, alkynyl, alkoxy, alkoxycarbonyl, saccharide, cycloalkyl, heterocycloalkyl, aryl, and heteroaryl, wherein each of alkyl, alkenyl, alkynyl, alkoxy, alkoxycarbonyl, saccharide, cycloalkyl, heterocycloalkyl, aryl, and heteroaryl is either substituted or unsubstituted;

X is selected from the group consisting of O and N—Y, wherein Y is selected from the group consisting of H, alkyl, alkenyl, alkynyl, alkoxy, alkoxycarbonyl, saccharide, cycloalkyl, heterocycloalkyl, aryl, and heteroaryl, wherein each of alkyl, alkenyl, alkynyl, alkoxy, alkoxycarbonyl, saccharide, cycloalkyl, heterocycloalkyl, aryl, and heteroaryl is either substituted or unsubstituted;

R₄, R₅, R₆, and R₇ are independently selected from the group consisting of H, hydroxyl, halogen, amino, and nitro; and R₈ and R₉ are independently selected from the group consisting of H, hydroxyl, halogen, amino, methyl, and halogenated methyl.

The method also involves treating a weed or weed seed with the m-tyrosine compound of Formula I or the salt of the m-tyrosine compound of Formula I under conditions effective to inhibit growth of the weed or weed seed in a growth medium.

The present invention also relates to a method of enhancing growth of a non-weed plant by inhibiting growth of weeds that are located proximate to the non-weed plant. This method involves providing an m-tyrosine compound of Formula I or a salt of the m-tyrosine compound of Formula I. This method also involves treating a weed or weed seed with the m-tyrosine compound of Formula I or the salt of the m-tyrosine compound of Formula I under conditions effective to inhibit growth of said weed or weed seed in a growth medium, thereby enhancing growth of non-weed plants growing in said growth medium.

Given the increasing public concern related to the use of synthetic herbicides, the need for new biorational methods for weed management is great. As disclosed herein, the identification of m-tyrosine as a naturally produced phytotoxin could contribute to the development of unique, effective, and environmentally acceptable means of weed control (Bertin et al., "The Role of Root Exudates and Allelochemicals in the Rhyzosphere," *Plant and Soil* 256:67-83 (2003), Bertin et al., "Laboratory Assessment of the Allelopathic Effects of Fine Leaf Fescues," *J. Chem. Ecol.* 29:1919-1937 (2003), Cardellina, J. H., "Natural Products in the Search for New Agrochemicals" in Cutler, H. G., Ed. *Biologically Active Natural Products: Potential Use in Agriculture*, Washington, D.C.: American Chemical Society, pp. 305-315 (1988), Duke et al., "United States Department of Agriculture-Agricultural Research Service Research on Natural Products for Pest Management" *Pest Man. Sci.* 59:708-717 (2003), which are hereby incorporated by reference in their entirety).

BRIEF DESCRIPTION OF THE DRAWINGS

FIGS. 7A and 7C: Root tip cells. FIG. 7B: Root cap cells.

DETAILED DESCRIPTION OF THE INVENTION

Figure 1:
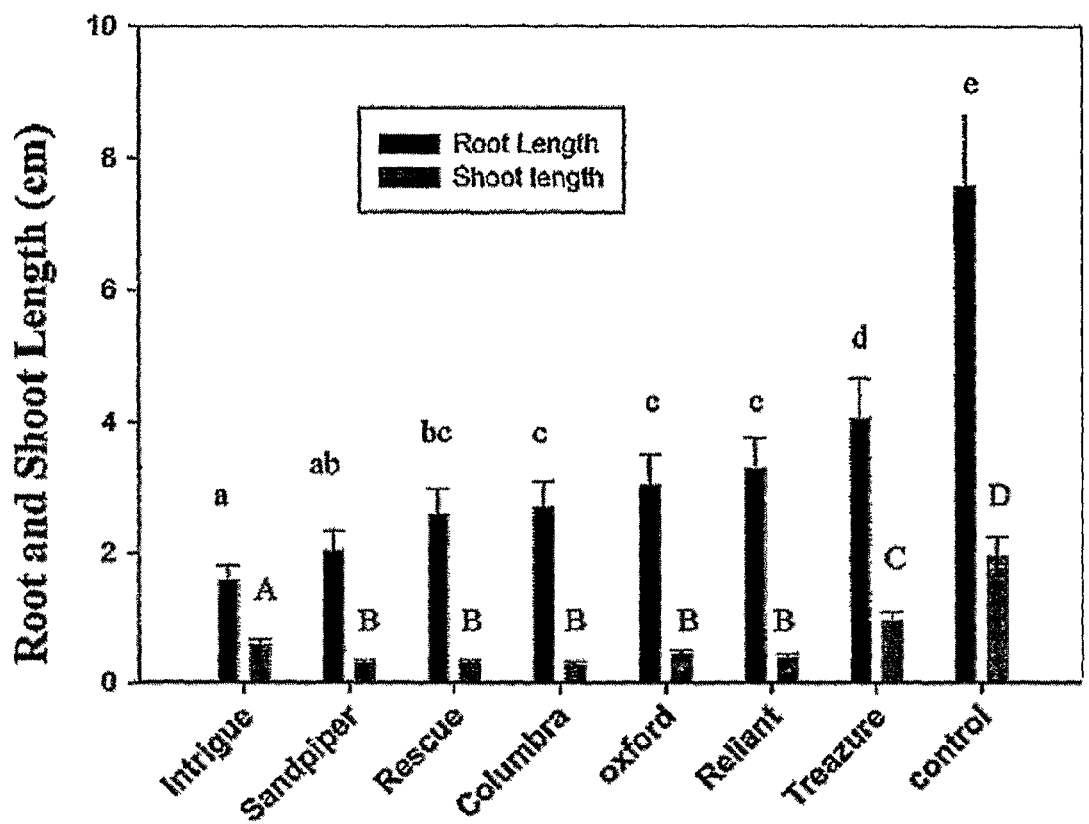
FIG. 1 shows inhibition of seedling growth of *Digitaria sanguinalis* L. by the presence of fine leaf fescue seedlings after 2 weeks of establishment in an agar medium. Bar represents § one standard error unit. N D 90. Values with the same letter are not significantly different with Fisher's protected LSD test at the 0.05 level.

The present invention relates to a method of inhibiting weed growth. This method involves providing an m-tyrosine compound having a formula of Formula I or a salt of the m-tyrosine compound of Formula I:

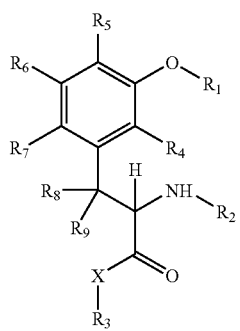

Formula I where:

$R_1$ and $R_2$ are independently selected from the group consisting of H, sulfonate, sulfonamide, phosphonate, alkyl, alkenyl, alkynyl, alkoxy, alkoxycarbonyl, saccharide, cycloalkyl, heterocycloalkyl, aryl, and heteroaryl, wherein each of phosphonate, alkyl, alkenyl, alkynyl, alkoxy, alkoxycarbonyl, saccharide, cycloalkyl, heterocycloalkyl, aryl, and heteroaryl is either substituted or unsubstituted;

$R_3$ is selected from the group consisting of H, alkyl, alkenyl, alkynyl, alkoxy, alkoxycarbonyl, saccharide, cycloalkyl, heterocycloalkyl, aryl, and heteroaryl, wherein each of alkyl, alkenyl, alkynyl, alkoxy, alkoxycarbonyl, saccharide, cycloalkyl, heterocycloalkyl, aryl, and heteroaryl is either substituted or unsubstituted;

X is selected from the group consisting of O and N—Y, wherein Y is selected from the group consisting of H, alkyl, alkenyl, alkynyl, alkoxy, alkoxycarbonyl, saccharide, cycloalkyl, heterocycloalkyl, aryl, and heteroaryl, wherein each of alkyl, alkenyl, alkynyl, alkoxy, alkoxycarbonyl, saccharide, cycloalkyl, heterocycloalkyl, aryl, and heteroaryl is either substituted or unsubstituted;

$R_4$, $R_5$, $R_6$, and $R_7$ are independently selected from the group consisting of H, hydroxyl, halogen, amino, and nitro; and $R_8$ and $R_9$ are independently selected from the group consisting of H, hydroxyl, halogen, amino, methyl, and halogenated methyl.

In one embodiment, the m-tyrosine compound of the present invention is a compound of Formula I, where:

$R_4$, $R_5$, $R_6$, $R_7$, $R_8$, and $R_9$ are H;

$R_1$ and $R_2$ are independently selected from the group consisting of H, sulfonate, sulfonamide, phosphonate, alkyl, alkenyl, alkynyl, alkoxy, alkoxycarbonyl, saccharide, cycloalkyl, heterocycloalkyl, aryl, aryloxycarbonyl, or heteroaryl, where each of phosphonate, alkyl, alkenyl, alkynyl, alkoxy, alkoxycarbonyl, saccharide, cycloalkyl, heterocycloalkyl, aryl, and heteroaryl is either substituted or unsubstituted;

$R_3$ is selected from the group consisting of H, alkyl, alkenyl, alkynyl, alkoxy, alkoxycarbonyl, saccharide, cycloalkyl, heterocycloalkyl, aryl, or heteroaryl, where each of alkyl, alkenyl, alkynyl, alkoxy, alkoxycarbonyl, saccharide, cycloalkyl, heterocycloalkyl, aryl, or heteroaryl is either substituted or unsubstituted; and X is selected from the group consisting of O and N—Y, where Y is selected from the group consisting of H, alkyl, alkenyl, alkynyl, alkoxy, alkoxycarbonyl, saccharide, cycloalkyl, heterocycloalkyl, aryl, or heteroaryl, where each of alkyl, alkenyl, alkynyl, alkoxy, alkoxycarbonyl, saccharide, cycloalkyl, heterocycloalkyl, aryl, or heteroaryl is either substituted or unsubstituted.

As described herein, the m-tyrosine compounds of the present invention can also be present in the form of their agriculturally useful salts, where the type of salt is generally unimportant. Suitable salts can include those of bases that do not adversely affect the herbicidal action of the m-tyrosine compounds used in the methods of the present invention. Particularly suitable basic salts are those of the alkali metals, preferably the sodium and potassium salts, those of the alkaline earth metals, preferably calcium, magnesium and barium salts, and those of the transition metals, particularly manganese, copper, zinc and iron salts, and the ammonium salts which may carry from one to three $C_1$-$C_4$-alkyl substituents, hydroxy $C_1$-$C_4$-alkyl substituents, and/or a phenyl or benzyl substituent, particularly diisopropylammonium, tetramethylammonium, tetrabutylammonium, trimethylbenzylammonium, and trimethyl(2-hydroxyethyl)ammonium salts, the phosphonium salts, the sulfonium salts, preferably tri-$C_1$-$C_4$-alkylsulfonium salts, and the sulfoxonium salts, particularly tri-$C_1$-$C_4$-alkylsulfoxonium salts.

Suitable ways for providing the m-tyrosine compound of the present invention can include isolating the m-tyrosine compound from a plant that produces the m-tyrosine compound. Another suitable way for providing the m-tyrosine compound is collecting living and/or dead tissue from plants that produce the m-tyrosine compound. Suitable plants from which the m-tyrosine compound of the present invention can be isolated include those that exude m-tyrosine from their tissues, particularly from their roots. Particular examples of such suitable m-tyrosine-producing plants include, but are not limited to, *Festuca* species, particularly *Festuca rubra* and subspecies thereof (e.g., *Festuca rubra rubra* L.) and *Festuca arizonensis* L., as well as *Euphorbia myrsinitis*. The procedures for isolating the m-tyrosine compound from the plants that produce and/or exude (e.g., from their roots) are disclosed herein, particularly in the examples set forth herein below.

Another suitable way for providing the m-tyrosine compound is by obtaining it from commercial suppliers of m-tyrosine (e.g., from Sigma-Aldrich, St. Louis, Mo.). The m-tyrosine compound used in the methods of the present invention can be in isolated form. Further, precursors of m-tyrosine can be used to synthesize m-tyrosine. The salts of the m-tyrosine compound can be prepared using standard methods well known in the art.

The method also involves treating a weed or weed seed with the m-tyrosine compound of Formula I or the salt of the m-tyrosine compound of Formula I under conditions effective to inhibit growth of the weed or weed seed in a growth medium.

The present invention also relates to a method of enhancing growth of a non-weed plant by inhibiting growth of weeds that are located proximate to the non-weed plant. This method involves providing an nm-tyrosine compound of Formula I or a salt of the m-tyrosine compound of Formula I. This method also involves treating a weed or weed seed with the m-tyrosine compound of Formula I or the salt of the m-tyrosine compound of Formula I under conditions effective to inhibit growth of said weed or weed seed in a growth medium, thereby enhancing growth of non-weed plants growing in said growth medium.

As used herein, the term "growth medium" refers to any medium that can be used to support growth of a plant, and can include, without limitation, various types of soils or plant nutrient media. Suitable examples of soils include, without limitation, natural soil and artificial soil.

In one aspect of the present invention, treating the weed or weed seed can involve applying the m-tyrosine compound of Formula I or the salt thereof to the surface of the growth medium. This can be done either prior to or after emergence of the weed from the growth medium. The m-tyrosine compound is added in an amount sufficient to inhibit growth of the weed or weed seed.

In one embodiment, the m-tyrosine compound or salt thereof can be applied at a level of between about 0.5 to about 12.0 pounds per acre, particularly between about 2.5 to 10.0 pounds per acre, more particularly between about 4.5 to 8.0 pounds per acres. The m-tyrosine compound or salt thereof can be applied to the growth medium and/or to the tissue of the weed. As used herein, the term "tissue" (in referring to a plant) can include, without limitation, roots, shoots, seeds, foliage, and portions of the roots, shoots, seeds, and foliage of the plant. The amount of m-tyrosine to be added to the growth medium or tissue of the weed can be adjusted in accordance with the ordinary practices in the relevant art of weed control.

The m-tyrosine compound or salt thereof can be applied to the growth medium, weed, or weed seed in various suitable forms, including, without limitation, granular form, liquid form, and/or spray/mist form. Applying the m-tyrosine compound or salt thereof to the foliage tissue of the weed can be carried out by spraying the foliage with the m-tyrosine compound or salt thereof. Another suitable approach to treating the weed or weed seed with the m-tyrosine compound or salt thereof can (but need not) involve infiltration of the m-tyrosine compound or salt thereof into the plant. Suitable application methods can include high or low pressure spraying, injection, and leaf abrasion proximate to when application of the m-tyrosine compound or salt thereof takes place. When treating weed seeds or propagules (e.g., cuttings), in accordance with the application embodiment of the present invention, the m-tyrosine compound or salt thereof, in accordance with present invention, can be applied by low or high pressure spraying, coating, immersion, or injection. The m-tyrosine compound or salt thereof can also be applied using other suitable application procedures of the m-tyrosine compound or salt thereof can be envisioned by those skilled in the art, provided these procedures are able to effect contact of the m-tyrosine compound or salt thereof to the weed or weed seed.

In another embodiment, treating can involve simultaneously applying the m-tyrosine compound or salt thereof to the growth medium surface and to foliage of the weed in an amount sufficient to inhibit growth of the weed and/or weed seed.

In yet another embodiment, treating the growth medium, the weed, and/or the weed seed with the m-tyrosine compound (or salt thereof) can involve using living and/or dead plant tissue containing the m-tyrosine compound. This plant tissue can be processed in a manner such that the m-tyrosine compound is released into the growth medium and/or contacted with the weed or weed seed to effect inhibition of growth of weeds or weed seeds contained in the growth medium. Suitable ways of processing the plant tissue can involve cutting, macerating, grinding, and/or powdering the plant tissue. Suitable plant tissue that can be used are those parts of the plant that contain or produce the m-tyrosine compound of the present invention, particularly the roots, leaves, and stems of the plants that contain the m-tyrosine compound.

Suitable weeds (and weed seeds) whose growth can be inhibited by the methods of the present invention can include monocot weeds (e.g., grass weeds) and dicot weeds (e.g., broadleaf weeds). Suitable grass weeds whose growth can be inhibited by the methods of the present invention can include, without limitation, crabgrass (*Digitaria sanguinalis*), barnyardgrass (*Echinochloa crus-galli*), annual bluegrass (*Poa annua*), and the like. Suitable broadleaf weeds whose growth can be inhibited by the methods of the present invention can include, without limitation, dandelion (*Taraxacum officinales*), white clover (*Trifolium repens*), black medic (*Medicago lupulina*), lettuce (*Lactuca sativa*), birdsfoot trefoil (*Lotus corniculatus*), common chickweed (*Stellaria media*), common purslane (*Portulaca oleraceae*), curly cress (*Lepidium sativum*), and the like.

In one aspect of the present invention's methods of inhibiting weed growth and enhancing growth of non-weed plants, the m-tyrosine compound or salt thereof can be admixed with water, soil, fertilizers, and/or any other appropriate carriers. Suitable admixtures and formulations can be envisioned by those skilled in the art, provided these admixtures and formulations support conditions that are effective to inhibit weed or weed seed growth in a growth medium. Suitable carriers can included water, aqueous solutions, slurries, and/or dry powders. Although not required, the m-tyrosine compound or salt thereof may be applied to the growth medium, weed, and/or weed seed along with additional additives, including fertilizer, insecticide, fungicide, nematacide, and mixtures thereof.

Suitable fertilizers include ammonium nitrate ($(NH_4)_2NO_3$). An example of a suitable insecticide is Malathion. Useful fungicides include Captan. Other suitable additives include buffering agents, wetting agents, coating agents, and abrading agents. These materials can be used to facilitate the methods of inhibiting weed growth or enhancing non-weed plant growth of the present invention. In addition, the m-tyrosine compound or salt thereof can be applied to plant seeds with other conventional seed formulation and treatment materials, including clays and polysaccharides.

The present invention can be used to enhance the growth of various non-weed plants, including, without limitation, turf grasses, crop plants, and ornamental plants. Suitable turf grasses whose growth can be enhanced by the method of the present invention can include, without limitation, fine fescue, tall fescue, Kentucky bluegrass, Bermudagrass, bentgrass, annual ryegrass, perennial ryegrass, and the like. Suitable crop plants whose growth can be enhanced by the method of the present invention can include, without limitation, alfalfa, rice, wheat, barley, rye, cotton, sunflower, peanut, corn, potato, sweet potato, bean, pea, chicory, lettuce, endive, cabbage, brussel sprouts, beet, parsnip, cauliflower, broccoli, turnip, radish, spinach, onion, garlic, eggplant, pepper, celery, carrot, squash, pumpkin, zucchini, cucumber, apple, cherry, peach, pear, melon, citrus, strawberry, grape, raspberry, pineapple, soybean, tobacco, tomato, sorghum, sugarcane, and the like. Suitable ornamental plants whose growth can be enhanced by the method of the present invention can include, without limitation, annual bedding plants, perennial bedding plants, herbaceous ornamental plants, woody ornamental plants, and the like.

The present invention also relates to a method of identifying a plant having bioherbicidal properties. This method involves providing a target plant or a portion of the target plant. The target plant or portion of the target plant is assayed for the presence of an m-tyrosine compound. Target plants testing positive for the presence of the m-tyrosine compound are identified as having bioherbicidal properties. Suitable portions of the target plants that can be assayed for the presence of the m-tyrosine compound can include, without limitation, root tissue, leaf tissue, shoot tissue, and foliage tissue. Suitable target plants can include, without limitation, *Festuca* species, particularly *Festuca rubra* or a subspecies thereof. Suitable procedures for assaying for the presence of the m-tyrosine compound can include, without limitation, the use of high performance liquid chromatography. Particular protocols for the assaying step are described in more detail herein below in the examples.

EXAMPLES

Example 1

Laboratory Assessment of the Allelopathic Effects of Fine Leaf Fescues

As described in Examples 2-14 (herein), laboratory screening studies were conducted to evaluate the allelopathic potential of fine leaf fescues. Of the seven accessions selected from prior field evaluations for weed-suppressive ability, all inhibited root growth of large crabgrass and curly cress in laboratory assays. Grown in agar as a growth medium and in the presence of living fescue seedlings for 14 or 21 days, test species were sensitive depending on the fescue cultivars. Growth inhibition increased when fescue was grown for increasing periods of time in agar. Seedling fescues produced significant quantities of bioactive root exudates, which were released into the agar medium. Bioactive root exudates were extracted from living fescue roots by using methylene chloride. Shoot tissue was extracted in water and the aqueous extract was partitioned against hexane, ethyl acetate, and methylene chloride. Extracts were tested for inhibitory activity on seedling growth as measured by inhibition of curly cress germination and radicle elongation. Root exudates were more toxic (70% inhibition) than shoot extracts (up 40% inhibition), when formulated at 0.25 mg/ml concentration. Light microscopy and transmission electron microscopy were utilized in an attempt to identify the cellular location of production of secondary products contained in bioactive root exudates. Ultrastructural analysis indicated that the exudate is produced in actively dividing tips of fibrous root cells.

Example 2

Plant Materials and Screening for Allelopathic Potential of Living Fescue Root Exudates Of the 78 fine leaf fescue cultivars evaluated in previous field studies (Bertin et al., "Further Evaluation of the Allelopathic Potential of Fine Leaf Fescue," *Proc WSSA* 56:116 (2002), which is hereby incorporated by reference in its entirety), 7 were selected for further laboratory evaluation. These included Oxford (hard fescue), Reliant II (hard fescue), Rescue 911 (hard fescue), Sandpiper (chewings fescue), Intrigue (chewings fescue), Columbra (chewings fescue), and Treazure (chewings fescue) (Table 1).

TABLE 1

FINE LEAF FESCUE CULTIVARS SELECTED FOR FURTHER LABORATORY EVALUATION

| Cultivar name | Fescue type | Species | Weed-suppressive activity[a] |
|---|---|---|---|
| Oxford | Hard fescue | *Festuca longifolia* L. Thuill | High |
| Reliant II | Hard fescue | *Festuca longifolia* L. Thuill | Moderate |
| Rescue 911 | Hard fescue | *Festuca longifolia* L. Thuill | Moderate |
| Sandpiper | Chewings fescue | *Festuca rubra* L. Subsp. *Commutata* Gaud. | High |
| Intrigue | Chewings fescue | *Festuca rubra* L. Subsp. *Commutata* Gaud. | High |
| Treazure | Chewings fescue | *Festuca rubra* L. Subsp. *Commutata* Gaud. | Moderate |
| Columbra | Chewings fescue | *Festuca rubra* L. Subsp. *Commutata* Gaud. | Moderate |

[a]Weed-suppressive activity refers to levels of weed suppression visually evaluated once a mouth during the growing in replicated field trials from 1999 to 2000 in Ithaca, New York.

Prior to each experiment, seeds of fine leaf fescue and indicator species (large crabgrass and cress (*Lepidium sativum* L.)) were surface-sterilized in a 20% (v/v) solution of sodium hypochlorite for 1 minute, repeatedly rinsed in distilled water, dried, and stored under sterile conditions at ambient temperature (20±C).

Under sterile conditions, 0.8% water agar (80 ml) was poured into plastic Magenta tissue culture boxes. Thirty sterilized fine leaf fescue seeds of each cultivar selected were seeded randomly on to the surface of the agar medium in individual boxes, which were then sealed. Control boxes contained 0.8% agar, but no fescue seedlings. All boxes were placed under artificial lighting with a 16-hr light (200 $^1$mol/m2/sec1) and 8-hr dark cycle at 20§5±C. After 7 days, 10 large crabgrass or cress seeds were randomly placed within the fine leaf fescue seedlings, and the box was resealed and placed under light (as previously described) for an additional period of 7 days. Experiments were arranged as completely randomized designs, with three replicates of each treatment. Percentage of germination of crabgrass and cress was recorded as well as root and shoot lengths of individual crabgrass and cress seedlings after 7 days. Experiments were repeated three times using identical methodology.

An additional bioassay to assess the allelopathic potential of fine leaf fescue over time was designed using the methodology previously described. However, after letting the fine leaf fescue seedlings establish for 7 days, fescue seedlings were removed, and 10 curly cress (*Lepidium sativum* L.) seeds were placed randomly in the zone where fescue seedlings previously had been positioned. The box was resealed and placed under a 16-hr light and 8-hr dark cycle for 7 days. The control treatment contained no fescue seedlings, so none were removed. Treatments (fescue once present vs. fescue never present) were replicated three times, and the experiment was arranged as a randomized complete block design. Root and shoot lengths of individual cress seedlings, as well as their percentage seed germination, were recorded after 7 days. The experiment was repeated over time on three separate occasions.

Example 3

Root Exudate Collection Under Stressed and Nonstressed Conditions

Approximately 100 g of fine leaf fescue seed of each cultivar was surface-sterilized to reduce microbial contamination and then placed on to each of six screens of a capillary mat system used for seedling generation of large quantities of living root tissue (Czarnota. M. A., "*Sorghum* (*Sorghum* spp.) Root Exudates, Production, Localization, Chemical Composition, and Mode of Action," in *Floriculture and Ornemantal Horticulture*, Ithaca, N.Y.: Cornell University, pp. 105 (2001), which is hereby incorporated by reference in its entirety). Seeds were allowed to germinate on the capillary mat system, and after 14 days, living roots were harvested by removal from the adjacent screen with a razor blade. Large quantities of healthy root tissue were harvested from each individual screen, and fresh weight was recorded. Collected root tissue was then dipped in 250 ml of methylene chloride for approximately 1 min. Roots were removed by filtration, and the methylene chloride extract, yellowish in color, was further filtered using a glass syringe fitted with a Gelman Acrodisc CR-PTFE $0.2\text{-}^1\text{m}$ filter. The extract was evaporated to dryness using a rotary evaporator at ambient temperature. Dry weight of the methylene chloride extract was obtained separately for each of the six screen replicates for each cultivar studied. Samples were then subjected to chemical analysis and bioassayed to assess inhibitory activity on the seed germination of cress species. Root exudates were also collected for each of the seven cultivars evaluated when seedling roots were propagated under stress-simulated conditions. To stimulate drought stress, using a capillary mat system as described previously, water was available as normal for 7 days to allow sufficient germination. In contrast to standard moisture conditions utilized in the first experiment from day 0 to 14, water stress conditions were applied to young fescue seedlings from day 7 to 14 in the second experiment by limiting the water supply at day 7, and thus drying the capillary mat progressively from day 7 through 14. This condition will be referred to as the dry growth conditions. The experiment was arranged as a completely randomized block and repeated three times.

Example 4

Influence of Fine Fescue Root Exudates on Cress Growth

Experiments were designed to assess the toxicity of collected root exudates by using the cultivars Intrigue and Sandpiper because of their differential weed-suppressive activity in the field. Concentrations ranged from 0 to 1 mg/ml and also included 0.0625, 0.125, 0.25, and 0.5 mg/ml. Glass petri dishes were lined with filter paper (Whatman #1), and 0.5 ml of each root exudate was dissolved in methylene chloride and added to the 5.5-cm filter paper, and methylene chloride was allowed to evaporate. After evaporation, 1 ml of distilled water and 10 cress seeds were placed into each dish. Petri dishes were maintained in an incubator for 72 hr at $26\pm C$ with relative humidity near saturation. Three replicates of each treatment were arranged in a completely randomized design. After 3 days, seedling root lengths were recorded. The control consisted of 0.5 ml of methylene chloride placed onto a filter paper, allowed to evaporate, and moistened with 1 ml of distilled water. Percentage inhibition of cress was expressed as a percentage decrease in radicle elongation in comparison to the control. Experiments were repeated on three separate occasions.

Example 5

Influence of Fine Leaf Fescue Shoot Extracts on Cress Growth

Fine leaf fescue, cultivar Intrigue, was grown in a greenhouse under natural light conditions during the late summer of 2000. When shoots were 6 weeks old, they were harvested by trimming and placed into a drying oven at $35\text{-}40\pm C$ for 4 days. Dried tissue was then ground in a Wiley mill. After grinding, powdered shoot tissue (100 mg) was extracted for 24 hr with 3-1 distilled water on a shaker in a $4\pm C$ cold room. After 24 hr, the mixture was filtered through four layers of cheesecloth to remove coarse particulates. Extracts were filtered through #4-, #1-, and #42-grade filter paper (Whatman) by using a Buchner funnel. The clear extract was partitioned using a solvent series that included hexane, methylene chloride, and ethyl acetate. Extractions were performed three times for each solvent with 100 ml of solvent in a separatory funnel. Extracts were combined for each solvent and dried using rotoevaporation at ambient room temperature. Toxicity of leaf extracts was evaluated as percentage decrease in root elongation compared to the control. Extracts were evaluated over a range of concentrations (0.0125-0.5 mg/ml) as above, and cress radicle length was measured after 72 hr. The experiment was repeated three times.

Example 6

High Performance Liquid Chromatography (HPLC)

Fescue root exudates, cv Intrigue, were collected and compared using two separate production methods: (1) a capillary mat was utilized to collect large quantities of root exudates, and (2) root exudate was extracted from the water-based agar medium where fine leaf fescue had been grown for 5 weeks. Root exudate was extracted by homogenizing the agar medium in methylene chloride. This solution had been filtered through Whatman #4 filter paper. The filtrate was dried using rotoevaporation at room temperature. A comparison of these root exudates was performed by HPLC to evaluate the chemical composition of bioactive root exudates under two different growth conditions. Exudate separation was accomplished using an HPLC (Waters, Inc.) equipped with a photodiode array detection, evaluating at 230 mm. The column utilized was a Xterra RP 18 (3.9 £100 nm) (Waters, Inc.). Compounds were separated using a binary solvent system of acetonitrile and acidified water (2.5% acetic acid) over 30 min. The solvent composition was maintained at 20% acetonitrile for the first 20 min. At time 20 min, the solvent was stepped up to 100% acetonitrile at which it was maintained for 5 min before returning to the initial solvent conditions for subsequent analyses.

Example 7

Data Analysis

All data collected in regard to Examples 1-6 and 8-14 (described herein) were subjected to analysis of variance with repeated measures. Mean separations were performed using Fisher's protected LSD at the 5% significance level.

Example 8

Microscopy

One fine leaf fescue, cv Intrigue, was chosen for further study on the basis of its potent allelopathic activity in prior laboratory assays. Hypochloritetreated seed was placed onto a capillary mat system and allowed to germinate at room temperature (25±C) for 1 week, providing root tissue with ample surface area for examination under light and electron microscope.

Light Microscopy. Fresh roots were deposited on an Olympus SZX 12 (obj 90) on a wet paper towel, and root tips were observed.

Electron Microscopy. Fresh roots were fixed in glutaraldehyde, and washed by bathing several times in distilled water. Methanol was used to dehydrate roots to the critical point at which the root was completely dry. Dry roots were glued onto aluminum specimen stubs with conductive carbon disks. The specimen stub was coated with 30 nM of gold/palladium (60/40) in a sputter coater. Scanning electron micrographs were taken with a JEOL JSM 840 scanning electron microscope. For transmission electron microscopy (TEM), 2-mm cross-sections of fine leaf fescue roots were immersed in fixative buffer (4% glutaraldehyde in 0.1 M cacodylate buffer) overnight. The next day, samples were rinsed in 0.66 M cacodylic buffer for 30 min followed by a 1-hr postfixation in 1% $OsO_4$. Samples were rinsed in distilled water for resin. Thin sections, obtained with an ultramicrotome, were stained in 2% uranyl acetate and Reynolds lead citrate. Sections were observed using a Zeiss EM10CR transmission electron microscope.

Example 9

Screening for Allelopathic Potential

Figure 2:
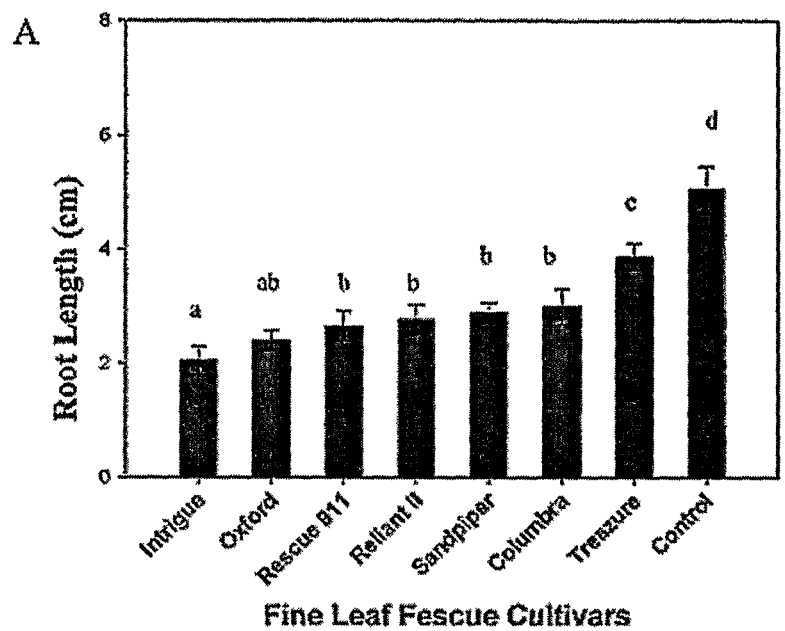
FIGS. 2A and 2B show inhibition of seedling root elongation of curly cress (*Lepidium sativum* L.) by presence of fine leaf fescue seedlings established for 1 week (FIG. 2A) or 3 weeks (FIG. 2B), and removed from the growth medium before reseeding with cress. Bars represent § one standard error unit. Values with the same letter are not significantly different with Fisher's protected LSD test at the 0.05 level.
Figure 2:
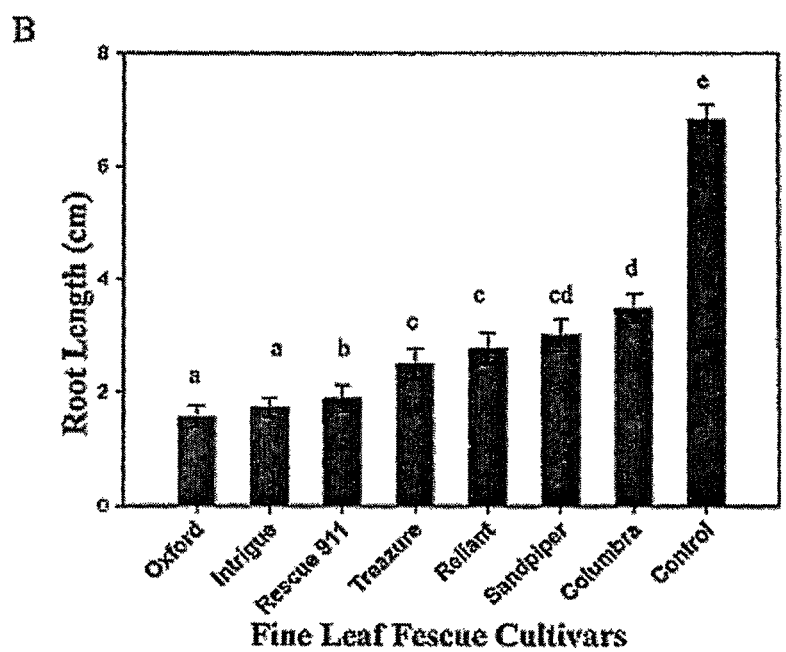

Of the seven fescue cultivars evaluated, all reduced mean root and shoot lengths of large crabgrass and curly cress (FIG. 1). Inhibition due to the presence of fescue ranged from 46% ("Treazure") to 80% ("Intrigue") for crabgrass and from 21% (Treazure) to 58% (Intrigue) when curly cress was the test species. Root length was generally inhibited more than shoot length for all fescue cultivars evaluated. For example, in the presence of cv "Intrigue," root length of curly cress was inhibited by 58%, while shoot length was inhibited by 37%. When fescue seedlings were removed from the agar before seeding with the indicator species, cress root length was still noted and inhibition increased with increasing residence time in the agar medium. Fescue seedlings established for 3 weeks resulted in a more suppressive growth media than those seeded for only 1 week when cress seedling growth was evaluated (FIG. 2).

Example 10

Root Exudate Collection Under Stressed and Nonstressed Conditions

When produced using a capillary mat system, fresh root fescue cultivars yielded varying quantities of root exudates, ranging from 0.14 mg exudate/g of fresh root (Columbra and Rescue) to 0.83 mg/g (Sandpiper). Intrigue and Treazure yielded intermediate amounts exudates with 0.53 and 0.55 mg of exudate/g root tissue, respectively. Drier conditions during seedling growth on the capillary mat led to a considerable increase in production of root exudates (Table 2).

TABLE 2

PRODUCTION OF FINE LEAF FESCUE ROOT EXUDATE AMOUNT COLLECTED FROM SEVEN DIFFERENT CULTIVARS UNDER TWO GROWTH CONDITIONS

| Fine leaf fescue cultivar | Root exudate production (mg/g)[a,b] | |
| --- | --- | --- |
| | Normal conditions | Dry conditions |
| Intrigue | 0.53 ± 0.03 | 1.43 ± 0.04 |
| Sandpiper | 0.83 ± 0.03 | 1.62 ± 0.06 |
| Rescue | 0.40 ± 0.03 | 0.90 ± 0.05 |
| Columbra | 0.55 ± 0.02 | 0.29 ± 0.06 |
| Oxford | 0.15 ± 0.02 | 0.31 ± 0.05 |
| Reliant | 0.57 ± 0.01 | 1.23 ± 0.03 |
| Treazure | 0.55 ± 0.02 | 1.20 ± 0.08 |

[a]Measurements of fine leaf fescue fresh root weight were obtained 2 weeks after seeding on a capillary mat system.
[b]Average exudate production was calculated on the basis of 18 total replicates, with 6 replicated values obtained from each of three separate experimental mat systems. Standard error was calculated.

Production of root exudates by 14-day-old seedlings was doubled under drier growth conditions.

Example 11

Figure 3:
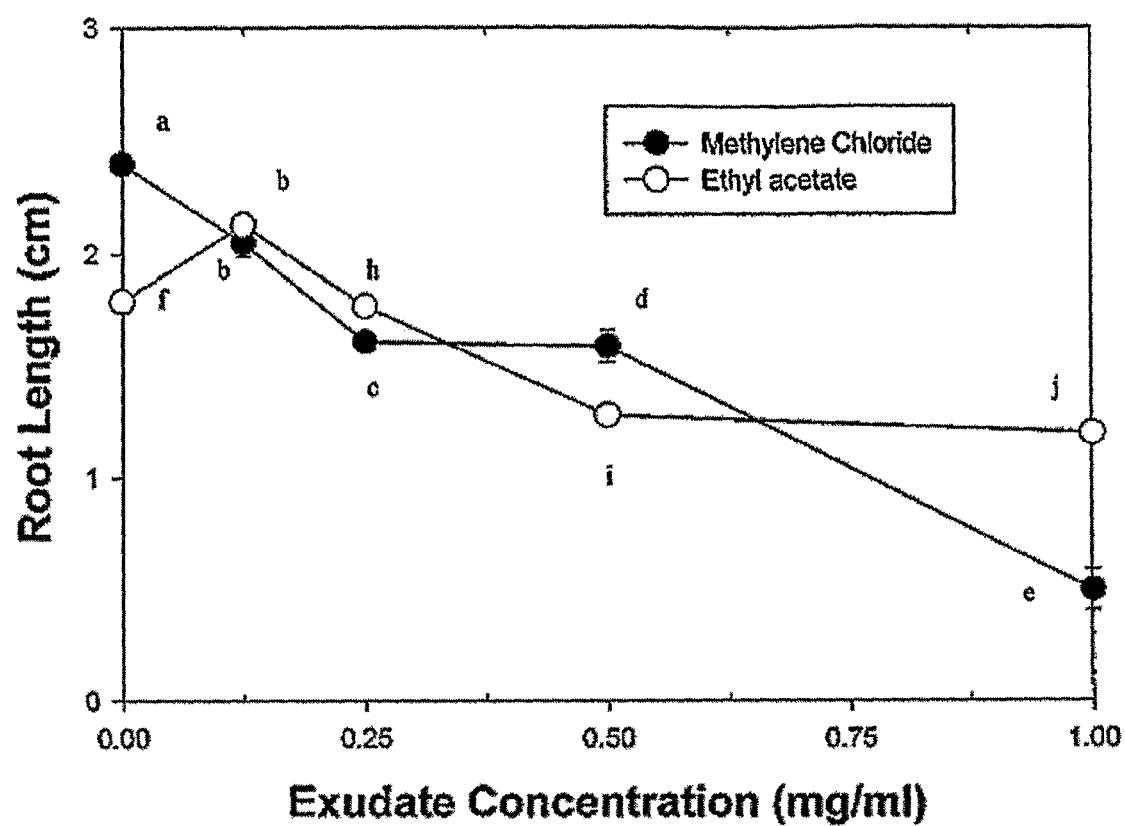
FIG. 3 shows the influence of ethyl acetate and methylene chloride extracts of fine leaf fescue shoots, cv "Intrigue," on root length of curly cress (*Lepidium sativum* L.) 72 hr after germination. Bars represent § one standard error unit. Values with the same letter are not significantly different with Fisher's protected LSD test at the 0.05 level.

Influence of Fine Leaf Fescue Root Exudates and Shoot Extracts on Cress Root Length Methylene chloride and ethyl acetate extracts of fescue root exudates caused significant decreases in root length of curly cress seedlings after 72-hr growth (FIG. 3). Root length was a more sensitive indicator of growth inhibition than seed germination or shoot length. Root exudates, at similar concentrations, were more inhibitory to root growth of the indicator species than were shoot extracts. The methylene chloride fraction collected from partitioning of the aqueous shoot extract was most inhibitory to curly cress radicle elongation compared with other solvent fractions, with 40% inhibition of root elongation at a concentration of 0.25 mg/ml. In comparison, the hexane fractions did not inhibit radicle elongation at all, whereas the ethyl acetate fractions resulted in 27% inhibition when the concentration reached 1 mg/ml (FIG. 3).

Example 12

HPLC

Figure 4:
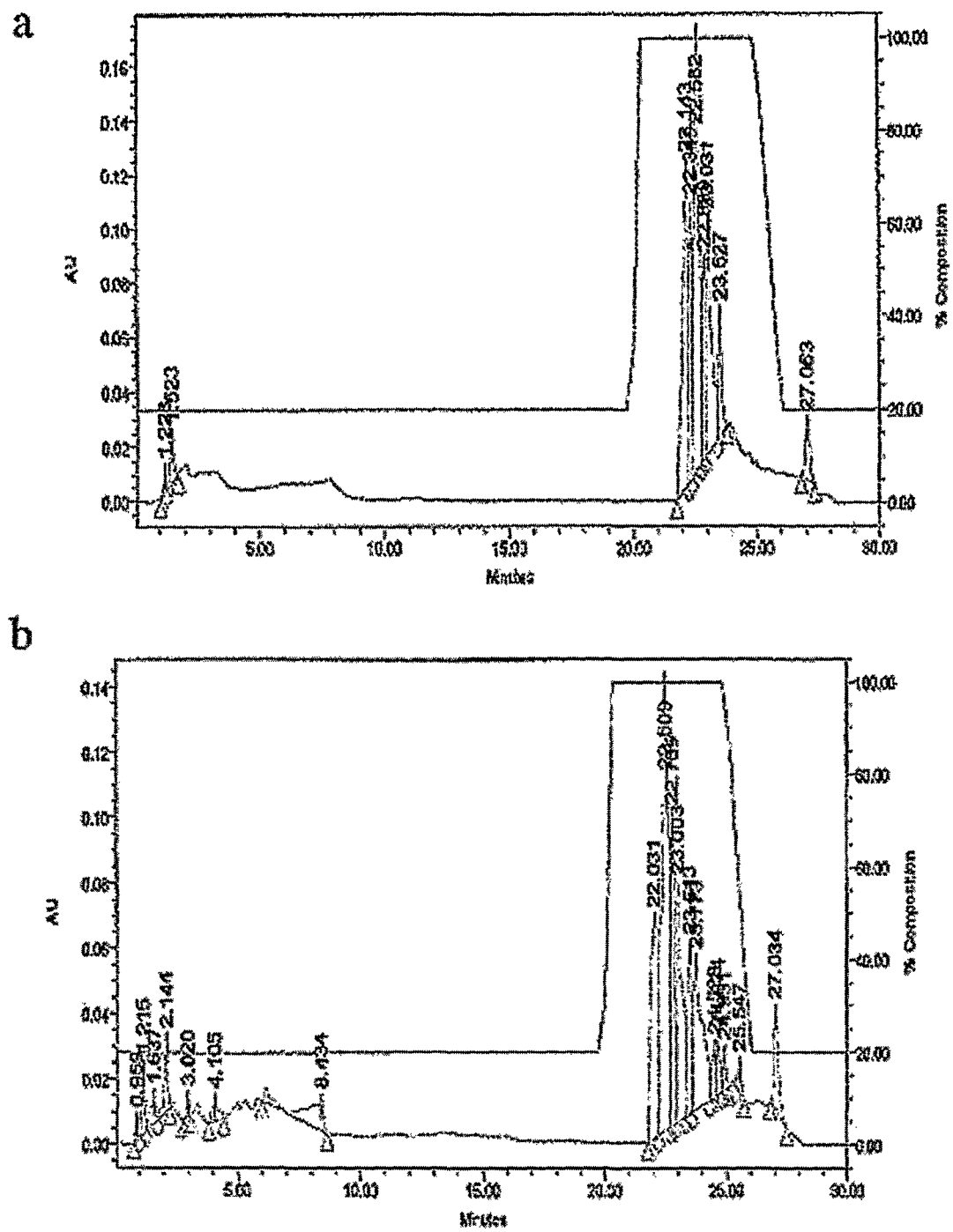
FIGS. 4A and 4B show the relationships between chemical composition of root exudates when roots are produced using agar medium (FIG. 4A), a capillary mat system (FIG. 4B).

Fifteen to twenty major components within each root exudates were observed using reverse phase HPLC for separation (FIG. 4). This bioactive root exudate is apparently released naturally by living fine fescue seedlings in sufficient quantities within both agar growth assays, and also under field conditions, to result in inhibition of weed seed germination and growth. The exudates also can be collected in large quantities when roots are produced on a capillary mat system, and the resulting exudates cause inhibition of seed germination at very low concentrations.

Using a methylene chloride extraction of the agar medium, where fine leaf fescue seedlings were grown for 14 days, thin layer chromatography and HPLC indicated that constituents present in the root exudates extracted directly from roots also were present in the agar medium (FIG. 4).

Example 13

Light and Electron Microscopy Studies

Figure 5:
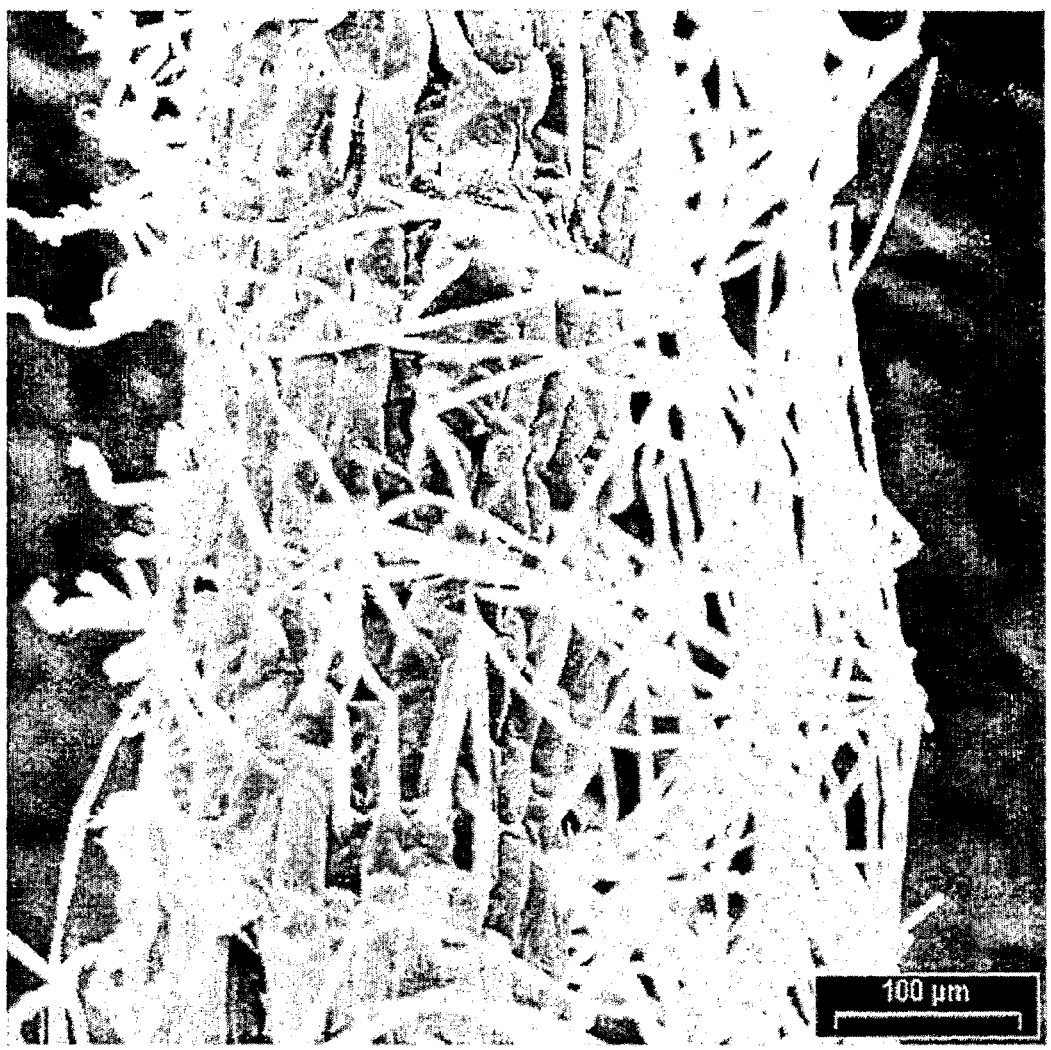
FIG. 5 is an SEM of root hairs present on fine leaf fescue root.

When grown on a capillary mat system, fine leaf fescue seedlings produced a large quantity of fibrous roots and tiny living root hairs, which originated from single cells attached to the main fibrous root system (FIG. 5). The root hairs themselves did not appear to be the origin of root production of the exudates. Their function may only be enhancement of the overall root absorbing surface area for water and nutrient resources. SEM images indicated that the root hairs were actually prolongations of individual epidermal root cells. No droplets of the root exudate were detected at the root hair tips.

Figure 6:
FIG. 6 shows a root tip of fine leaf fescue cv "Intrigue" secreting a brown exudate containing the allelochemicals assumed to be responsible for its allelopathic effect.
Figure 7:
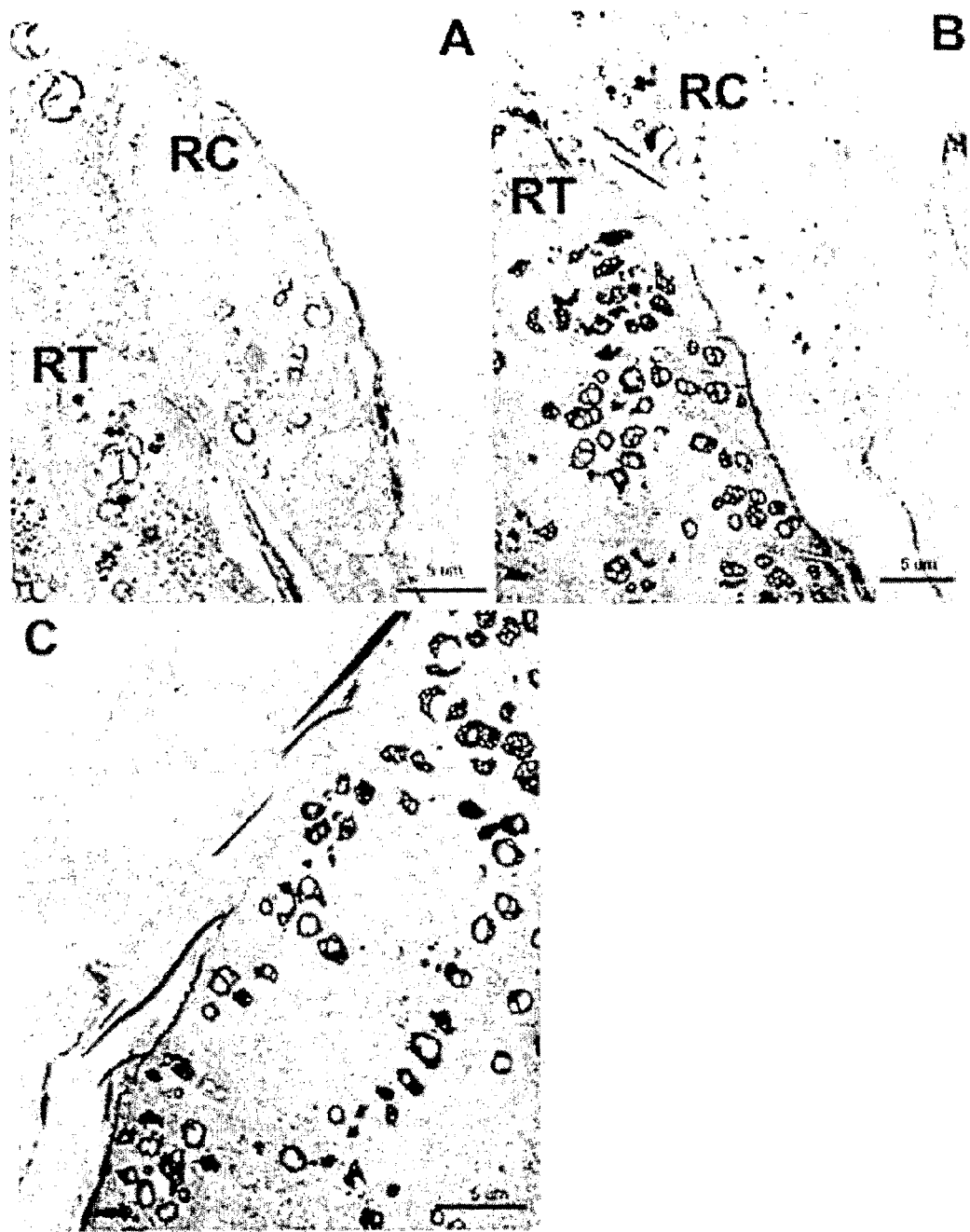
FIGS. 7A, 7B, and 7C show cross-sections of a typical fine leaf fescue fibrous root (cv "Intrigue") showing the presence of numerous darkly stained inclusions in the cytoplasm of epithelium cells. RT: Root tip. RC: Root cap.

However, a smaller structure was observed at the tips of all roots when observed under the light microscope (FIG. 6). This structure, observed under electron microscopy, showed that the epithelium cells located at the tips of living fibrous roots were cytoplasmically dense and appeared to serve as metabolic sites for the production of bioactive root exudates (FIG. 7). The presence of numerous cellular organelles such as golgi bodies, endoplasmic reticulum, and mitochondria implies that the bioactive root exudates are synthesized within the epithelium cells and temporarily stored in small osmiophilic secretory vesicles located in the cytoplasm of these cells. In contrast, a similar study performed on lemna root tips was conducted for comparative purposes. Using the same technique, lemna root tip cells possessed limited quantities of endoplasmic reticulum, golgi, and ribosomes and few, if any, dense osmiophilic inclusions, as seen in fescue tips.

Example 14

Discussion of Examples 1-13

Evidence for the allelopathic potential of any species may depend as much on the choice of method used to bioassay the activity, as on the choice of species (Stowe, L. G., "Allelopathy and Its Influence on the Distribution of Plants in an Illinois Old-Field," *J. Ecol.* 76:1065-1085 (1979), which is hereby incorporated by reference in its entirety). Large crabgrass is a widespread weed in most U.S. turf setting, including golf courses and athletic fields. Curly cress was used as another test species because of its uniform germination and the fact that it is a broadleaf. Success or failure in separating allelopathy from inhibition associated with resource competition can be influenced by a lack of rigorous methodology (Fuerst et al., "Separating the Competitive and Allelopathic Components of Interference. Theoretical Principles," *J. Chem. Ecol.* 19:937-944 (1983), which is hereby incorporated by reference in its entirety). The choice of bioassays is, therefore, a major determining factor in screening programs seeking to draw conclusions about the allelopathic potential of the species in question. Utilization of intact plants and the development of experiments that reasonably simulate the natural conditions encountered during plant interference are two key criteria for developing convincing methods to assess allelopathic potential (Inderjit et al., "Are Laboratory Bioassays for Allelopathy Suitable for Prediction of Field Responses?," *J. Chem. Ecol.* 26:2111-2118 (2000), which is hereby incorporated by reference in its entirety). The study described in Examples 1-13 (herein) attempted to address a number of these issues by designing experiments using 0.8% water agar, which ensured a stable support for plant growth and uniform moisture uptake in both fescue and the indicator species. The use of agar-containing magenta boxes also allowed us to later remove fescue seedlings from each container, leaving behind the growth media containing root exudates and potential allelochemicals. This created a more conclusive means to prevent competition for resources from impacting plant growth, while demonstrating allelopathic effects because of production of bioactive root exudates. Light supply was not limiting and was equally distributed within the magenta boxes because of the fine, upright canopy architecture of the fescue seedlings. Therefore, it is not believed that light was a limiting factor for test species development. Nutrient competition was also negated as an important factor in the study of Examples 1-13. Although nutrients were not added to the agar growth medium, experiments were conducted for such a short duration that resources providing for initial seedling growth were obtained from seed reserves and likely not limiting, judging by the healthy green appearance and growth of the control seedlings in the absence of living fescue. In addition, removal of the fine leaf fescue seedlings from the magenta boxes allowed for later replant monocultures of the test species and clearly demonstrate the presence of bioactive inhibitors in the growth medium. Competition for space, moisture, or nutrients where living fescue was no longer present was essentially eliminated for test seedlings harvested shortly after planting.

These experiments provide strong evidence that fine leaf fescue seedlings are producing bioactive root exudates that reduce the growth of surrounding plants, including large crabgrass, curly cress, and lettuce. All fescue accessions showed allelopathic potential either when fescue was present or later removed from the agar medium. Lack of reproducibility is a common problem in allelopathy research (Latto et al., "Allelopathy in Seeds," *J. Biol. Educ.* 29:123-128 (1995), which is hereby incorporated by reference in its entirety); however, in both field experiments and laboratory assays, certain fescue cultivars were observed to be more suppressive. Veronneau et al., "Uses of Mixtures of Allelochemicals to Compare Bioassays Using Red Maple, Pin Cherry, and American Elm," *J. Chem. Ecol.* 23:1101-1117 (1997), which is hereby incorporated by reference in its entirety, suggested that reproducible results from two or more bioassays systems were required to demonstrate allelopathic potential in plants. In this case (Examples 1-13), cultivars Intrigue, Sandpiper, and Oxford were generally more suppressive than "Reliant II" and "Columbra," in both field and laboratory assays (Bertin et al., "Further Evaluation of the Allelopathic Potential of Fine Leaf Fescue," *Proc WSSA* 56:116 (2002), which is hereby incorporated by reference in its entirety).

The cultivar "Treazure" was not suppressive in 2 years of field settings in two different locations. Also, it was not suppressive in a laboratory setting. Under field conditions, more factors are to be taken into consideration than those under laboratory settings to understand the process of weed suppressivity. Differences observed in weed-suppressive ability of the same cultivar between in-field and in-laboratory might be due to the inherent complexity of the rhizosphere versus a gel medium. Soil moisture, texture and particle size, water content, buffering capacity, and microorganism populations may all interact with root exudates and influence the activity of chemicals released by plants. However, many similar trends were observed among field and laboratory assays in relative toxicity of cultivars and long-term suppressivity.

Even though results obtained from solvent extractions or from maceration and grinding of plant materials may result in the liberation of chemicals that would not normally be released in the field by living tissue (Lovett et al., "Effects of Residues of Crop Plants on Germination and Early Growth of Wheat," *Aust. J. Agric. Res.* 33:909-916 (1982), which is hereby incorporated by reference in its entirety), such studies have the potential to indicate allelopathic potential, both during the life of the plant and later during decomposition of plant residues (Inderjit et al., "Are Laboratory Bioassays for Allelopathy Suitable for Prediction of Field Responses?," *J. Chem. Ecol.* 26:2111-2118 (2000), which is hereby incorporated by reference in its entirety). The somewhat inhibitory activity of the ethyl acetate and methylene chloride leaf extract of the fine leaf fescue accessions suggests the presence of phytotoxic constituents within these extracts. Leaf extracts of other crops and grassland forage species can also reduce the growth of certain test and weed species (Weston et al., "Allelopathic Potential of *Sorghum*-Sudangrass Hybrid (sudex)," *J. Chem. Ecol.* 15:1855-1865 (1989); Creamer et al., "Mechanisms of Weed Suppression in Cover Crop-Based Population System," *Hortic. Sci.* 31:410-413 (1996); Wardle et al., "Use of Comparative Approach to Identify Allelopathic Potential and Relationship Between Allelopathy Bioassays and "Competition" Experiments for Ten Grassland and Plant Species," *J. Chem. Ecol.* 2:933-948 (1996), which are hereby incorporated by reference in their entirety).

Whether the presence of these secondary products in shoot tissues impacts the allelopathic activity of decomposing fescue residues in the field remains to be seen. Root systems of various plants have been shown to be the site of production of root exudates with potent allelopathic potential, including sorghum (*Sorghum bicolor* L. Moensch) and black walnut (*Juglans nigra* L). These plants produce exudates containing mixtures of related hydroquinones, which are potent inhibitors of photosynthesis or respiration in higher plant systems (Einhellig et al., "Effects of Root Exudates Sorgoleone on Photosynthesis," *J. Chem. Ecol.* 19:369-375 (1993); Hejl et al., "Effects of Juglone on Growth, Photosynthesis and Respiration," *J. Chem. Ecol.* 19:559-568 (1993), which are hereby incorporated by reference in their entirety). The agar bioassays have shown that the root system of fine fescue is responsible for producing allelochemicals, which have potent inhibitory activity upon developing weed seedlings. The agar extract that previously supported the growth of the living root systems of fine fescue seedlings contained identical chemical constituents, as did the root exudates collected from living fescue root extraction. Fine leaf fescue accessions appear to exhibit marked differences in their ability to produce root exudates when grown under identical Environmental conditions, suggesting that genetic diversity for exudate production exists within the collection of fine fescue cultivars.

The exact role of the fescue root exudates in the rhizosphere is unknown. Exudate production may be logically associated with plant defense, which is particularly important during seedling phase of growth. Differences in production of root exudates may be associated with the ability of fine leaf fescue cultivars to exhibit differential suppressivity in the field and the laboratory. Environmental factors also may influence both competition and allelopathic trait expression in fescue cultivars. Although further studies are required to elucidate bioactive constituents within the root exudates and determine their specific activity and mode of action in inhibiting weed seedling growth, strong evidence from both field and laboratory experiments suggests a role for allelopathic interference by certain cultivars of fine fescue. Endophytes are widespread in the grasses (White, J. F., JR., "Endophyte-Host Association in Forage Grasses. XI: A Proposal Concerning Origin and Evolution," *Mycology* 80:442-446 (1988); Clay et al., "Infection of Woodland Grasses by Fungal Endophytes," *Mycology* 81:805-811 (1989), which are hereby incorporated by reference in their entirety) and influence turfgrass quality and pest resistance, but are also associated with mammalian toxicosis. All the fine leaf fescue cultivars were positively tested for the presence of endophyte by using Bacon's method. One could suggest that the presence of the endophyte might have a positive influence on the production and the toxicity of the root exudates. However, electron microscopy studies of the fine leaf fescue roots showed a complete absence of the endophyte, suggesting that, even though present in the seed and in the shoot of fine leaf fescue cultivars, the endophyte appears not to be associated with root exudate production or toxicity.

Past studies with a variety of plants have shown that root exudates generally contain a variety of organic constituents, which are released into the rhizosphere. Root exudates are often chemically diverse and include simple low-molecular weight compounds such as organic acids, sugars, and amino acids as well as more complex substances, including vitamins, plant hormones, and secondary products (Rovira, A. D., "Plant Root Exudates," *Bot. Rev.* 35:35-59 (1969), which is hereby incorporated by reference in its entirety). The presence of cytoplasmically dense root tip cells of fine fescue containing large numbers of organelles including endoplasmic reticulum, Golgi bodies, and ribosomes, suggests that actively dividing fine fescue root cells are the site of production of the bioactive secondary products found within fescue root exudates. When examining the entire length of living fescue root systems, a differential pattern in production of secondary products was noted. Living roots originating near the growing point showed an absence of osmophilic compounds and organelles involved with synthesis, while living roots tips had an increased presence of metabolic organelles and vesicles containing dark staining chemical constituents. This observation suggests that fine leaf fescue root exudates are synthesized mainly within the tips or ends of actively dividing fibrous roots. The mechanism of excretion of these compounds from living roots is under consideration. One could hypothesize that during the natural process of suberization and autolysis of root cortical cells, the products of autolysis may enter the rhizosphere. Further studies to better understand the mechanism of root exudate excretion are under way, along with studies to chemically characterize all of the major constituents within these bioactive root exudates. The impact of environment on exudate production and weed suppression is also of interest. This information may allow for the development and utilization of fine leaf fescue cultivars more effectively for their long-term weed-suppressive properties in the landscape. As an example, this can be done through plant breeding programs.

Example 15

Evaluation of Selected Fine Leaf Fescue Cultivars for Their Weed Suppressive Ability in Various Field Settings The objectives of the study described in Examples 16-21 (herein) were conducted to evaluate turfgrass quality and weed suppressive ability of fine leaf fescue cultivars over a three-year period. Based on initial evaluations, a subset of fine leaf fescue cultivars was further evaluated in additional field trials conducted over a two-year period.

A series of field studies were conducted from 1999-2005 in Ithaca, N.Y. at the Cornell Turfgrass Research Center as part of the National Turfgrass Evaluation Program (NTEP) to evaluate a collection of 78 fine leaf fescue cultivars for turfgrass quality, seedling vigor, and ability to inhibit the establishment of common annual and perennial weeds. Using these criteria, the overall suitability of the cultivars for use in turfgrass settings were evaluated, as well as their potential weed suppressive or allelopathic ability. The ability of fine fescues to displace weeds was visually evaluated, and several cultivars out of the 78 studied consistently established well and provided good to very good suppression (greater than 70%) of common turf weeds when established using the same planting density. Other cultivars provided moderate (between 35%-70%) to (<30%) little weed suppression. Greater weed suppressivity is likely associated with the differential ability of fescue cultivars to establish rapidly and to form a dense canopy, as well as potential allelopathic interference. The study described in Examples 15-21 (herein) was conducted in conjunction with laboratory experiments which revealed that certain fine leaf fescues produced phytotoxic root exudates that were released into the rhizosphere over time. Additional field studies conducted in Ithaca, N.Y. showed that cultivars Intrigue, Columbra, and Sandpiper were consistently more weed suppressive than other fine leaf fescues evaluated. Further studies are relevant to improve the understanding of the chemical and biological dynamics of fine fescue root exudates and their associated phytotoxins in the rhizosphere.

Example 16

National Turfgrass Evaluation Program (NTEP) Experiment

The National Turfgrass Evaluation Program (NTEP) is a program sponsored by the United States Department of Agriculture (USDA) which generates data comparing cultivar performance of various turfgrass species in multiple settings across North America. In 1998, an NTEP fine leaf fescue trial was established at Cornell University's Turfgrass Research Center in Ithaca, N.Y. Soil type was an Arkport fine sandy loam (psamentic Hapludlafs, coarse loamy mixed mesic), with a pH of 5.9 and organic matter content of approximately 3.2%. Fine leaf fescue species evaluated included blue fescue, chewing's fescue, hard fescue, sheep fescue, strong creeping red fescue, and slender creeping fescue (Table 3).

TABLE 3

Results obtained from the NTEP trial conducted in Ithaca, NY from 1998 to 2001. Fine leaf fescue cultivars evaluated for turfgrass quality, seedling vigor, spring greenup, and summer density. Data are averaged across 1999 and 2002.

| Cultivar | Species | Turfgrass quality[1] | Seedling Vigor[2] | Spring Greenup[3] | Summer Density[4] |
|---|---|---|---|---|---|
| ASC 172 | strong creeping | 4.5 | 4.3 | 6.7 | 7.3 |
| Bighorn | hard | 4.9 | 4.3 | 6.5 | 6.7 |
| Osprey | hard | 5.3 | 4.3 | 6.0 | 6.7 |
| Berkshire (4001) | hard | 5.7 | 4.7 | 5.8 | 7.3 |
| MB-82 | hard | 5.1 | 4.7 | 6.3 | 6.7 |
| Pick FF A-97 | hard | 5.3 | 4.7 | 6.0 | 7.0 |
| PST-4HM | hard | 5.3 | 4.7 | 6.3 | 7.0 |
| Rescue 911 | hard | 5.2 | 4.7 | 6.7 | 7.0 |
| ABT-HF-4 | hard | 5.3 | 5.0 | 6.5 | 7.3 |
| PST-4MB | blue hard | 5.4 | 5.0 | 6.2 | 6.7 |
| Scaldis | hard | 5.1 | 5.0 | 6.3 | 7.0 |
| SR 3200 | blue | 4.8 | 5.0 | 6.8 | 6.3 |
| ABT-HF-2 | hard | 5.5 | 5.3 | 6.0 | 7.0 |
| ASC 082 | strong creeping | 4.9 | 5.3 | 6.2 | 7.0 |
| Attila E | hard | 5.0 | 5.3 | 6.3 | 6.7 |
| Banner III | chewings | 5.2 | 5.3 | 6.8 | 7.0 |
| Heron | hard | 5.2 | 5.3 | 6.7 | 7.0 |
| Nordic (E) | hard | 5.4 | 5.3 | 5.8 | 6.7 |
| Oxford | hard | 5.6 | 5.3 | 6.7 | 6.7 |
| PST-4FR | strong creeping | 5.2 | 5.3 | 6.7 | 7.0 |
| Reliant II | hard | 5.3 | 5.3 | 6.3 | 6.7 |
| Scaldis II (AHF008) | hard | 5.1 | 5.3 | 6.0 | 7.0 |
| Shadow II | chewings | 5.5 | 5.3 | 6.3 | 6.7 |
| SRX 3961 | hard | 5.6 | 5.3 | 6.2 | 7.0 |
| ABT-CR-2 | strong creeping | 5.4 | 5.7 | 6.2 | 6.7 |
| ABT-HF-3 | hard | 5.3 | 5.7 | 6.2 | 6.7 |
| ACF 083 | chewings | 5.1 | 5.7 | 6.0 | 6.3 |
| Ambassador | chewings | 5.7 | 5.7 | 7.0 | 7.3 |
| Ambrose (ABT-CHW-3) | chewings | 5.7 | 5.7 | 7.0 | 7.0 |
| BAR CHF 8 FUS2 | chewings | 5.3 | 5.7 | 6.0 | 6.7 |
| Chariot (CIS FI 12) | hard | 5.5 | 5.7 | 6.3 | 6.7 |
| Defiant | hard | 5.1 | 5.7 | 6.5 | 7.0 |
| Eureka II (CIS FI 11) | hard | 5.4 | 5.7 | 6.2 | 6.7 |
| Hardtop (BAR HF 8 FUS) | hard | 5.5 | 5.7 | 6.0 | 6.3 |
| Magic | chewings | 5.4 | 5.7 | 6.0 | 7.3 |
| Minotaur | hard | 5.3 | 5.7 | 6.3 | 7.0 |
| Quatro | sheep | 5.0 | 5.7 | 6.3 | 6.7 |
| Shademark | strong creeping | 4.8 | 5.7 | 5.7 | 7.3 |
| SR 5210 (SRX 52LAV) | strong creeping | 5.1 | 5.7 | 6.0 | 7 |
| Stonehenge (AHF 009) | hard | 5.4 | 5.7 | 6.7 | 7.0 |
| Viking (ABT-HF1) | hard | 5.8 | 5.7 | 6.5 | 7.0 |
| ABT-CHW-1 | chewings | 5.4 | 6.0 | 6.0 | 7.0 |
| ABT-CHW-2 | chewings | 5.7 | 6.0 | 6.5 | 7.3 |
| ASR 049 | slender creeping | 5.0 | 6.0 | 6.2 | 6.7 |
| BAR SCF 8 FUS3 | slender creeping | 5.1 | 6.0 | 6.3 | 6.7 |
| Bargena III (BAR CF 8 FUS1) | strong creeping | 5.1 | 6.0 | 6.5 | 6.7 |
| Brittany | chewings | 5.3 | 6.0 | 6.7 | 7.0 |
| Common creeping red | strong creeping | 4.3 | 6.0 | 6.0 | 7.0 |
| Dawson E+ | slender creeping | 4.8 | 6.0 | 5.5 | 6.7 |
| DGSC 94 | strong creeping | 5.0 | 6.0 | 6.3 | 7 |

TABLE 3-continued

Results obtained from the NTEP trial conducted in Ithaca, NY from 1998 to 2001. Fine leaf fescue cultivars evaluated for turfgrass quality, seedling vigor, spring greenup, and summer density. Data are averaged across 1999 and 2002.

| Cultivar | Species | Turfgrass quality[1] | Seedling Vigor[2] | Spring Greenup[3] | Summer Density[4] |
|---|---|---|---|---|---|
| Discovery | hard | 5.3 | 6.0 | 6.5 | 6.7 |
| Inverness (PST-47TCR) | strong creeping | 5.1 | 6.0 | 6.5 | 7.0 |
| Jasper II | strong creeping | 5.8 | 6.0 | 6.5 | 7.0 |
| Longfellow II | chewings | 5.9 | 6.0 | 6.2 | 7.0 |
| MB-63 | chewings | 5.3 | 6.0 | 5.8 | 7.0 |
| Pick Frc A-93 | chewings | 5.5 | 6.0 | 6.3 | 7.0 |
| Rose (ASC 087) | strong creeping | 4.8 | 6.0 | 5.8 | 6.7 |
| Shademaster II | strong creeping | 5.1 | 6.0 | 5.8 | 7.0 |
| Silhouette (Pick Frc 4-92) | chewings | 5.3 | 6.0 | 6.5 | 7.0 |
| SR 5100 | chewings | 5.4 | 6.0 | 6.0 | 6.7 |
| Tiffany | chewings | 5.3 | 6.0 | 6.2 | 6.7 |
| Treazure (E) | chewings | 5.6 | 6.0 | 6.2 | 8.0 |
| Wrigley (ACF 092) | chewings | 5.3 | 6.0 | 6.0 | 7.0 |
| ABT-CR-3 | strong creeping | 5.6 | 6.3 | 6.2 | 7.0 |
| Bridgeport | chewings | 5.3 | 6.3 | 5.8 | 7.0 |
| Cindy Lou (CIS Frr 7) | strong creeping | 5.7 | 6.3 | 6.3 | 6.7 |
| Culombra | chewings | 5.4 | 6.3 | 6.2 | 7.0 |
| Florentine | strong creeping | 5.2 | 6.3 | 6.3 | 7.0 |
| Intrigue | chewings | 5.7 | 6.3 | 7.0 | 6.7 |
| Jamestown II | chewings | 5.1 | 6.3 | 5.5 | 7.0 |
| Navigator (CIS Frr 5) | strong creeping | 5.6 | 6.3 | 5.7 | 7.0 |
| Pathfinder | strong creeping | 5.3 | 6.3 | 6.0 | 7.0 |
| Seabreeze | slender creeping | 5.0 | 6.3 | 5.5 | 7.3 |
| Aberdeen (PST-EFL) | strong creeping | 5.5 | 6.7 | 6.0 | 7.0 |
| Sandpiper | chewings | 5.2 | 6.7 | 5.2 | 7.3 |
| SRX 52961 | strong creeping | 5.7 | 6.7 | 6.0 | 6.3 |
| Boreal | strong creeping | 4.4 | 7.0 | 5.5 | 7.0 |
| Salsa | strong creeping | 5.0 | 7.0 | 5.5 | 7.7 |
| SR 6000 | tufted hairgrass | 3.7 | 7.0 | 6.2 | 6.0 |
| lsd | | 0.2 | 0.9 | 1.0 | 0.8 |
| cv | | 10.7 | 9.9 | 10 | 7.3 |

[1]Turf quality ratings were based on a scale of 1 to 9, with 1 representing poor or dead turf and 9 being outstanding or ideal
[2]Seedling vigor is rated on a 1 to 9 scale with 9 equaling maximum vigor
[3]Spring greenup was based on a visual rating scale with 1 being straw brown and 9 being completely green
[4]Summer density is a visual rating of 1 to 9 is used with 9 equaling maximum density. Density ratings were collected in the summer Prior to seeding, the ground was prepared by removal of existing vegetation with the non-selective herbicide glyphosate applied at a standard rate of 1.12 kg ai/ha, followed by incorporation of the residue into the soil. On 2 Jun., 1998 after further grading, the soil fumigant dazomet was applied at 390 kg ai/ha. The soil was then tilled, and rolled. Prior to seeding, 25 kg/ha starter fertilizer (18-24-12) was applied to the seedbed. Plots (1.85 m$^2$) were seeded by hand on 15 Jun., 1998 at a rate of 22 kg/ha and irrigated regularly for 5-7 days after seeding. Cultivar treatments were established within a randomized complete block design with three blocks.

Plots were irrigated to maintain surface moisture until turf reached 60% cover at which time irrigation was reduced to allow surface drying, and a second application of fertilizer was applied. Vegetation was mowed using a reel mower when plants were 5 cm tall, and irrigation was applied to prevent dormancy. When plants reached 2.5 cm height, nitrogen was applied at a rate of 25 kg/ha to simulate golf fairway turf conditions. From 1999-2001, plots were maintained without supplemental irrigation, fertilization, or weed management using standard cultural practices for mowing to simulate fairway turf where height was maintained at 1.9 cm.

Turfgrass was evaluated for quality, density, and color on a visual basis using a 1 to 9 scale, with 9 being outstanding or ideal turf and 1 representing dead or poor turf. A rating of 6 or above is considered acceptable. According to NTEP guidelines, turfgrass quality ratings reflect aesthetic and functional aspects of the turf. Quality ratings were based on a combination of color, density, uniformity, texture, and disease infestation or sensitivity to environmental stress. For example, a quality rating value of 5 could be given to a turf based on overall color and density, while another may receive the same value of 5 due to disease incidence and its impact on turfgrass density. Spring greenup evaluation was rated separately and was based on a visual rating performed during the 1999 growing season, with 9 representing darkest green turf and 1 representing dead turf. Evaluations for true color type are best made when the turf is actively growing and not under stress. Therefore, chlorosis and browning from necrosis due to disease were not considered as a part of the genotypic color evaluation.

Data on seedling vigor and spring greenup were obtained only in 1999, with a visual rating taken 90 days after seeding. Seedling vigor, a visual estimate of ground cover and plant height that reflects the relative speed by which a cultivar develops into a mature sod, was also rated on a visual 1-9 scale with 9 indicating maximum vigor.

Weed suppressive ability was determined visually on a monthly basis by the same observer from July to October in 1999, and 2001, and from June to October 2000, using a percentage scale where 0% denoted no weed suppression and 100% represented a weed-free plot.

Example 17

Two Location Experiments

Cultivars with consistently high or low weed suppression ratings from the previous experiment were selected for a second experiment. A two-year field study was conducted at the Long Island Horticultural Research and Extension Center, Riverhead N.Y., in 2001 and at the Cornell University Turfgrass Research and Extension Center, Ithaca, N.Y., to further evaluate the weed suppressive properties of selected fine leaf fescue cultivars. Treatments for each species included: (1) weed to establishment (plots were weeded early in the season until the turf was well established), and (2) no weeding (plots were not weeded during the experiment).

In Riverhead and in Ithaca, N.Y., fescue cultivars 'Attila', 'Boreal', 'Columbra', 'Intrigue', 'Jasper', 'Oxford', 'Reliant II', 'Rescue', 'Sandpiper', and 'Treazure' were seeded at the standard rate of 146 kg/ha in September 2000 into Haven Sandy/Silt Loam or Arkport fine sandy loam, and fertilized only in Riverhead using standard rates (20 kg/ha) of 26-3-10 fertilizer. A phenoxy-based herbicide to control broadleaf weeds was applied at standard rates in Riverhead, N.Y. in April 2001 and in late May in Ithaca, N.Y. for the weed to establishment plots only. Percentage weed cover data were collected from all plots in May and August in both sites during the growing seasons of 2001 and 2002.

Example 18

Ithaca Trial 2003

A third study was performed in Ithaca, N.Y. to further evaluate weed suppression provided by a collection of fine fescue cultivars using a greater number of replications. In September 2003, fine leaf fescue cultivars were seeded at 146 kg/ha, and plots were subsequently rolled and irrigated. As before, weed suppression was evaluated based on visual ratings performed in July and October 2004. Cultivars evaluated included: 'Oxford', 'Reliant II', 'Columbra', 'Rescue 911', 'Sandpiper', and 'Intrigue', and several from Europe including 'Wilma', 'Sylvia High', 'Christina', and 'RS158'.

Percentage weed cover data were subjected to analysis of variance with repeated measures using SAS. Mean separations were performed using Fisher's protected LSD at the 5% significance level.

Example 19

NTEP Experiment (Ithaca, N.Y.) (See Table 1)

Turfgrass quality. Fescue quality ratings from all NTEP trials carried out in North America from 1999 to 2002 were averaged and ranged between 3.7 and 5.9 on a 1 to 9 scale. At the Ithaca site, ratings during this period also ranged between 3.8 and 5.8, suggesting that this location is adequate for fine leaf fescue establishment when compared with other North American regions (Table 3). The monthly ratings from 1999 to 2001 showed that turfgrass quality ranked higher in 1999 (between 4 and 6) than in 2000 and 2001 (between 2 and 4). Differences in turfgrass quality could be potentially associated with climate variation; 1999 was the 3rd driest year in Ithaca, N.Y. since 1969, whereas precipitation levels in 2000 and 2001 were closer to the long term average. The fine and coarse leaf fescues are generally considered to be drought tolerant (Turgeon, A. J., "Turfgrass Management," 5th Ed., Upper Saddle River, N.J.: Pearson Prentice Hall, 392 p. (1999), which is hereby incorporated by reference in its entirety). It is interesting to note that fescue establishment was not negatively impacted by the dry conditions encountered in 1999, suggesting that the cultivars evaluated are also well adapted to drought.

Seedling Vigor. Seedling vigor ratings followed similar trends as those for turfgrass quality (Table 3). In general, cultivars with high vigor ratings also exhibited higher overall turfgrass quality. Vigor or rapid establishment, a trait fescue breeders often select for, appears to be important in influencing overall turfgrass quality, and may have influenced quality readings even in 2000, two full years following turf establishment. Seedling vigor is also an important factor influencing weed infestation in turf, as a vigorous, well established turf results in reduced weed establishment.

Spring greenup. Spring greenup is a measure of the transition from winter dormancy to active spring growth. Aesthetic appeal is very important when considering cultivar selections for golf courses, lawns, and athletic fields. For the 78 cultivars evaluated, ratings varied between 5.2 and 7 on a 1-9 scale, with 1 being completely dormant or brown and 9 being completely green. Findings from this study suggest that the transition between winter dormancy and spring growth in Ithaca, N.Y. was considered average. Spring greenup evaluation is based on plot color, and color evaluation is one of the key visual assessments that account for turfgrass quality; a close relationship between turfgrass quality and color generally exists.

Weed suppressive ability (Table 4). The long-term ability of fine leaf fescue cultivars to suppress weeds over time was evaluated. Weed suppressive ability was evaluated by comparing percent fescue coverage within the plot to percent weed infestation. Weeds encountered included common broadleaf species such as dandelion (*Taraxacum officinale* Weber in Wiggers), broadleaf plantain (*Plantago major* L.), and white clover (*Trifolium repens* L.) as well as grass weeds, including large and smooth crabgrass (*Digitaria sanguinalis* (L.) Scop. and *D. ischaemum* Schreb. ex Muhl.).

TABLE 4

Evaluation of fine leaf fescue cultivars for weed suppressive ability.
Weed suppressive ability[a]

|   | Cultivars | 1999 | 2000 | 2001 |
|---|---|---|---|---|
| 1 | SR 3200 | 43 | 32 | 37 |
| 2 | Minotaur | 50 | 40 | 30 |
| 3 | PST-4MB | 60 | 64 | 61 |
| 4 | ABT-CHW-1 | 47 | 78 | 80 |
| 5 | ABT-CHW-2 | 53 | 58 | 55 |
| 6 | ABT-CHW-3 | 40 | 62 | 60 |
| 8 | ACF 083 | 80 | 68 | 72 |
| 9 | ACF 092 | 43 | 84 | 79 |
| 10 | Ambassador | 57 | 60 | 62 |
| 11 | Banner III | 53 | 62 | 60 |
|   | BAR CHF 8 |   |   |   |
| 12 | FUS2 | 47 | 58 | 50 |
| 13 | Bridgeport | 77 | 62 | 60 |
| 14 | Brittany | 67 | 62 | 60 |
| 15 | Columbra | 37 | 68 | 66 |
| 16 | Intrigue | 53 | 54 | 50 |
| 17 | Jamestown II | 87 | 66 | 66 |
| 18 | Longfellow II | 77 | 76 | 75 |
| 19 | Magic | 53 | 72 | 80 |
| 20 | MB-63 | 67 | 60 | 63 |
| 21 | Pick Frc 4-92 | 57 | 66 | 61 |
| 22 | Pick Frc A-93 | 60 | 70 | 72 |
| 23 | PST-4HM | 53 | 62 | 58 |
| 24 | Sandpiper | 87 | 78 | 80 |
| 25 | Shadow II | 53 | 52 | 55 |
| 26 | SR 5100 | 80 | 76 | 78 |
| 27 | Tiffany | 63 | 56 | 60 |
| 28 | Treazure (E) | 60 | 72 | 70 |
| 29 | 4001 | 73 | 56 | 60 |
| 30 | ABT-HF1 | 47 | 50 | 50 |
| 31 | ABT-HF-2 | 60 | 52 | 55 |
| 32 | ABT-HF-3 | 37 | 64 | 60 |
| 33 | ABT-HF-4 | 57 | 60 | 60 |
| 34 | AHF 008 | 53 | 54 | 55 |
| 35 | AHF 009 | 57 | 26 | 10 |
|   | BAR HF 8 |   |   |   |
| 36 | FUS | 57 | 60 | 60 |
| 37 | bighorn | 50 | 50 | 60 |
| 38 | Defiant | 53 | 54 | 55 |
| 39 | Discovery | 50 | 54 | 55 |
| 40 | Heron | 43 | 40 | 50 |
| 41 | ISI FI 11 | 60 | 44 | 50 |
| 42 | ISI FI 12 | 47 | 48 | 50 |
| 43 | MB-82 | 60 | 58 | 70 |
| 44 | Nordic (E) | 30 | 44 | 50 |
| 45 | Osprey | 60 | 58 | 60 |
| 46 | Oxford | 50 | 66 | 70 |
| 47 | Pick FF A-97 | 80 | 62 | 70 |
| 48 | Reliant II | 57 | 48 | 60 |
| 49 | Rescue 911 | 18 | 34 | 50 |
| 50 | Scaldis | 50 | 50 | 60 |
| 51 | SRX 3961 | 63 | 30 | 50 |
| 52 | Quatro | 67 | 44 | 50 |
| 53 | ASR 049 | 43 | 54 | 50 |
| 54 | Attila E | 73 | 56 | 78 |
|   | BAR SCF 8 |   |   |   |
| 55 | FUS3 | 60 | 52 | 60 |

TABLE 4-continued

Evaluation of fine leaf fescue cultivars for weed suppressive ability.

Weed suppressive ability[a]

| | Cultivars | 1999 | 2000 | 2001 |
|---|---|---|---|---|
| 56 | Dawson E+ | 57 | 54 | 60 |
| 57 | Seabreeze | 63 | 68 | 75 |
| 58 | ABT-CR-2 | 82 | 68 | 75 |
| 59 | ABT-CR-3 | 60 | 58 | 70 |
| 60 | ASC 087 | 63 | 40 | 55 |
| 61 | ASC 172 | 53 | 68 | 66 |
| 62 | ASD 082 | 80 | 46 | 60 |
| | BAR CF 8 | | | |
| 63 | FUS1 | 47 | 66 | 70 |
| 64 | Boreal | 87 | 58 | 60 |
| | Common | | | |
| 65 | creeping red | 57 | 60 | 55 |
| 66 | DGSC 94 | 60 | 56 | 60 |
| 67 | Florentine | 47 | 56 | 55 |
| 68 | ISI Frr 5 | 53 | 56 | 55 |
| 70 | Jasper II | 67 | 60 | 66 |
| 71 | Pathfinder | 33 | 70 | 80 |
| 72 | PST-47TCR | 57 | 76 | 80 |
| 73 | PST-4FR | 70 | 46 | 55 |
| 74 | Salsa | 73 | 78 | 80 |
| 75 | Shademark | 53 | 46 | 50 |
| | Shademaster | | | |
| 76 | II | 73 | 84 | 79 |
| 77 | SRX 52961 | 47 | 82 | 80 |
| 78 | SRX 52LAV | 67 | 76 | 70 |
| | PST-EFL | 57 | 60 | 55 |
| | Scottish links | 35 | 26 | 20 |
| | SR 6000 | 47 | 28 | 18 |
| | l.s.d. | 11 | 9.2 | 10 |

[a]Weed suppressive ability was rated on a scale of 0 to 100 with 0 referring to no weed suppression and 100 referring to complete weed suppression. Rating values shown for each year represent the mean of three replicates and of two or three evaluations during the growing season from 1999 to 2001. Data were averaged over months of ratings collected during the growing season.

Interestingly, weed density was influenced by the month ratings were performed (F=3.92, p<0.05) as well as fine leaf fescue subspecies (F=10.76, p<0.05). A significant cultivar (F=2.44, p<0.05) by fine leaf fescue subspecies interaction was also present. Among the 78 cultivars evaluated, ten cultivars representing just two subspecies (chewing's and strong creeping) were strongly weed suppressive during 1999-2001, with less than 20 to 30% weed infestation.

Cultivars considered most suppressive included the strong creeping and chewings fescues cultivars 'Sandpiper', 'Shademaster II', 'Intrigue', 'Longefellow II', 'Jamestown II', 'Salsa', 'ABT-CR2', 'ACF 083', 'PST47T', and 'SRX52LAV'. In contrast, weed suppression was poor or unacceptable (greater than 60% weed cover) in plots seeded with the cultivars Rescue 911, a hard fescue, and SR 3200, a blue fescue. The remainder of fine leaf fescue cultivars was rated as intermediate for weed suppressive ability. After establishment, fescues typically spread vegetatively by rhizomes with repeating mowing.

Successful establishment appears to be affected by climatic conditions given the variable responses obtained from 1999-2001. As described previously, vegetative spread was generally favored during the relatively dry year (1999), resulting in greater suppression of weeds. It is also clear that subspecies and cultivar, representing genotypic variation among fescues, are also important factors influencing weed suppressivity over time.

Interestingly, recent laboratory research has shown that several of the fine leaf fescue cultivars used in this study, specifically the chewing's and strong creeping fescues, actively exude root-derived phytochemicals with potent bioherbicidal activity (Bertin et al., "Laboratory Assessment of the Allelopathic Effects of Fine Leaf Fescues," *J. Chem. Ecol.* 29:1919-1937 (2003), which is hereby incorporated by reference in its entirety). The isolation and identification of a single bioactive compound contained in the root exudates of a chewing's fescue, cultivar Intrigue, revealed an amino acid analog, m-tyrosine which is strongly phytotoxic to numerous weedy dicots and monocots encountered in turf settings (Chapter three). It is hypothesized that differences observed in weed suppressive ability among fine fescues are associated not only with their ability to establish quickly and maintain a dense canopy, but also the potential production of allelochemical(s) that actively suppresses competing species. The dynamics of allelochemical production and release into the soil rhizosphere are not well understood. However, it has been observed that chewing's cultivar Intrigue fine leaf fescue seedlings produce up to three-fold higher concentrations of the inhibitor, m-tyrosine, when under drought conditions. The evaluation of weed suppressive ability of fine fescues in several different geographic regions and under varying edaphic conditions is required to clearly determine the importance of cultivar and subspecies upon weed suppression.

Generally, correlations observed between fine fescue weed suppressive ability and quality were not consistent; specifically, certain cultivars with high turfgrass quality ratings; e.g. 'AHF 009' and 'ABT-HF-1' exhibited low weed suppressive ability, whereas cultivars such as Sandpiper with lower turfgrass quality ratings provided strong suppression of weeds. Since turfgrass quality was evaluated only in year one as a measure of color and texture, it is not surprising that this individual rating did not closely correlate with observed long-term growth or suppressive characteristics.

Example 20

Figure 8:
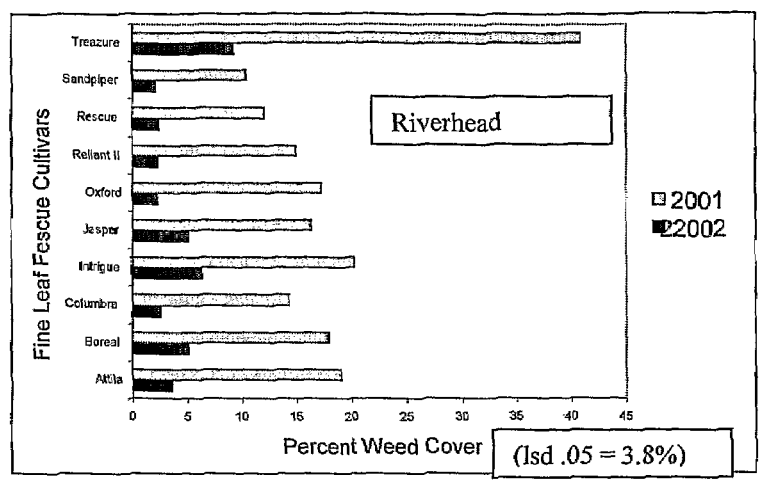
FIG. 8 shows the percentage weed cover in fine leaf fescue plots in Riverhead and Ithaca, N.Y. Values for each year represent the mean of evaluations collected during each growing season.
Figure 8:
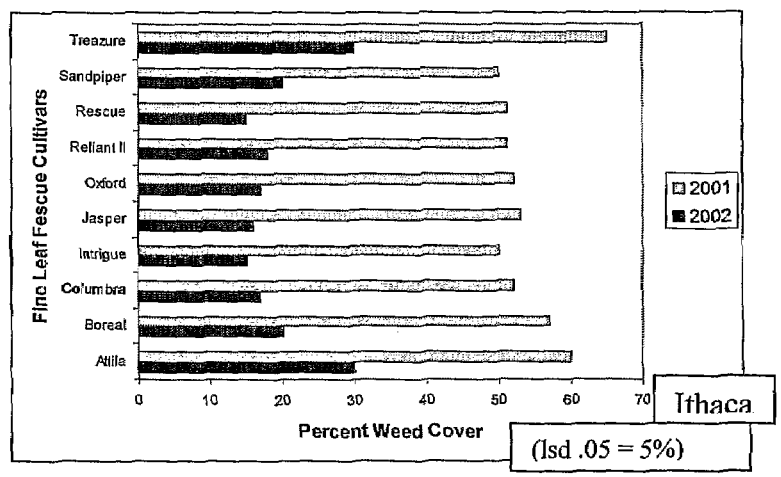

Multi-Location Experiment (FIG. 8)

Given that different individuals performed visual ratings in Ithaca and in Long Island, and variable weed populations existed at each site, the actual percentages of weed coverage data are not compared, but the trends observed in both locations during the two years of study are described. Several fine leaf fescue cultivars were selected for this trial based on the results of the NTEP trial in Ithaca; 'Rescue', 'Columbra', 'Reliant', and 'Intrigue' were included, whereas 'Oxford', 'Attila', 'Jasper', 'Treazure', and 'Sandpiper' which provided a range of weed suppressive ability during 1999-2001.

Edaphic factors differed substantially between the Ithaca and Riverhead, N.Y. sites and may explain some of the variation in responses among these sites. For example, treatments with the cultivar Treazure showed the highest weed densities in Riverhead N.Y., whereas weed densities for other cultivars treatment were not substantially different over the two-year study period (FIG. 8). In 2002, a general reduction in weed abundance was observed for all cultivars; weed infestation levels typically decreased three-fold in 2002, compared with 2001. Similar to Riverhead, no individual cultivar stood out in its weed suppressive ability in Ithaca, N.Y. in 2001 (i.e., all cultivars exhibited 50 to 70% turf coverage with moderate weed infestation). In 2002, however, weed infestation was substantially lower for all cultivars evaluated (15 to 39%). In comparison to 2001 ratings, these findings suggest that the ability of fine leaf fescue cultivars to displace weeds in a field setting is dependent on both the climatic and edaphic site conditions as well as time of establishment. It might be expected that older well-established turfgrass stands would be likely to exhibit greater weed suppression in landscape settings.

Over a two-year period, in Ithaca and Riverhead, N.Y., a strong decrease in weed infestation levels was observed (FIG. 8) with large crabgrass being the principal weed species present in both years.

Example 21

Ithaca Trial 2003 (see Table 3)

In an expanded trial conducted at the Ithaca, N.Y. site using a greater number of replications to detect cultivar differences, the chewing's fescue cultivars 'Intrigue', 'Columbra' and 'Sandpiper' clearly provided the greatest weed suppression in 2003-2005 (Table 5).

TABLE 5

Percentage cover (±St. Dev.) of various fine leaf fescue cultivars established in Ithaca, NY in 2003.

| Fine Leaf Fescue Cultivars | August 2004 | October 2004 | June 2005 |
|---|---|---|---|
| Wilma | 80.8[1] (10.8) a[2] | 84.2 (10.2) ab | 89.8 (7.7) abc |
| Sylvia High | 40.0 (15.4) c | 65.8 (5.4) cd | 70.3 (14.3) d |
| Christina | 80.8 (11.6) a | 83.3 (5.4) ab | 81.6 (7.1) bc |
| RS158 | 57.5 (15.4) b | 67.5 (19.4) cd | 74.6 (10.40 cd |
| Oxford | 74.6 (18.4) a | 74.6 (19.0) bcd | 88.1 (8.6) abc |
| Reliant II | 82.1 (6.6) a | 86.3 (6.1) ab | 93.8 (4.0) a |
| Columbra | 87.1 (10.3) a | 88.2 (6.6) ab | 90.8 (6.1) ab |
| Sunny Green | 80.8 (8.7) a | 81.3 (4.8) abc | 81.0 (5.9) bc |
| Rescue 911 | 77.1 (12.1) a | 81.3 (13.3) abc | 85.3 (7.1) abc |
| Sandpiper | 85 (8.8) a | 87.5 (6.6) ab | 89.8 (5.5) abc |
| Intrigue | 88.8 (5.7) a | 89.2 (4.7) a | 94.7 (5.4) a |
| Tukey's HSD | 15.31 | 14.41 | 10.14 |

[1]Values represent the mean of 12 replications for each cultivar.
[2]letters within a column that are the same are not significantly different at the p > 0.05 level of significance according to the Tukey's HSD test.

Of the ten cultivars evaluated, two main groupings were observed; those cultivars that provided greater than 85% coverage or less than 15% weed infestation ('Intrigue', 'Columbra', 'Sandpiper', and 'Reliant II') and those that provided less than 75% coverage of plots or greater than 25-30% infestation ('Sylvia High', 'RS158'). This experiment confirmed earlier findings observed in the NTEP trial and laboratory experiments (Bertin et al., "Laboratory Assessment of the Allelopathic Effects of Fine Leaf Fescues," *J. Chem. Ecol.* 29:1919-1937 (2003), which is hereby incorporated by reference in its entirety) that certain cultivars possessed the ability to suppress weeds under both field and laboratory conditions. Weed suppressive cultivars included chewings fescues 'Intrigue', 'Columbra', 'Sandpiper', and hard fescue cultivar 'Reliant II', which were also observed to be most inhibitory in laboratory experiments evaluating inhibition of weed seedling growth in several bioassays (Bertin et al., "Laboratory Assessment of the Allelopathic Effects of Fine Leaf Fescues," *J. Chem. Ecol.* 29:1919-1937 (2003), which is hereby incorporated by reference in its entirety). It is possible that the reduced weed suppressive ability observed in the two European cultivars, 'RS158' and 'Sylvia High', in 2004-2005 was associated with their inability to adapt to warmer, continental growing conditions encountered in Ithaca, N.Y. as compared with those of cooler conditions in Scandinavia in Northern Europe, where they were judged to be exceptional performers.

Enhanced weed suppressive ability of fine fescue cultivars may be attributed to the innate ability of certain fescues to compete more efficiently with weeds. A well established dense turf generally leads to lower weed densities and fewer weed management problems (Turgeon, A. J., "Turfgrass Management," 5th Ed., Upper Saddle River, N.J.: Pearson Prentice Hall, 392 p. (1999), which is hereby incorporated by reference in its entirety). Certain cultivars consistently produced dense, well-established stands within 12 to 18 months after seeding in NY locations. All fine leaf fescues were generally more weed suppressive in their second and third growing seasons after establishment. This may be due to denser canopy formation which results in greater weed suppression and competition with weed seedlings, or the potential of certain cultivars to release greater levels of allelochemicals when well established. Recent laboratory trials have shown that even two-week-old chewing's fescue seedlings can produce approximately 1 mg of root exudates per gram of fresh root weight, when grown under soil-free conditions (Bertin et al., "Further Evaluation of the Allelopathic Potential of Fine Leaf Fescue," *Proc WSSA* 56:116 (2002), which is hereby incorporated by reference in its entirety). This represents a significant output of secondary products through the root exudation process.

Although turf density as well as the potential production of allelochemicals inhibitory to weed seedling germination and growth may vary with turf maturity, early suppression of weed growth and enhanced biomass production is clearly important in newly established stands due to competitive advantages allowing for reduced weed infestation during the critical period of turfgrass establishment. Fescues are known to be particularly slow to establish in comparison to other turfgrasses (Turgeon, A. J., "Turfgrass Management," 5th Ed., Upper Saddle River, N.J.: Pearson Prentice Hall, 392 p. (1999), which is hereby incorporated by reference in its entirety). Any evolutionary adaptation leading to enhanced competitiveness during the critical period of turf establishment including enhanced growth rates, or allelochemical production resulting in enhanced weed suppression, may lead to greater reproductive fitness over time. It appears from our laboratory evaluations that certain chewings and strong creeping fescues, as well as Arizona fescue produce significant levels of allelochemicals from their living root systems.

Several of these cultivars also exhibited strong weed suppressive tendencies in field experiments. Additional studies monitoring rate of biomass production after establishment, turf density, and potential allelochemical production over time in various field settings would be valuable in furthering our understanding of the factors contributing to differential weed suppression by fine leaf fescue cultivars over time.

Example 22 m-Tyrosine, an Amino-Acid Bioherbicide Isolated From Root Exudates of Fescue Grasses Examples 22-37 (herein) are related to the study of m-tyrosine, an amino acid bioherbicide isolated from root exudates of fescue grasses. Fescue grasses displace neighboring plants by depositing large quantities of a phytotoxic root exudate in the soil rhizosphere. Via activity-guided fractionation, we have isolated and identified the amino acid m-tyrosine as the major active component. While m-tyrosine is strongly phytotoxic, its structural isomers o- and p-tyrosine exhibit no toxicity. We show that m-tyrosine exposure results in growth inhibition for a wide range of plant species and propose that this non-protein amino acid may interfere with cell wall formation or may act as an antagonist of auxin (IAA). The discovery of m-tyrosine as a broad-spectrum bioherbicide could lead to the development of unique, sustainable weed management strategies.

Example 23

Figure 9:
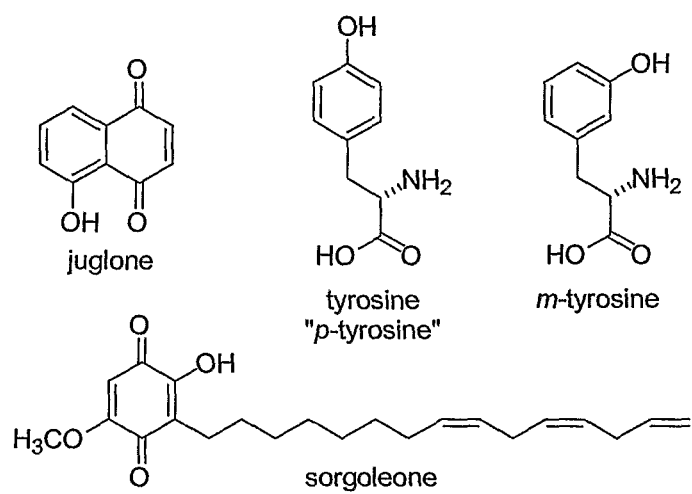
FIG. 9 shows the structures of juglone, sorgoleone, the proteinogenic amino acid tyrosine, and its isomer, m-tyrosine.

Introduction: m-Tyrosine, an Amino-Acid Bioherbicide Isolated From Root Exudates of Fescue Grasses Secondary metabolites are of central importance in plant-plant and plant-microbial interactions. Secondary products released in plant root exudates are often associated with the development of competitive advantages through allelopathy (Bais et al., "Allelopathy and Exotic Plant Invasion: From Molecules and Genes to Species Interactions," *Science* 301: 1377 (2003), which is hereby incorporated by reference in its entirety). Juglone, a highly phytotoxic naphthoquinone produced by black walnut (*Juglans nigra* L.), and sorgoleone, a substituted quinone from sorghum (*Sorghum* spp.), are two classical examples of potently active allelochemicals deposited via the plant's living root system (Bertin et al., "The Role of Root Exudates and Allelochemicals in the Rhyzosphere," *Plant and Soil* 256:67-83 (2003); Bertin et al., "Laboratory Assessment of the Allelopathic Effects of Fine Leaf Fescues," *J. Chem. Ecol.* 29:1919-1937 (2003), which are hereby incorporated by reference in their entirety) (FIG. 9). Structural elucidation and mode-of-action of novel root-derived phytotoxins could yield important clues for the development of biorational approaches to pest control. As described in Examples 22-37, isolation, identification, and biological activity of a potent, structurally unprecedented broad-spectrum phytotoxin exuded by the roots of fine leaf fescue grasses (*Festuca* spp.), specifically, m-tyrosine, a non-protein isomer of the common amino acid tyrosine.

Figure 10:
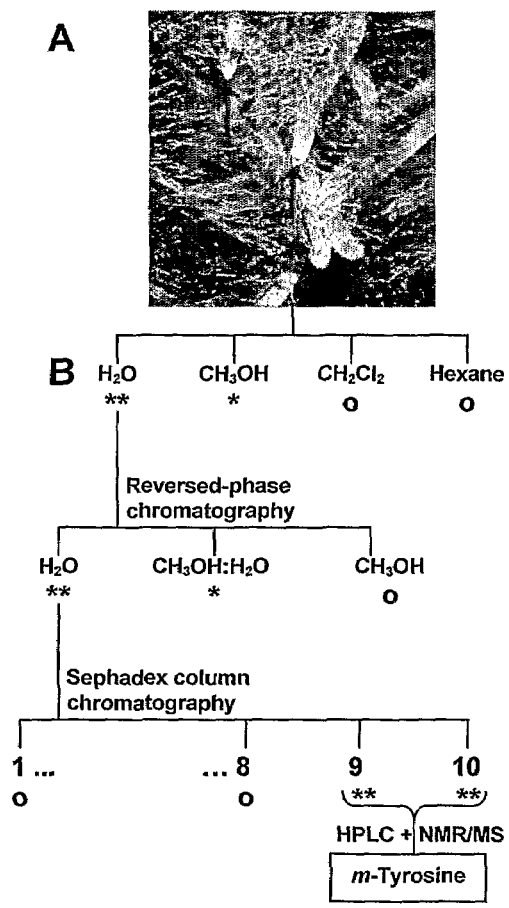
FIGS. 10A and 10B show *F. rubra rubra* cv. Intrigue roots (FIG. 10A) and activity-guided fraction of cv. Intrigue root exudates (FIG. 10B). The yellowish discoloration at the root tips (arrows) indicates accumulation of root exudates on actively growing roots (FIG. 10A). Fractions are classified as strongly active (**), slightly active (*), and inactive (o) in the phytotoxicity assay.

Fescue grasses constitute a diverse family of grasses, whose stress tolerance and disease resistance have resulted in their use in landscape, roadside, and pasture settings as well as for conservation purposes (Ruemmele et al., "Fine Leaf Fescue Germplasm Diversity and Vulnerability," *Crop Sci.* 35:313-316 (1985), which is hereby incorporated by reference in its entirety). The unusual ability of many fine fescue species to out-compete other plants in previous investigations suggested that fescue root exudates have phytotoxic properties (Bertin et al., "The Role of Root Exudates and Allelochemicals in the Rhyzosphere," *Plant and Soil* 256:67-83 (2003); Bertin et al., "Laboratory Assessment of the Allelopathic Effects of Fine Leaf Fescues," *J. Chem. Ecol.* 29:1919-1937 (2003), which are hereby incorporated by reference in their entirety). In the initial field evaluation of 80 different fine fescue cultivars, a group of eight cultivars with strong weed suppressive potential were identified. Based on these results, "Intrigue", a common chewing's fescue cultivar that showed particularly strong weed suppression, was selected for further studies (Bertin et al., "The Role of Root Exudates and Allelochemicals in the Rhyzosphere," *Plant and Soil* 256:67-83 (2003); Bertin et al., "Laboratory Assessment of the Allelopathic Effects of Fine Leaf Fescues," *J. Chem. Ecol.* 29:1919-1937 (2003), which are hereby incorporated by reference in their entirety). In order to identify the allelopathic compound(s) contained in "Intrigue" root exudates, an activity-guided separation scheme was developed based on a simple and reliable Petri-dish assay monitoring inhibition of radicle elongation in lettuce seedlings (*Lactuca sativa* L.). Using this assay, the phytotoxic activity of hexanes, dichloromethane, methanol, and water extracts of roots of two-week old Intrigue seedlings grown under soil-free conditions on a capillary mat were compared. The aqueous extract clearly showed the strongest inhibition of lettuce root growth and was thus selected for further fractionation (FIG. 10). For this purpose, the crude aqueous root extract was submitted to reversed-phase column chromatography on $C_{18}$-coated silica gel. The most active fraction obtained from the reversed-phase chromatography was further fractionated by size-exclusion chromatography using Sephadex LH20 beads, again monitoring activity via the Petri-dish assay. The resulting active fraction consisted of more than 80% of one major component, which was characterized without any additional purification via a standard set of two-dimensional NMR spectra, including double-quantum filtered correlation spectra (dqf-COSY), ($^1$H, $^{13}$C)-heteronuclear multiple-quantum correlation spectra (HMQC), and ($^1$H, $^{13}$C)-heteronuclear multiple-bond correlation spectra (HMBC) (Taggi et al., "A New Approach to Natural Products Discovery Exemplified by the Identification of Sulfated Nucleosides in Spider Venom," *J. Am. Chem. Soc.* 126(33):10364-10369 (2004), which is hereby incorporated by reference in its entirety). The NMR-spectroscopic data suggested a 3'-substituted phenylalanine derivative as the structure of the major component.

Additional analyses using high-resolution positive-ion electrospray mass spectrometry yielded a molecular formula of $C_9H_{11}NO_3$. In combination with the results from ultraviolet and infrared spectroscopic analysis, these data indicated that 3-hydroxyphenylalanine, commonly known as m-tyrosine, constituted the major component of the active fraction isolated from the root exudates. This structural assignment was confirmed via an NMR-spectroscopic mixing experiment whereby a small amount of synthetic m-tyrosine was added to the isolated active fraction (Schroeder et al., "Chiral Silylation Reagents: Determining Configuration via NMR-Spectroscopic Coanalysis," *Org. Lett.* 6(18):3019-3022 (2004), which is hereby incorporated by reference in its entirety). Finally, the absolute configuration of the isolated m-tyrosine was determined to be L by means of an NMR-spectroscopic comparison of its (S)-methoxytrifluoromethylphenylacetic acid ((S)-MTPA) derivative with the (R)- and (S)-MTPA derivatives of synthetic m-tyrosine (Evans et al., *J. A. Chem. Soc.* 112:4011-4030 (1990), which is hereby incorporated by reference in its entirety).

Figure 11:
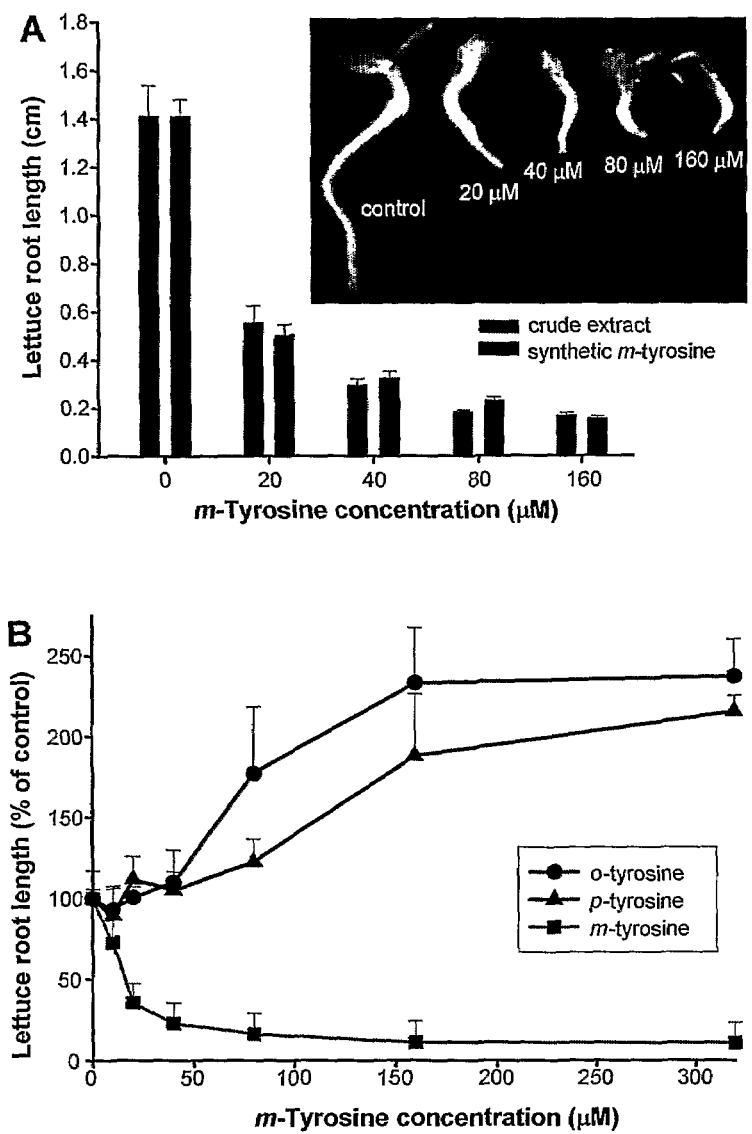
FIGS. 11A and 11B show a comparison of the effect of fescue cv. Intrigue aqueous root extract and authentic m-tyrosine on lettuce (*Lactuca sativa*) seedling root growth (FIG. 11A) and the effect of o-, m-, and p-tyrosine on lettuce seedling radicle elongation (FIG. 11B). Insert (of FIG. 11A): photographs of lettuce seedlings exposed to various concentrations of root extract, showing stunted growth and discoloration of root tips. Lettuce seeds were grown for 72 h in the presence of various concentrations of the three tyrosine isomers. Data represent means of root lengths of 90 seedlings each.

HPLC analyses of cv. Intrigue aqueous root extracts indicated an m-tyrosine content of 33-43% of the root extract dry weight. In order to determine whether the phytotoxicity of the fine fescue root exudate was in fact attributable to the presence of m-tyrosine, the activity of the aqueous root extract was compared to that of aqueous solutions of authentic m-tyrosine. Using an array of concentrations of dried root extract and m-tyrosine, nearly identical dose-response curves were obtained, indicating that 1-tyrosine accounted for the majority of observed toxicity in our assay (FIG. 11). Root elongation of lettuce seedlings was reduced by 64% when exposed to 20 µM concentrations of m-tyrosine loaded on filter paper. At this concentration, visual inspection of the root tip revealed necrosis and stunting (FIG. 11A). A 50% reduction of root growth was observed for concentrations as low as 17 µM, as tested on lettuce seedlings at 72 h. m-Tyrosine phytotoxicity as measured in this assay is similar to that of other potently active allelochemicals including juglone ($I_{50}$: between 10 and 100 µM) and sorgoleone ($I_{50}$: between 10 µM and 200 µM).

Interestingly, the common amino acid tyrosine, "p-tyrosine", and 2'-hydroxyphenylalanine, "o-tyrosine", were not phytotoxic. In fact, results show that lettuce seedling growth is stimulated by o- or p-tyrosine at concentrations as low as 50 µM (FIG. 11B). In addition, m-tyrosine was evaluated for potential autotoxicity to fine leaf fescue itself, using the cultivar Intrigue, as a potent producer of m-tyrosine. Root elongation of fescue seedlings was not affected by the addition of synthetic m-tyrosine at the range of concentrations evaluated (20 µM to 160 µM).

To determine how widespread m-tyrosine production is within the genus *Festuca*, a series of fine leaf fescues and related species were screened for the presence of this phytotoxin in their respective root exudates. HPLC analyses of the aqueous root extracts showed that Arizona fescue (*Festuca arizona*), all creeping red fescue (*Festuca rubra* L. *rubra*) and chewing's fescue (*Festuca rubra commutata*) cultivars produced significant quantities of m-tyrosine, whereas several other fescue and grass species did not. Quantitative HPLC analysis of aqueous root extracts from two-week old fescue seedlings (cv. Intrigue) indicated that m-tyrosine was produced at a rate of approximately 72 µg per gram root fresh weight, which corresponded to 6.4 mg per gram of dried roots. As secondary metabolite production is often highly dependent on plant age and environmental factors (Reigosa et al., "Stress in Allelopathy," in Reigosa et al. Eds., *Allelopathy, from Molecules to Ecosystems*, Enfield, N.H.: Science Publishers (2002), which is hereby incorporated by reference in its entirety), the absolute amounts of m-tyrosine produced by the various fescue species and cultivars undoubtedly vary in response to changes in growing conditions.

Figure 12:
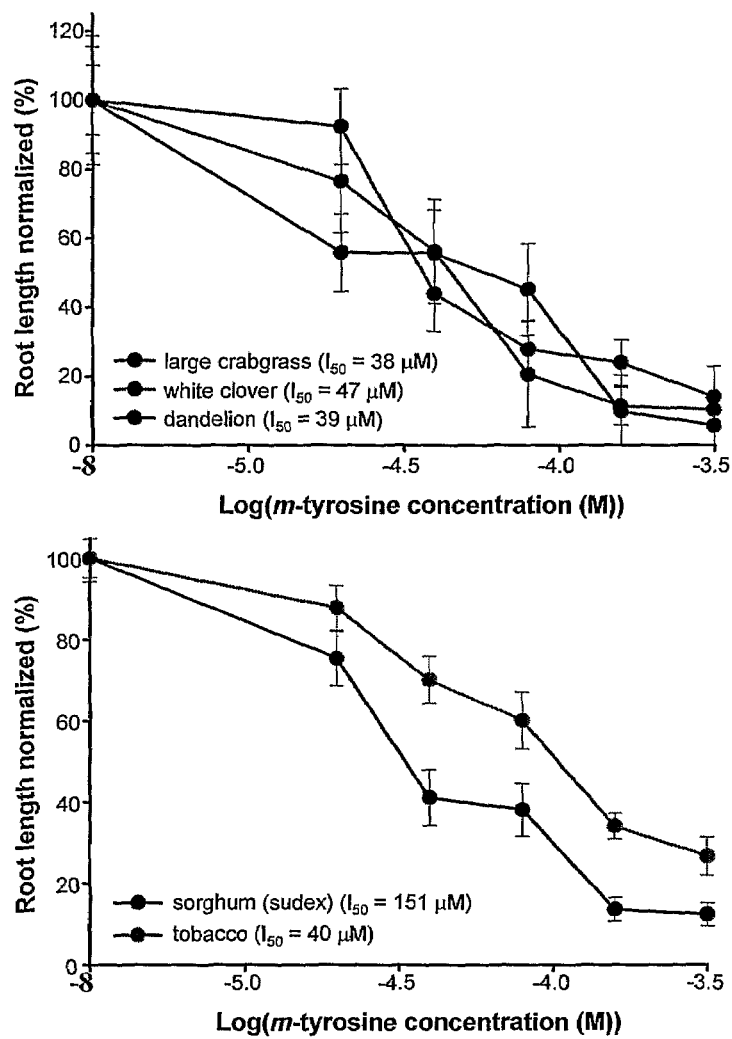
FIG. 12 shows the effect of m-tyrosine on seedling radicle elongation for several common weed and crop species. Data represent means of root lengths of 90 seedlings.

Because previous studies suggested that the presence of fine leaf fescue may impact growth of a wide range of plant species (Hively et al., "Interseeding Cover Crops into Soybean and Subsequent Corn Yields" *Agron. J.* 93:308-313 (2001), which is hereby incorporated by reference in its entirety), the susceptibility of selected monocot and dicot plants to m-tyrosine exposure were explored (FIG. 12). Seedling growth of all plants exposed to m-tyrosine was markedly reduced, and the concentration of m-tyrosine required to observe 50% inhibition of radicle elongation ranged between 10 and 260 µM. Root growth of both lettuce and crabgrass seedlings was similarly suppressed in soil media amended with various amounts of m-tyrosine, as was shown in a series of soil experiments using a field soil and a commercial growth media based on peat moss.

Root elongation of lettuce and crabgrass seedlings was reduced by 50% at concentrations as low as 4 mM. Because activity of allelochemicals and herbicides in the soil is greatly influenced by environment and soil type (Kobayashi, K., "Factors Affecting Phytotoxic Activity of Allelochemicals in Soil," *Weed Biol. Man.* 4:1-7 (2004), which is hereby incorporated by reference in its entirety), comparing these results to the activity of synthetic herbicides is difficult, and accurate predictions of the behavior and dynamics of m-tyrosine in the rhizosphere on the basis of laboratory experiments alone are not possible (Inderjit et al., "Are Laboratory Bioassays for Allelopathy Suitable for Prediction of Field Responses?," *J. Chem. Ecol.* 26:2111-2118 (2000), which is hereby incorporated by reference in its entirety). Of particular interest in this context is m-tyrosine's impact on growth and establishment of rhizosphere microbiota. In antibacterial assays with m-tyrosine, growth of *Escherichia coli, Bacillus cereus*, and *Bacillus subtilis* was not inhibited. Similarly, cultures of the fungus *Metarhizium anisopliae* (Metsch.) were not sensitive to m-tyrosine, even at concentrations as high as 25 mM, indicating that the mode of action of m-tyrosine appears to be plant specific. Certain phytotoxins, for example 1-8, cineole (Romagni et al., "Allelpathic Effects of Volatile Cineoles on Two Weedly Plant Species," *J. Chem. Ecol.* 26:303-313 (2000), which is hereby incorporated by reference in its entirety) and avarol (Muller et al., "Avarol, a Cytostatically Active Compound from the Marine Sponge *Dysidea Avara*," *Comp. Biochem. Physiol. C.* 80:47-52 (1985), which is hereby incorporated by reference in its entirety), inhibit plant growth and development by directly affecting cell division (Hess, F. D., "Herbicide Effects on the Cell Cycle of Meristematic Plant Cells" *Rev. Weed Sci* 3:183-201 (1987), which is hereby incorporated by reference in its entirety). Chromosome staining in dividing onion (*Allium cepa* L.) root cells clearly showed that m-tyrosine at 20 µM significantly reduced the mitotic indices in all phases of mitosis. However, m-tyrosine may not affect mitosis per se, as the relative number of prometaphase figures to increase significantly with treatment as has been reported for other mitotic inhibitors (Lehnen et al., "The Herbicide Sindone B Disrupts Spindle Microtubule Organizing Centers Pestic," *Biochem. Phys.* 44:50-59 (1992), which is hereby incorporated by reference in its entirety) was not observed.

Considering its chemical structure and the symptomology observed after treatment, it appears likely that m-tyrosine interferes with cell wall formation rather than mitosis. m-Tyrosine could interfere with cell-wall formation by impacting cross-linking of the extensins, a major group of cell wall proteins which confer strength within the cell wall (Showalter, A. M., "Structure and Function of Plant Cell Wall Proteins," *Plant Cell* 5:9-23 (1993), which is hereby incorporated by reference in its entirety). During cell growth, extensin molecules form covalent networks in the cell wall, which are based on cross-linked p-tyrosine moieties (Brady et al., "Di-isodityrosine, a Novel Tetrameric Derivative of Tyrosine in Plant Cell Wall Proteins: A New Potential Cross-Link," *Biochem. J.* 315:323-327 (1996), which is hereby incorporated by reference in its entirety). It is possible that incorporation of m-tyrosine during cell wall formation in place of either p-tyrosine or phenylalanine interferes with cross-linking. In addition, m-tyrosine could interfere with the biosynthesis of lignin building blocks such as p-coumaric acid, which is produced either from tyrosine or directly from phenylalanine (Neish A. C., "Formation of m- and p-Coumaric Acids by Enzymatic Deamination of the Corresponding Isomers of Tyrosine," *Phytochemistry* 1:1-24 (1961), which is hereby incorporated by reference in its entirety).

Additional studies are needed to establish the exact mode of action of m-tyrosine on plant cell growth; however, the results presented herein suggest that its mode of action is different from that of other root-deposited allelochemicals such as juglone and sorgoleone, which appear to interfere directly with photosynthesis and other redox processes in the plant cell or cell membranes (Hejl et al., "Juglone Disrupts Root Plasma Membrane $H^+$-ATPase Activity and Impairs Water Uptake, Root Respiration, and Growth in Soybean (*Glycine max*) and Corn (*Zea mays*)," *J. Chem. Ecol.* 30:453-471 (2004), Gonzalez et al., "Inhibition of a Photosystem II Electron Transfer Reaction by the Natural Product Sorgoleone," *J. Agr. Food Chem.* 45:1415-1421 (1997), which are hereby incorporated by reference in their entirety). The structures of both juglone and sorgoleone contain a quinonoid system, and their phytotoxicity appears to be directly related to the chemical properties of this structural feature (Rietveld W. J., "Allelopathic Effects of Juglone on Germination and Growth of Several Herbaceous and Woody Species," *J. Chem. Ecol.* 9:295-307 (1983); Neish A. C., "Formation of m- and p-Coumaric Acids by Enzymatic Deamination of the Corresponding Isomers of Tyrosine," *Phytochemistry* 1:1-24 (1961), which are hereby incorporated by reference in their entirety). It should be noted that while m-tyrosine might conceivably act as a biosynthetic precursor of a quinonoid amino acid mimicking juglone or sorgoleone, this possibility is rendered unlikely by the observation that o-tyrosine, which could serve as precursor for the same quinone, is devoid of herbicidal activity. Also, similar quinonoid structures within fescue root exudates were not observed.

In summary, the results show that certain fescue grasses produce large amounts of m-tyrosine in their root exudates, and that this non-protein amino acid functions as a broad-spectrum phytotoxin with an unusual mode of action. m-Tyrosine had been identified previously in only one higher plant species, as a component in the foliage of *Euphorbia myrsinites* L. (Mothes et al., "m-Tyrosin, Eine Neue Aminosaure Aus Dem Milchsaft von *Euphorbia Myrsinites*," *L Z. Naturforsch* 19b:1161-1162 (1964), which is hereby incorporated by reference in its entirety), although its biological function in *Euphorbia* remains unknown. It seems surprising that the copious production of such a close structural analogue of one of the basic amino acids, as well as its pronounced phytotoxic properties, have not been discovered earlier.

Example 24

Plant Material and Chemicals

Fine leaf fescue seeds were obtained from several turfgrass companies, including Scott's and Turf Merchants, Inc. Intrigue seeds were donated by Preferred Seed Company, Inc., New York. Lettuce (*Lactuca sativa* L.) seeds were purchased from Johnny's Selected Seed, Me. Weed species used in the phytotoxicity bioassays included (*Arabidopsis thaliana* L., dandelion (*Taraxacum officinale* Weber in Wiggers), large crabgrass (*Digitaria sanguinalis* L.), black medic (*Medicago lupulina* L.), cress (*Lepidium sativum* L.), barnyardgrass (*Echinochloa crus-galli* (L.) Beauv.), annual bluegrass (*Poa annua* L.), birdsfoot trefoil (*Lotus corniculatus* L.), broadleaf plantain (*Plantago major* L.), mouseear chickweed (*Cerastium vulgatum* L.), common chickweed (*Stellaria media* L), velvetleaf (*Abutilon theophrasti* Medicus), purslane (*Portulaca oleracea* L.), white clover (*Trifolium repens* L.). Weed seeds were purchased from Herbiseed, England. All seeds used for Petri dishes bioassays were surfaced sterilized by being suspended for 1 minute in a 1:1 ethanol water solution. Subsequently, seeds were rinsed three times with distilled water and used immediately in the bioassays. DL m-tyrosine was obtained from Sigma-Aldrich (St. Louis, Mo.), while a sample of L-m-tyrosine was kindly donated by Albany Molecular Research, Inc. All other chemicals and solvents were obtained from Sigma-Aldrich Corporation.

Example 25

Extraction of Fine Leaf Fescue Roots

Approximately 50 g of sterilized fine leaf fescue seeds were placed between two layers of wet cheesecloth (40×50 cm) arranged on a capillary mat system as described in (Czarnota, M. A. Thesis, Cornell University (2001), which is hereby incorporated by reference in its entirety). After 14 days, the roots were harvested by separation from the adjacent screen with a razor blade. Collected fresh root tissue was extracted for 15 minutes with either 200 ml of hexanes, 200 ml of methanol, 200 ml dichloromethane, or 200 ml of water. After filtration, the extracts were evaporated to dryness in vacuo using a rotary evaporator, at ambient temperature. The dried root exudates extracts were weighed and then stored at −20° C. until further use.

Example 26

Petri-Dish Bioassay to Assess Phytotoxic Activity of Root Extracts

Each root extract (hexanes, dichloromethane, methanol, and water extract) was subjected to a Petri dish bioassay as follows. For each root extract, four Petri dishes each equipped with one Whatman #1 filter paper were used. The Petri dishes were treated with 1.0 ml of a solution consisting of 0.125, 0.25, 0.5, and 1.0 mg of root extract per ml of the solvent used for extraction of the roots. To avoid skewing of the results by toxic effects of the solvents, filter papers treated with hexanes, methanol, and methylene chloride root extract solutions were placed in the hood for 1 h to allow complete evaporation of the solvents. Subsequently, 1.0 ml of water was added to each of the filter papers now impregnated with hexanes, methylene chloride, or methanol root extracts. For each series of bioassays, two controls were run. One control consisted of a Petri dish with filter paper to which 1.0 ml of pure water was added. The second control consisted of a Petri dish containing a filter paper treated with 1.0 ml of the respective root extraction solvent, which was subsequently evaporated, followed by the addition of 1.0 ml of water.

Ten surface-sterilized lettuce seeds were placed on the moist paper filter in each Petri dish. After five days in a controlled environment (light regime of 45.33 µmol photons $m^{-2}$ $s^{-1}$ at temperature of 25° C.), radicle and shoot length were measured and compared to those of control plants.

Example 27

Fractionation of Aqueous Root Extract and Chemical Analysis

Figure 13:
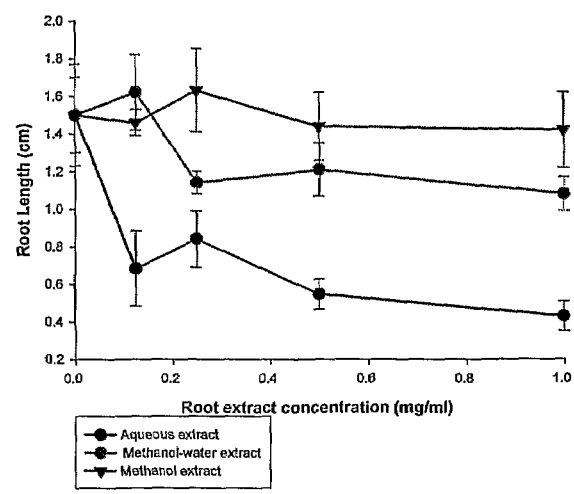
FIG. 13 shows a comparison of the phytotoxicity of root exudate extracts on lettuce seedlings.
Figure 14:
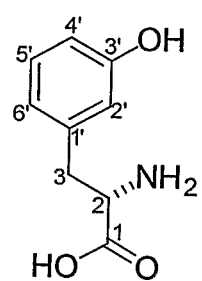
FIG. 14 shows the structure of m-tyrosine (3'-hydroxyphenylalanine) and atom numbering.
Figure 15:
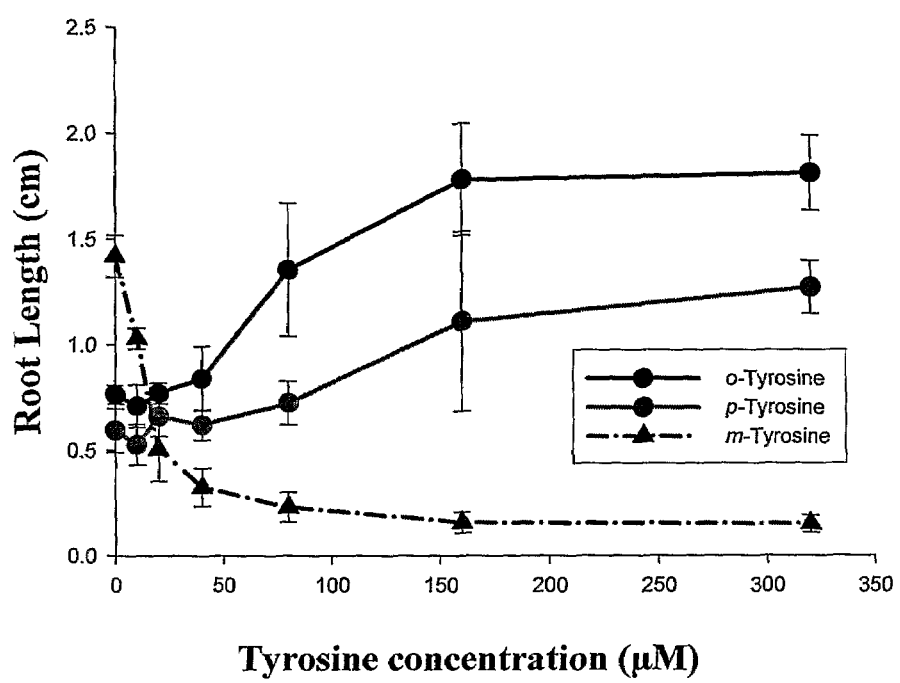
FIG. 15 shows an assessment of potential phytotoxicity of o-, m- and p-tyrosine.
Figure 16:
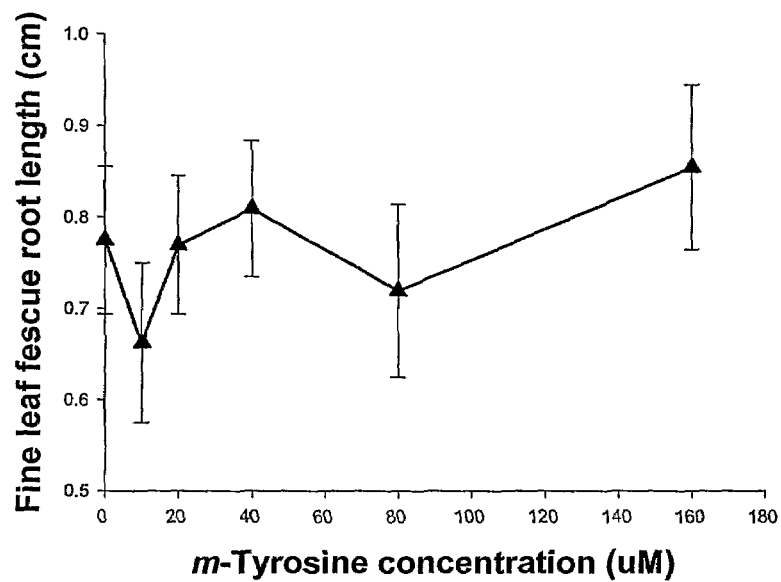
FIG. 16 shows the effect of synthetic m-tyrosine on root elongation of fine leaf fescue seedlings cultivar Intrigue.
Figure 17:
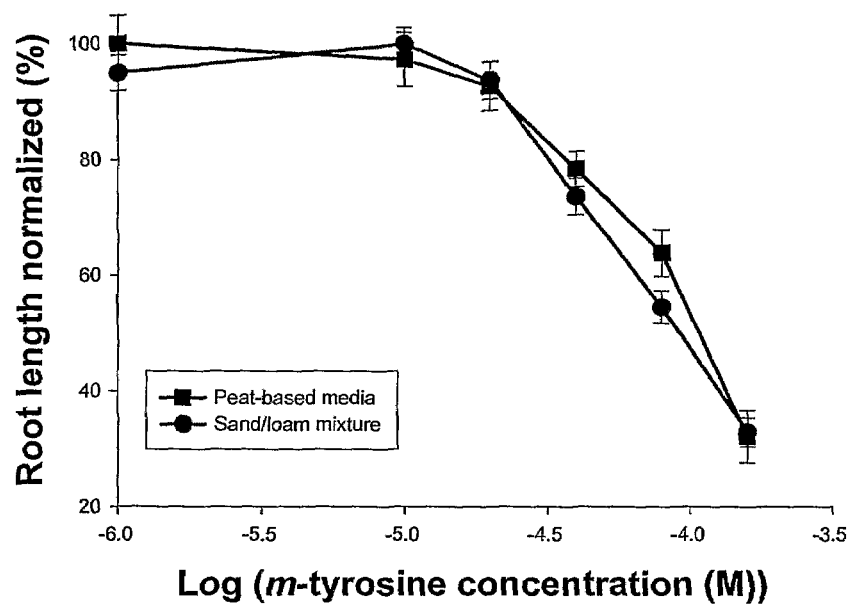
FIG. 17 shows an assessment of m-tyrosine phytotoxic activity in soil media (peat-based and sand/loam mixture media).

The crude aqueous root exudate was submitted to reversed-phase column chromatography on $C_{18}$-coated silica gel, using a methanol-water solvent gradient for elution, and increasing the methanol content from 0% to 100%. Three fractions were collected and subjected to the Petri-dish bioassay described above (FIG. 13).

The aqueous fraction, which showed by far the strongest toxicity, was subjected to size-exclusion column chromatography on Sephadex LH20, using a 1:1 mixture of methanol and water as solvent. Ten fractions were collected, which were evaporated separately and then and submitted to $^1$H NMR spectroscopic analysis using a 600 MHz Varian INOVA spectrometer. Fractions with similar $^1$H NMR spectroscopic profiles were combined, which resulted in four fractions that were tested in the Petri-dish bioassay. One single fraction showed strong phytotoxic activity, while the other three fractions were not active. The active fraction was subjected to a series of two-dimensional NMR-spectroscopic experiments, including phase-sensitive double-quantum filtered correlation spectroscopy (dqf-COSY), heteronuclear multiple-quantum correlation spectroscopy (HMQC), and heteronuclear multiple-bond correlation (HMBC). Following NMR-spectroscopic analysis, the sample was subjected to mass spectrometry, using a Micromass Quattro I tandem mass spectrometer operated in positive-ion electrospray mode with direct infusion of the sample dissolved in a 50:50 (v/v) solution of methanol and water containing 1% formic acid. Molecular mass calculated for $C_9H_{12}NO_3^+$ (M+H$^+$): m/z 182.07. found: m/z 182.07.

Example 28

Determination of the Absolute Configuration of Fescue-Produced m-Tyrosine

Reference samples of the (S)- and (R)-2-methoxy-2-trifluoromethyl-2-phenylacetic acid ((S)- and (R)-MTPA) derivatives of L-3'-hydroxyphenylalanine were prepared as follows. To a well-stirred solution of 0.5 mg of L-3'-hydroxyphenylalanine in 0.5 ml of water at 0° C. were added 0.5 ml of aqueous NaHCO$_3$-solution, 1 ml of acetone, and 4 µl of either (R)- or (S)-2-methoxy-2-trifluoromethyl-2-phenylacetic acid chloride ((R)- and (S)-MTPA-Cl). The resulting mixture was stirred for 1 h at 20° C. Subsequently, the acetone was evaporated in vacuo using a rotary evaporator, and the aqueous residue was extracted with 1 ml of ether. The organic extract was filtered over a pad of anhydrous Na$_2$SO$_4$ and evaporated to dryness in vacuo. The residue was dissolved in 0.6 ml of acetone-d$_6$ and the resulting solution analyzed by $^1$H-NMR spectroscopy. The diastereomeric (S)- and (R)-MTPA derivatives of L-3'-hydroxyphenylalanine showed significant differences in their $^1$H-NMR spectra. Characteristic signals include protons 3-H$_\alpha$ and 3-H$_\beta$ ((R)-MTPA derivative [from (S)-MTPA-Cl] δ 3.09 ppm and 3.24 ppm; (S)-MTPA derivative [from (R)-MTPA-Cl] δ 3.02 ppm and 3.19 ppm). Subsequently, a portion of fescue-produced m-tyrosine (isolated from the aqueous fescue root extract) was reacted with (R)-MTPA-Cl in the same manner as described above. NMR spectroscopic analysis of the resulting (S)-MTPA derivative produced an $^1$H-NMR spectrum showing signals for protons 3-H$_\alpha$ and 3-H$_\beta$ at 3.02 ppm and 3.19 ppm, indicating that the root exudate fraction contained the L-isomer of 3'-hydroxyphenylalanine (m-tyrosine).

TABLE 6

NMR-spectroscopic data of the major component in the active Sephadex fraction (600 MHz for $^1$H, 126 MHz for $^{13}$C, solvent D$_2$O).

| Carbon No. | δ, ppm | Proton No. | δ, ppm | J, Hz | NOESY Correlations | HMBC Correlations |
|---|---|---|---|---|---|---|
| C-1 | 174.1 | | | | | |
| C-2 | 56.0 | 2-H | 3.99 | $J_{3\alpha,2}$ = 8.4, $J_{3\beta,2}$ = 4.3 | | C-1, C-3, C-1' |
| C-3 | 36.4 | 3-H$_\alpha$ | 3.08 | $J_{3\alpha,3\beta}$ = 14.7 | 2'-H, 6'-H | C-1, C-2, C-1', C-2', C-6' |
| | | 3-H$_\beta$ | 3.25 | | 2'-H, 6'-H | C-1, C-2, C-1', C-2', C-6' |
| C-1' | 137.2 | | | $J_{4,5}$ = 2 | | |
| C-2' | 116.2 | 2'-H | 6.83 | $J_{2',4'}$ = 1.5, $J_{2',6'}$ = 1 | 3-H$_\alpha$, 3-H$_\beta$ | C-3, C-4', C-6' |
| C-3' | 156.1 | | | | | |
| C-4' | 114.7 | 4'-H | 6.87 | $J_{4',5'}$ = 8.4 | | C-2', C-6' |
| C-5' | 130.7 | 5'-H | 7.31 | $J_{5',6'}$ = 7.8 | | C-3',C-1' |
| C-6' | 121.6 | 6'-H | 6.89 | | 3-H$_\alpha$, 3-H$_\beta$ | C-3, C-2', C-4' |

Example 29

Determination of m-Tyrosine Concentration in Fescue Root Exudate

The amounts of m-tyrosine contained in the aqueous fescue root exudate extracts and in active fractions originating from our fractionation scheme were determined by HPLC analysis, using an Agilent 1100 HPLC system equipped with a diode-array detector and a Supelco RP-18 Discovery column (length: 250 mm, diameter 10 mm), which was eluted with methanol-water mixtures (starting with a mixture of 3% methanol, 67% water, and 30% of 0.05% aqueous trifluoroacetic acid for an initial period of 3 min, followed by a linear gradient reaching 50% methanol, 20% water and 30% of 0.05% aqueous trifluoroacetic acid at 30 min, at a constant flow of 3.4 ml/min). In preparation for HPLC analysis, aqueous extracts of fine leaf fescue root exudates were evaporated to dryness, and the residue was reconstituted at a concentration of 13 mg root exudate per ml of water. Monitoring absorption at 280 nm, peaks at 12.7 minutes were integrated and compared against a calibration curve obtained from a series of aqueous dilutions of commercial m-tyrosine.

Example 30

Comparison of Phytotoxic Activity of M-Tyrosine with that of Root Exudate

To each of a series of Whatman #1 filter paper sheets was added 1.0 ml of an aqueous solution of commercial m-tyrosine at concentrations of 10, 20, 40, 80, and 160 µM or 1.0 ml of an aqueous solution of dried Intrigue root exudate adjusted to contain m-tyrosine at identical concentrations, as determined via HPLC. Ten seeds of either lettuce or crabgrass were placed on top of each of the filter papers. After several days of germination (5 days for lettuce, 7 days for crabgrass), root and shoot length were measured and compared to the root and shoot length lengths of control plants grown under identical conditions, but using 1.0 ml of water instead of root extract or m-tyrosine solution for controls. Each assay was performed in triplicate, and repeated at three different times. Root growth inhibition was visually observed and measured. Analysis of variance using the general linear model (GLM) procedure (SAS Inst., 1998) was carried out on the data (lettuce and crabgrass root and shoot length) and the means were separated by LSD at the P=0.05 level.

Dose-response curves were fitted to the following four-parameter logistic function:

$$f = \frac{b*(100-b)}{1 + e^{(ln(x)-ln(a))}}$$

where b is the smallest value of the dependent variable, i.e., root or shoot length, respectively, x is concentration of inhibitor, and $I_{50}$ is the concentration for 50% inhibition of the test species.

Example 31

Bioassays to Assess General Phytotoxicity of m-Tyrosine

Using the Petri dish bioassay described above, various weed and crop species were tested for their susceptibility to m-tyrosine. Concentrations evaluated were 10, 20, 40, 80, 160, and 320 µM m-tyrosine dissolved in water.

Example 32

Comparison of Phytotoxic Activity of Racemic m-Tyrosine and L-m-Tyrosine

The activities of L-m-tyrosine and racemic m-tyrosine were compared using the Petri-dish assays described above. The Petri dishes were treated with 1 ml of aqueous solutions of either racemic or L-m-tyrosine at concentration of 10, 20, 40, 80, 160, and 320 µM. Controls consisted of Petri dishes with filter paper to which 1.0 ml of pure water was added. Ten surface-sterilized lettuce seeds were placed on the moist paper filter in each Petri dish. After five days in a controlled environment (light regime of 45.33 µmol photons $m^{-2}$ $s^{-1}$ at temperature of 22° C.), radicle and shoot length were measured.

Example 33

Assessment of Potential Phytotoxicity of o- and p-Tyrosine

To determine if o- or p-tyrosine possess some of the phytotoxic properties of m-tyrosine, commercial o-tyrosine, p-tyrosine and m-tyrosine were subjected to the Petri dish bioassay described above, using concentrations of 10, 20, 40, 80, 160, and 320 µM of o-, p-, and m-tyrosine. Controls received only distilled water. The results showed that while m-tyrosine exposure results in radicle elongation inhibition, lettuce seedling growth is stimulated by o- or p-tyrosine at concentrations as low as 50 µM. All assays were conducted in triplicate.

Example 34

Assessment of Potential Autotoxicity of m-Tyrosine

To determine if m-tyrosine had an effect on root elongation of fine leaf fescue, commercial m-tyrosine was tested using our Petri dish bioassay, with fine leaf fescue seeds instead of lettuce seeds, and m-tyrosine concentrations of 10, 20, 40, 80, and 160 µM. Controls received only distilled water. The assays were conducted in triplicate.

Example 35

Soil Experiments

Twenty grams of sand were mixed with 20 g of soil (loam) using a mortar. The resulting 40 g of soil media was mixed in a plastic Petri-dish with 15 ml of an aqueous solution containing m-tyrosine. Four concentrations of m-tyrosine were tested: 0, 1.3, 2.7, 5.5, and 11 mM. Lettuce seeds (*Lactuca sativa* L.) were washed for 1 minute in 10% aqueous sodium hypochlorite, and then washed for 1 minute in a one-to-one mixture of ethanol and water. Subsequently, the seeds were rinsed three times with milliQ water. Fifteen seeds were planted in each Petri-dish. The Petri-dishes were kept under light (45 µmol photons $m^{-2}$ $s^{-1}$) at 50-70% relative humidity and 25° C. for seven days. After five days, 10 ml of water was added to each Petri-dish to maintain appropriate moisture for lettuce growth. In another series of experiments, a commercially available peat moss (MetroMix) was used in place of the sand-loam mixture. Root and shoot length of seven-days-old lettuce seedlings were recorded for both experiments. Analysis of variance using the general linear model (GLM) procedure (SAS Inst., 1998) was carried out on the data (lettuce root and shoot length) and the means were separated by LSD at the P=0.05 level. Each assay was conducted in triplicate.

Example 36

Bacterial and Fungal Assays m-Tyrosine was evaluated for its effect on several bacteria (*Bacillus cereus, Bacillus subtilis*, and *Escherichia coli*) grown on nutrient agar (Difco) plates (9 cm) and a fungal culture (*Metarhizium anisopliae* (Metsch.)) grown on potato dextrose agar (Difco) plates. These plates were spread with either 0.5 mL aliquots of a liquid bacterial culture grown for 18 h in nutrient broth or with 0.5 mL of a fungal spore suspension (1×106 spores/mL), and were allowed to dry for approximately 30 minutes. Subsequently, 10, 5, 2.5, or 1.25 µg of m-tyrosine (20, 10, 5, 2.5 µl of a stock solution of 5 mg/ml m-tyrosine) was loaded onto a 4 mm paper filter disc, which was air-dried prior to placement onto the agar surface. A disc moistened with 10 µl of water served as negative control, and positive controls consisted of discs spiked with ampicillin and tetracycline (5 µg). The plates were placed in an incubator at 25° C., and visually checked for zones of inhibition for up to four days. All experiments were performed in triplicate.

Example 37

Effect of m-Tyrosine on the Mitotic Index of Onion Cells

Onion seeds were grown on filter paper in Petri dishes as described above, using 10, 20, 40, 80, and 160 µM m-tyrosine concentrations. Root tips were stained for light microscopy examination using the Feulgen reaction. Root tips of three mm length were treated with a mixture of absolute ethanol: glacial acetic acid for two hours. The ethanol-glacial acetic acid mixture was removed and the tips were rinsed with distilled water. Subsequently, the root tips were hydrolyzed in 5 N HCl for one hour at room temperature, before being stained in Feulgen's reagent for 30 minutes. For each m-tyrosine concentration, five individual root tips were removed and macerated in a drop of 45% acetic acid on a slide, and the mitotic stages of the onion root tip cells were observed under a light microscope. Three replicates were observed for each treatment. One thousand cells were recorded per replication, resulting in observation of a total of 3000 cells per treatment. The experiment was repeated three times.

TABLE 7

Mitotic index of onion root tips exposed to synthetic m-tyrosine at different concentrations.

| m-Tyrosine | Total cells observed (%) | | | |
| --- | --- | --- | --- | --- |
| | Prophase | Metaphase | Anaphase | Telophase |
| Control | 3 | 1.8 | 1.2 | 2 |
| 10 | 2.2 | 1.4 | 1.6 | 2 |
| 20 | 2 | 1 | 1.1 | 1 |
| 40 | 1 | 0.4 | 0.6 | 0.2 |
| 80 | 0.5 | 0 | 0.5 | 0.2 |
| 160 | 0.2 | 0 | 0 | 0.3 |

Example 38

Selectivity and Distribution of m-Tyrosine, a Phytotoxin Identified in Root Exudates of Certain Fine Leaf Fescue Species Examples 38-42 are related to experiments involving selectivity and distribution of m-tyrosine (a phytotoxin identified in root exudates of certain fine leaf fescue species). A compound isolated and identified using activity-guided fractionation in fine fescue (*Festuca rubra rubra* L.) root exudates was tested for its biological activity. m-Tyrosine, a simple amino acid analogue, exhibited characteristic phytotoxic effects upon numerous plant species, i.e., inhibition of growth at high concentrations and little or no effect at very low concentrations. The relative phytotoxicity of m-tyrosine as measured by root growth inhibition of seedlings of selected crop and common turf weed species was investigated. Weeds commonly encountered in turf settings were tested for their sensitivity to m-tyrosine, as well as several crops including sudex (sorghum sudangrass hybrid), tobacco, lettuce, cress, and tomato. The concentration of m-tyrosine required to observe 50% inhibition of radicle elongation of plant species tested ($I_{50}$) was determined using a dose response-curve. Common chickweed was the most sensitive species to m-tyrosine ($I_{50}$=9 µM), and barnyardgrass was the least sensitive ($I_{50}$=257 µM). m-Tyrosine production was evaluated within a diverse collection of fine leaf fescue germplasm grown on a soil-free system. Fine leaf fescue genotypes varied considerably in the amount of m-tyrosine produced. Based on HPLC analysis, two-week-old Arizona fescues were the *Festuca* subspecies producing the largest amount of m-tyrosine, followed by chewing's and creeping fescues.

Example 39

Weed and Crop Bioassays m-Tyrosine activity was bioassayed using selected weed and crop species. Growth inhibition as measured by radicle elongation was evaluated in dandelion (*Taraxacum officinale* Weber in Weggers.), large crabgrass (*Digitaria sanguinalis* (L.) Scop.), velvetleaf (*Abutilon theophrasti* Medicus), black medic (*Medicago lupulina* L.), curly cress (*Lepidium sativum* L.), barnyardgrass (*Echinochloa crus-galli*.(L.) Beauv.), lettuce (*Lactuca sativa* L.), purslane (*Portulaca oleracea* L.), annual bluegrass (*Poa annua* L.), birdsfoot trefoil (*Lotus corniculatus* L.), broadleaf plantain (*Plantago major* L.), mouseear chickweed (*Cerastium vulgatum* L.), common chickweed (*Stellaria media* (L.) Vill.), white clover (*Trifolium repens* L.), wheat (*Triticum aestivum* L.), tomato (*Lycopersicon esculentum* var. *esculentum* P. Mill.), tobacco (*Nicotiana tobacum* L.), and sorghum sudangrass hybrid (*Sorghum bicolor* x *Sudanese*). Weeds were purchased from Herbi-Seeds, England, tomato seeds were purchased from Agway (Ithaca N.Y.), and wheat, sudex and tobacco where donated by Pioneer Seeds (Johnson, Iowa). Seeds were sterilized by a water: ethanol mixture (1:1) for one minute and rinsed three times thoroughly in distilled water. The simple phytotoxicity bioassay utilized consisted of the evaluation of radicle length of ten sterilized seeds of each weed/crop deposited on a filter paper containing the appropriate m-tyrosine test solution in 4.5 cm Petri dishes. The amino acid analog, m-tyrosine was purchased from Sigma and formulated at concentrations of 0, 20, 40, 80, 160 and 320 µM by initially dissolving in aqueous solutions. A 1000 µL aliquot of the appropriate test solution was added to individual Petri dishes lined with Whatman No. 1 filter paper. Control dishes received 1000 µL of water. After seeds were placed on moistened filter paper, Petri dishes were transferred to a controlled environment with a light regime of 45,33 photon $m^{-2}$ $s^{-1}$ and maintained at an average temperature of 25° C. for 7 days. At the end of the incubation period, radicle length was measured. Treatments were replicated three times, and the experiment for each plant species tested was repeated three times.

Example 40

Screening of Fine Fescue Germplasm for m-Tyrosine Content in Root Exudate

A diverse collection of fine fescue germplasm and several other less closely related grass species were screened for m-tyrosine production with 14-day-old seedling roots produced on a capillary mat system (Czarnota. M.A., "Sorghum (*Sorghum* spp.) Root Exudates, Production, Localization, Chemical Composition, and Mode of Action," in *Floriculture and Ornemantal Horticulture Ithaca, N.Y.: Cornell University, pp* 105 (2001), Czarnota et al., "Evaluation of Root Exudates of Seven *Sorghum* Accessions," *J. Chem. Ecol.* 29:2073-2083 (2001), which are hereby incorporated by reference in their entirety), using 50 g of 25 seed per screen. Root fresh weight was recorded for each accession screened, and total quantity of m-tyrosine was determined after aqueous extraction. m-Tyrosine was extracted from different fine leaf fescue cultivars and species as well as tall fescue (*Festuca arundinaceae* L.), Kentucky bluegrass (*Poa pratensis* L.), and perennial ryegrass (*Lolium perenne* L.) (Table 8).

TABLE 8

Various fine leaf fescue species, subspecies, and cultivars tested for m-tyrosine content as well as other grass species.

| Species | Scientific Name | Cultivars | m-Tyrosine Content (µg/g root fresh weight) |
| --- | --- | --- | --- |
| Strong Creeping and Creeping Red Fescue | *F. rubra* L. rubra | Salem | 59.5 |
| | | Jasper | 40 |
| Chewing's Fescue | *F. rubra* L. Subsp. *commutata* Gaud | Wilma | 11 |
| | | Columbra | 2.5 |
| | | Sandpiper | 8.6 |
| | | Intrigue | 72 |
| Arizona Fescue | *F. arizonica* L. | — | 83 |
| Hard Fescue | *F. longifolia*. L. Thuill | Rescue 911 | 0 |
| | | Oxford | 0 |
| | | Reliant | 0 |
| Sheep Fescue | *F. ovina* L. | — | 0 |
| Idaho Fescue | *F. idahoensis* L. | — | 0 |

TABLE 8-continued

Various fine leaf fescue species, subspecies, and cultivars tested for m-tyrosine content as well as other grass species.

| Species | Scientific Name | Cultivars | m-Tyrosine Content (µg/g root fresh weight) |
|---|---|---|---|
| Perennial Ryegrass | *Lolium perenne* L. | Palmer | 0 |
|  |  | Prelude 4 | 0 |
| Kentucky Bluegrass | *Poa pratensis* L. | — | 0 |

Grass seeds were sterilized in a water ethanol mixture (1:1) for one minute and rinsed three times in distilled water. Subsequently, seeds were allowed to germinate on a capillary mat system. After two weeks, seedling roots were weighed for fresh weight determination and were then excised and dipped (15 min) in water to extract m-tyrosine. The crude extract was filtered and then evaporated to dryness using a rotorary evaporator. The dried extract was dissolved in 6 ml water and analyzed for m-tyrosine content by high pressure liquid chromatography (HPLC) using a reversed phase Nova-Pak C18 column (3.9×150 mm, 4 um). The mobile phase was a gradient as described in Table 9.

TABLE 9

HPLC gradient for mobile phase used for evaluation of m-tyrosine content in fescue root exudate extracts.

|  | Methanol (%) | Water (%) | 0.05% TFA in Water (%) |
|---|---|---|---|
| 0-3 min | 3 | 67 | 30 |
| 3-30 min | 50 | 20 | 30 |
| 30-32 min | 100 | 0 | 0 |
| 32-42 min | 100 | 0 | 0 |
| 42-46 min | 3 | 67 | 30 | m-Tyrosine was detected at 280 nm using a photodiode array detector after 20 uL of the water solubilized crude extract sample was injected. The column flow rate was 3.4 mL/min with a 10 minute total run time.

Example 41

Effect of the Environment on m-Tyrosine Production

Four separate environmental regimes were evaluated for impact on m-tyrosine production in fescue root exudates. The normal growth condition (control) refers to the growth of 50 g of previously sterilized fine leaf fescue seeds (cultivar Intrigue) on a capillary mat system for two weeks. To allow proper germination and growth of the seedlings, water was supplied continuously for two weeks and the capillary mat system was maintained under a light regime of 45 µmol photons $m^{-2}$ $s^{-1}$ and a temperature of 25° C. The second growth regime consisted of producing fescue roots in the dark by covering the capillary mat system with black plastic during the experiment. All other growth parameters were similar to the control regime. In the third regime, a nutrient solution was added to the capillary mat system while light, and water supply remained as described for the control conditions. In the fourth regime, the growing conditions were modified by supplying water to the capillary mat system initially during day 1, and then limited water availability over time. Light regime and temperature remained identical to the control regime.

Each experiment consisted of roots generated on individual screens in the capillary mat production system, subjected to one of the growth regimes described above. Roots were collected and extracted individually from each screen as describe above, generating three replicates for HPLC analyses. The experiment was then repeated over time.

Example 42

Figure 18:
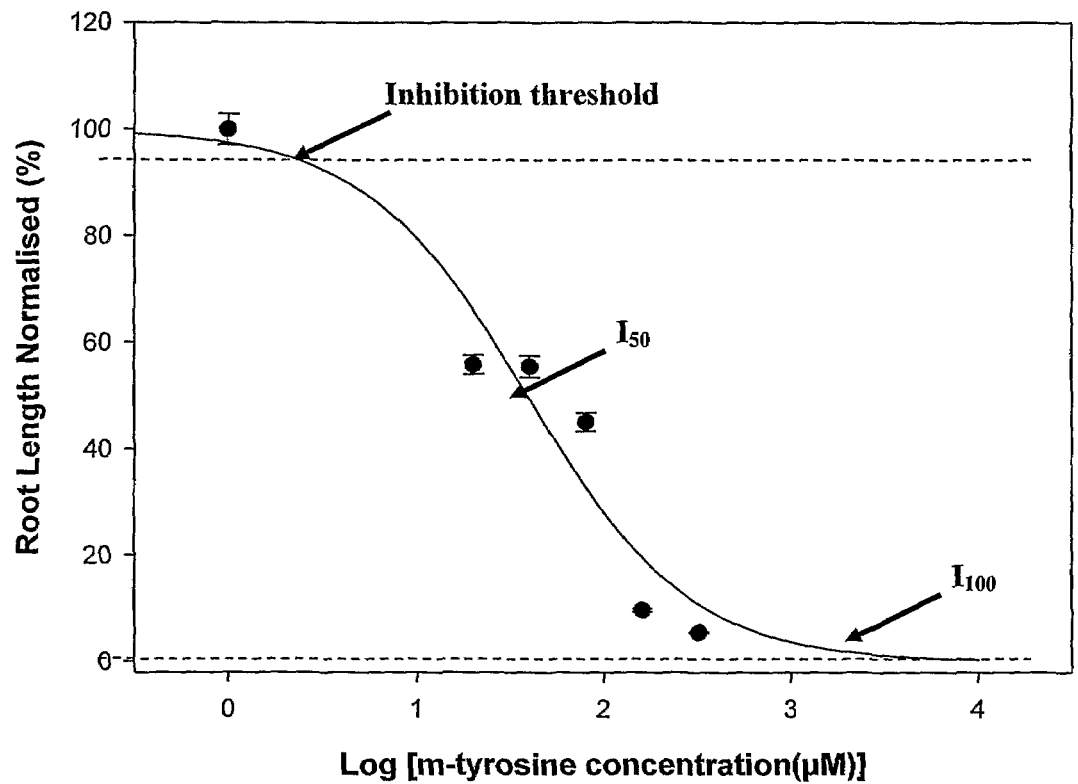
FIG. 18 shows a typical dose-response curve obtained for the weed and crop species tested. This dose response-curve represents the effect of m-tyrosine on root elongation of seven-day old large crabgrass seedlings. Error bar=1±SE. Inhibition threshold refers to the minimum concentration of m-tyrosine needed to observe some toxicity.

Results and Discussion: Selectivity and Distribution of m-Tyrosine, a Phytotoxin Identified in Root Exudates of Certain Fine Leaf Fescue Species All species evaluated were generally sensitive to the presence of m-tyrosine over a broad range of concentrations and generated similar dose-response curves (FIG. 18). However, specific individual responses of weed and crop species to inhibition by m-tyrosine varied and I50 values were species dependant (Table 10).

TABLE 10

Inhibition of plant growth as measured by radicle length of selected plant species in the presence of various concentrations of m-tyrosine.

|  | Species Evaluated | $I_{10}$ (µM) | $I_{50}$ (µM) | $I_{100}$ (µM) |
|---|---|---|---|---|
| Crop Species | Lettuce | 6 | 20 | —[1] |
|  | Cress | 15 | 23 | — |
|  | Tobacco | 30 | 40 | 160 |
|  | Tomato | 35 | 75 | 160 |
|  | Sudex | 50 | 151 | — |
|  | Wheat | 80 | 157 | — |
| Weed Species | Mouseear chickweed | 6 | 9 | 47 |
|  | *Arabidopsis* | 6 | 15 | 50 |
|  | Large Crabgrass | 20 | 38 | 320 |
|  | Dandelion | 10 | 39 | 160 |
|  | Birdsfoot trefoil | 20 | 42 | — |
|  | Annual bluegrass | 25 | 47 | 320 |
|  | Broadleaf Plantain | 30 | 72 | — |
|  | Black Medic | 40 | 84 | — |
|  | Velvetleaf | 40 | 168 | — |
|  | Common Chickweed | 80 | 174 | 320 |
|  | Barnyard grass | 80 | 257 | — |

Figure 19:
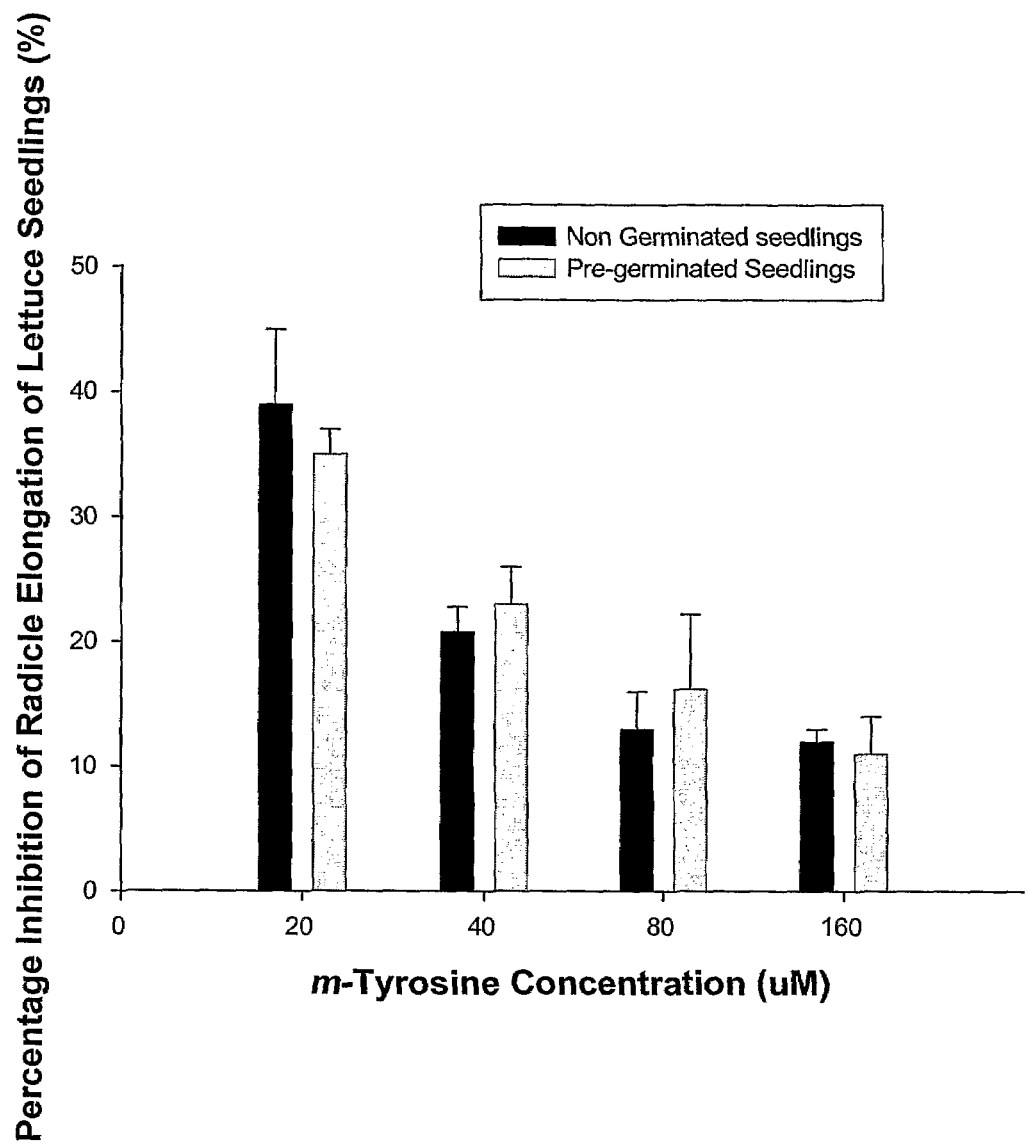
FIG. 19 shows a comparison of m-tyrosine activity on growth of pregerminated and non-germinated lettuce seedlings. Error bar=1±SE.

[1]Even at the highest concentration of m-tyrosine tested, complete inhibition of radicle elongation was not observed in certain species For instance, radicle length of mouseear chickweed was inhibited by increasing m-tyrosine concentration, with 50% inhibition at a concentration of 9 µM m-tyrosine, compared to the control. Mouseear chickweed was most sensitive to m-tyrosine; radicle elongation of other species evaluated showed 50% inhibition at concentrations ranging from 14 to 253 µM (Table 10). Barnyardgrass, velvetleaf, and common chickweed were the least sensitive weed species evaluated. When m-tyrosine solutions were added to pre-germinated lettuce seeds, root elongation of lettuce was strongly inhibited, similarly to previous assays without seed pregermination (FIG. 19). From these observations with numerous seedling indicators, it was concluded that m-tyrosine had an inhibitory effect only on radicle elongation, but did not affect seed germination per se. In comparison to sorgoleone, a bioactive hydroquinone produced by sorghum species and exuded by living sorghum roots, m-tyrosine appears to be toxic to a broader range of plant species. Sorgoleone activity was also species dependant, but small-seeded broadleaf species were more sensitive to the presence of sorgoleone. In general, concentrations of sorgoleone required for seedling growth inhibition using a similar Petri dish bioassay were 10-to-100 fold higher than those observed for m-tyrosine (Czarnota et al., "Evaluation of Root Exudates of Seven *Sorghum* Accessions," *J. Chem. Ecol.* 29:2073-2083 (2001); Czarnota. M.A., "Sorghum (*Sorghum* spp.) Root Exudates, Production, Localization, Chemical Composition, and Mode of Action," in *Floriculture and Ornemantal Horticulture*, Ithaca, N.Y.: Cornell University, pp 105 (2001); Nimbal et al., "Phytotoxicity and Distribution of Sorgoleone in Grain *Sorghum* Germplasm," *J. Agric. Food Chem.* 44:1343-1347 (1996), which are hereby incorporated by reference in their entirety).

m-Tyrosine was also inhibitory to shoot elongation. However, the level of toxicity observed was much lower in comparison to radicle elongation, a more sensitive indicator of growth inhibition. Supplemental experiments are needed to determine whether inhibition of shoot elongation is due to a direct or indirect effect of m-tyrosine.

Bioassays were conducted over the course of 5 to 10 days, depending on the species; greater potential effects on shoot development may have been observed if bioassays were conducted for a longer period of time. However, bleaching or discoloration of seedling leaves or hypocotyls was observed in some species. Variation in species sensitivity to m-tyrosine could be attributed to several factors. Uptake of m-tyrosine may be species dependent, as well as translocation within developing species. Both small and large seeded species were influenced by m-tyrosine; seed size does not appear to impact selectivity. Similarly, both monocots and dicots were sensitive to the presence of m-tyrosine, suggesting that m-tyrosine is not particularly selective, but a broad spectrum inhibitor. No inhibition was observed when fine leaf fescue species producing m-tyrosine were grown in presence of m-tyrosine. Chewing's fescue seedlings, cultivar Intrigue must have the ability to limit root uptake of m-tyrosine or to detoxify this amino acid analog.

Screening of fescue species for m-tyrosine production indicated that considerable variation exists among fescue genotypes with respect to the amount of m-tyrosine produced (Table 8). It appears that under controlled conditions, the production and secretion of m-tyrosine is dependent on inherent genetic differences among fine leaf fescues, apart from environmental factors. Cultivars representing four fine leaf fescue species consistently produced m-tyrosine in their root exudates; specifically Arizona fescue, strong, creeping red, and chewing's fescue. In comparison, other fine leaf fescue subspecies *and* species did not produce m-tyrosine (hard fescue, sheep fescue, and Idaho fescue). In addition, Kentucky bluegrass, perennial ryegrass, and tall fescue did not produce any detectable levels of m-tyrosine. Arizona fescue produced the highest level of m-tyrosine per gram of fresh root (83 µg/g fresh root) under the capillary mat growth system. Within fescue subspecies, m-tyrosine production also varied; Wilma, a chewing's fescue produced five times more m-tyrosine than Columbra, another chewing's fescue (2.5 vs 11 µg/g fresh root). Furthermore, Intrigue, another chewing's fescue produced seven times more m-tyrosine that Wilma (72 vs 11 µg/g fresh root).

Allelochemical production is often influenced by environmental factors such as temperature, light quality and quantity, soil moisture, nutrients, and presence of soil microorganisms, among other factors. The quantity of allelopathic compounds produced by higher plants has often been shown to be significantly higher under stressful growth environments (Chou, C., "Roles of Allelopathy in Plant Diversity and Sustainable Agriculture," *Critic. Rev Plant Sci* 18:609-636 (1999), which is hereby incorporated by reference in its entirety). For example, *Salvia leucophylla* L. and *Artemisia* species, growing in a semiarid area of Southern California, produced significantly greater amounts of allelopathic monoterpenes by volatilization in comparison to production under moist growth conditions (Chou, C., "Roles of Allelopathy in Plant Diversity and Sustainable Agriculture," *Critic. Rev Plant Sci* 18:609-636 (1999), which is hereby incorporated by reference in its entirety). In a series of experiments, the effect of three different stress regimes upon root exudation and m-tyrosine production was evaluated. Addition of a nutrient solution in irrigation water in the capillary mat system did not have a significant effect on m-tyrosine production by Intrigue, a chewing's fescue. In the absence of light, living roots of fine leaf fescue, cv "Intrigue" did not contain different levels of m-tyrosine in comparison to the standard regime.

Figure 20:
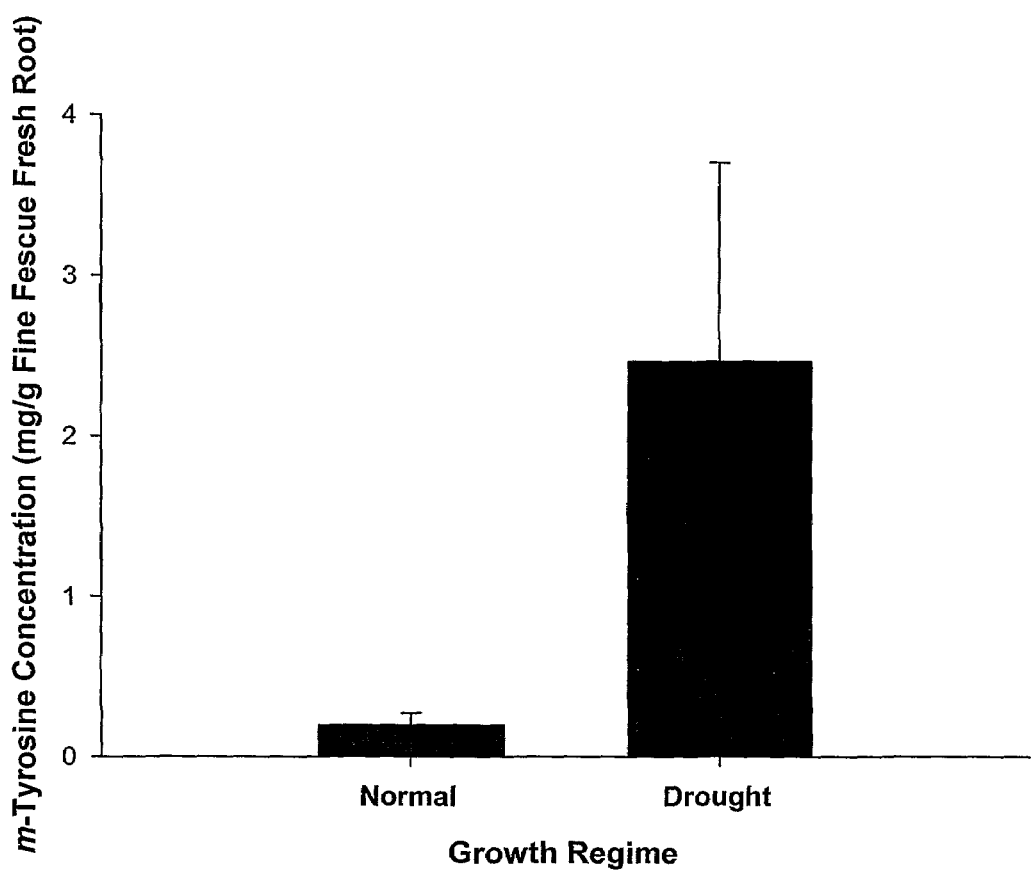
FIG. 20 shows an evaluation of m-tyrosine content in fine leaf fescue root exudates (cultivar Intrigue) under normal or limited moisture availability conditions.

In conclusion, m-tyrosine appears to be a broad spectrum inhibitor of seedling plant growth, effectively inhibiting radicle elongation rather than impacting seed contained in root exudates was ten-fold greater than chewing's fescue grown on a capillary mat system with greater moisture availability (0.2 mg/g versus 10 mg/g of fresh root) (FIG. 20) indicating drought or lack of moisture availability clearly impacted the production of root exudates and subsequent m-tyrosine content. Certain fescue species and cultivars produce greater levels of m-tyrosine within their respective root exudates; specifically chewing's fescue, strong creeping and red creeping fescue, and Arizona fescues. Certain stressful conditions have strong impacts on production and release of root exudates, and subsequently m-tyrosine levels within root exudates. Specifically, limited moisture or drought condition resulted in ten-fold increases of m-tyrosine in experiments under controlled laboratory conditions. m-Tyrosine may potentially play an important role as an allelochemical inhibitor, suppressing growth of common turf weed in landscape settings by certain species and cultivars of fine leaf fescues.

Example 43

Assessment of the Phytotoxic Potential of m-Tyrosine in Laboratory Soil Bioassays Examples 43-51 relate to the assessment of the phytotoxic potential of m-tyrosine in laboratory soil bioassays. Allelopathy involves complex plant-plant interactions mediated by the production of bioactive secondary plant products. Laboratory bioassays assessing allelopathy sometimes have little relevance to plant-plant interactions in field settings. Examples 43-51 describes the significance of soil-allelochemical interactions, and the role of N fertilizer as well as activated carbon in overcoming plant growth inhibition observed in a simulated field setting using a series of laboratory soil bioassays. The phytotoxicity of m-tyrosine was not strongly influenced by soil N application; however, when significant amounts of activated charcoal were added to the soil medium, growth inhibition observed in treated lettuce seedlings was strongly reduced. Soil texture did not strongly influence the bioavailability or activity of m-tyrosine. Even though laboratory studies cannot often demonstrate allelopathy as the sole factor responsible for the observed growth inhibition in the field, laboratory findings correlate well with previous findings in field settings, which suggested strong weed suppressive ability of several fine leaf fescue species and cultivars that release m-tyrosine over time in root exudates. With observed activity in both soil and soil-less growth assays, m-tyrosine has potential to act as an allelochemical in field settings.

Example 44

General Procedures

Soil (Arkport fine sandy loam: psamentic Hapludlafs, coarse loamy mixed mesic) was collected from a field situated at the Bluegrass Lane Research Farm at Cornell University in Ithaca, N.Y. Soil was allowed to dry at room temperature and was sieved (1.8 mm sieve) and mixed with autoclaved sand at a ratio of 1:1. In addition, a peat-based growth media, Metro-Mix, (Scotts Company, Maryville, Ohio) was utilized for experimentation. DL m-Tyrosine was purchased from Sigma-Aldrich and a stock solution was prepared to obtain a concentration of 0.6 mg m-tyrosine/ml of water.

Example 45

Soil Amendments

Soil sand media (40 g) was amended with 25 ml of 0.6 mg/ml m-tyrosine to provide a final concentration in each Petri dish of 20, 40, 80, and 160 µM m-tyrosine per dish. Soil that was amended with 25 ml water served as a control. A similar experiment was performed with MetroMix growth media utilizing an identical protocol. In addition, another experiment was run with MetroMix (15 g) amended with 0.25, 0.5, and 1 g of activated charcoal (Sigma, St. Louis, Mo., USA) and with m-tyrosine solution at concentration of 160 µM. Fifteen sterilized lettuce seeds were seeded and root and shoot lengths were recorded after 8 days. The experiment consisted of three Petri dishes for each charcoal concentration and was repeated over time.

An additional experiment was designed where Metromix (15 g) was amended with ni-tyrosine to formulate concentrations of 20, 40, 80, 160 µM m-tyrosine. For each m-tyrosine concentration, 0.25, 0.5, and 1 g of activated charcoal was added. Soil that was only amended with distilled water served as a control. For this experiment, each concentration of activated charcoal and m-tyrosine was replicated three times and was repeated over time.

Appropriate amounts of ammonium nitrate ($NH_4NO_3$) were dissolved in water to obtain final concentrations of 0.25, 0.5, 0.75, and 1.0 mM of N fertilizer. MetroMix (15 g) was amended with aqueous solutions of 0.125, 0.5, 0.75, and 1.0 mM of N fertilizer and of m-tyrosine at a concentration of 160 µM. The experiment was designed with three replications in a complete randomized design and was repeated over time.

Example 46 m-Tyrosine Persistence Experiment

MetroMix media (15 g) was amended with 25 ml of 0.6 mg/ml m-tyrosine to provide a final concentration in each Petri dish of 160 µM m-tyrosine per dish. Lettuce seeds were sown at day 0, 2, 5, 7 and 15 days after the aqueous solution of m-tyrosine was mixed with the soil media. Lettuce radicles were measured seven days after seeding and percent inhibition of radicle growth was recorded. The experiment was designed with three replications in a complete randomized design and was repeated over time.

Example 47

Growth Experiment

Lettuce was selected as the assay species of choice because it exhibits rapid and uniform germination. Large crabgrass was also included in the first two experiments because it is a common weed in turf settings. Prior experiments have shown that m-tyrosine is a potent inhibitor of root growth of large crabgrass and lettuce (Bertin et al., "Laboratory Assessment of the Allelopathic Effects of Fine Leaf Fescues," *J. Chem. Ecol.* 29:1919-1937 (2003), which is hereby incorporated by reference in its entirety). Soil and MetroMix, as described as previously, were placed in 9-cm petri dishes, and 15 lettuce or crabgrass seeds were sown on the soil surface. Each experiment was replicated three times and was repeated over time. Root and shoot length of lettuce and large crabgrass were recorded after seven days of growth at a temperature of 25° C. and lighting of 45.85 µmol photon $m^{-2}s^{-1}$.

Example 48

Statistical Analysis

Each data set was statistically analyzed using the general linear model (GLM) procedure (SAS Inst., 1998, which is hereby incorporated by reference in its entirety). Means were separated by LSD at the p=0.05 level.

Example 49

Soils Amended with m-Tyrosine Studies

Soil that was amended with m-tyrosine suppressed both the root and the shoot growth of lettuce and increasing concentrations provided greater inhibition of growth, especially impacting radicle elongation (FIG. 21). m-Tyrosine was easily dissolved in an aqueous solution, similar to commercial herbicide formulations which are used in turf and landscape settings. Lettuce was initially able to germinate under the conditions provided, but further growth was generally limited due to the phytotoxicity of the m-tyrosine treatments, indicating that m-tyrosine was taken up or imbibed from the soil solution by developing seedlings over a five day period.

Figure 21:
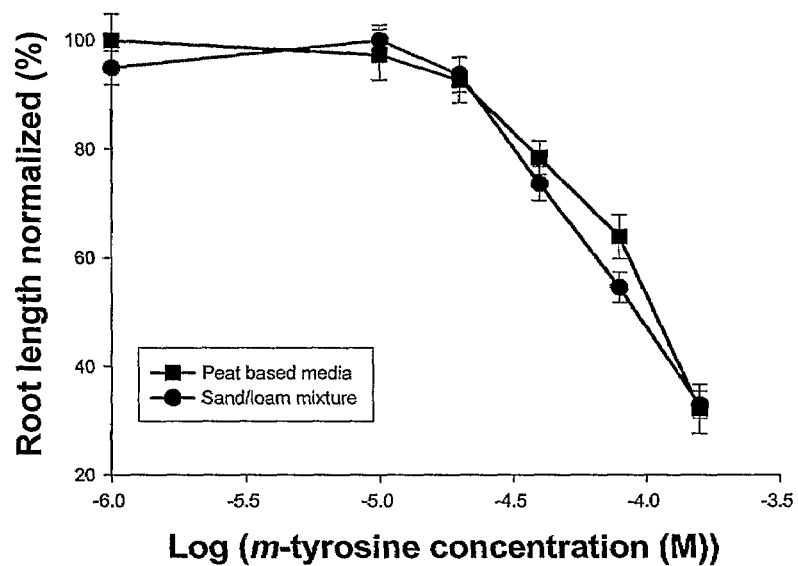
FIG. 21 shows the effect of a sand and loam mixture and MetroMix amended with four concentrations (0.1, 0.3, 0.5, and 1 mM) of m-tyrosine on root length of lettuce seedlings.

Compared with previous Petri-dish bioassays performed on paper filter, the concentration of m-tyrosine required in soil media for growth inhibition was higher. In comparison, the concentration of m-tyrosine required for 50% inhibition of root growth of lettuce ($I_{50}$) in soil is approximately 30 µM, whereas in a soil-less assay, the $I_{50}$ is approximately 8 µM. It is likely that in soil experiments, m-tyrosine interacts with soil particles due to binding to soil particles or organic matter, resulting in reduced specific activity in soil or organic-based media. Soil composition and texture could impact the activity of m-tyrosine in a field environment. However, in comparison with the sand/loam mixture, it was noted that in the peat-based MetroMix media with greater organic matter content, root growth inhibition was similar (FIG. 21). Soil particle or chemical interactions are likely responsible for any decrease in observed activity at of m-tyrosine in soil experiments versus soil-less conditions higher m-tyrosine concentrations.

The studies described herein clearly show the relatively potent activity of m-tyrosine even in soils with high organic matter. Al Hamdi et al. "Laboratory Bioassay for Phytotoxicity: An Example From Wheat Straw," *Agron. J:* 93:43-48 (2001), which is hereby incorporated by reference in its entirety, argued that allelopathy cannot be used to explain growth inhibition due to allelochemicals until data are available on the following: (1) the natural release of compounds from the plants releasing the chemical; (2) the concentration and persistence of the compound in the environment; and (3) the direct inhibition of plant growth by uptake of the target plant. In the studies described herein, field studies over three or four years in different locations showed the ability of certain fine leaf fescue cultivars to consistently displace weed populations (Bertin et al., "Further Evaluation of the Allelopathic Potential of Fine Leaf Fescue," *Proc WSSA* 56:116 (2002), which is hereby incorporated by reference in its entirety). After having isolated and identified a phytotoxin, m-tyrosine, released by several suppressive fine leaf fescue cultivars, laboratory bioassays have shown strong phytotoxicity towards selected turf weeds and crops.

These findings suggest that m-tyrosine is likely involved in the allelopathic interactions of fine leaf fescue species. Further experimentation under field conditions to quantify the rate of release of m-tyrosine in fescue root exudates can be performed to confirm the presence of allelopathic interactions in field settings. The potential use of synthetic particles to trap allelochemicals for later quantification in soil conditions could potentially simplify this work in field settings (Weidenhamer, J. D., "Biomimetic Measurement of Allelochemical Dynamics in the Rhizosphere," J. Chem. Ecol. 31:221-236 (2004), which is hereby incorporated by reference in its entirety).

Example 50

Nitrogen Fertility Study

In another study, different levels of N fertilizer were added to soil amended with and without m-tyrosine. In the absence of m-tyrosine, nitrogen application did not significantly affect the growth of lettuce seedlings, even at high concentrations of fertilizer N (1 mM). In the presence of m-tyrosine, it appeared that the addition of fertilizer N impacted root growth by slightly reducing toxicity; however, toxicity was never overcome even at high N concentrations (Table 11).

TABLE 11

Effect of soil amended with four concentrations (0.125, 0.25, 0.5, 1.0 mM) of ammonium nitrate on root growth of lettuce seedlings

| Ammonium Nitrate Concentration (mM) | Root Length of Lettuce Seedlings (cm) with m-tyrosine at 160 µM | Root Length of Lettuce Seedlings (cm) with no m-tyrosine (SE = ±1) |
|---|---|---|
| 0 | 2.07 (0.02) | 6.48 (0.37) |
| 0.125 | 3.56 (0.07) | 6.79 (0.32) |
| 0.25 | 4.82 (0.1) | 7.00 (0.29) |
| 0.5 | 4.8 (0.09) | 7.13 (0.35) |
| 1.0 | 4.8 (0.12) | 6.88 (0.47) |

Inhibition of radicle elongation was reduced by approximately 25% in the presence of n-tyrosine and 1 mM $NH_4NO_3$ in comparison to m-tyrosine applied without soil $NH_4NO_3$ (Table 11). Soil microbial activity was not measured in these assays, but higher microbial activity due to additional nitrogen fertilization is possible (Novak et al., "Sorption and Binding of Organic Compounds in Soil and Their Relation to Bioavailability," in Skipper et al., Eds., Bioremediation: Science and Applications, SSSA, Madison, Wis.: SSSA Spec. Publ. 43, p. 13-31 (1995), which is hereby incorporated by reference in its entirety). Therefore, additional nitrogen likely results in a reduction of m-tyrosine availability due to enhanced microbial degradation. The presence or bioavailability of organic compounds as substrates for microbial growth generally influences microbial activity. However, a supplemental experiment in sterilized soil could be helpful to better understand the role of soil microfauna on m-tyrosine toxicity.

Example 51

Soil Amended with Activated Charcoal Studies

Figure 22:
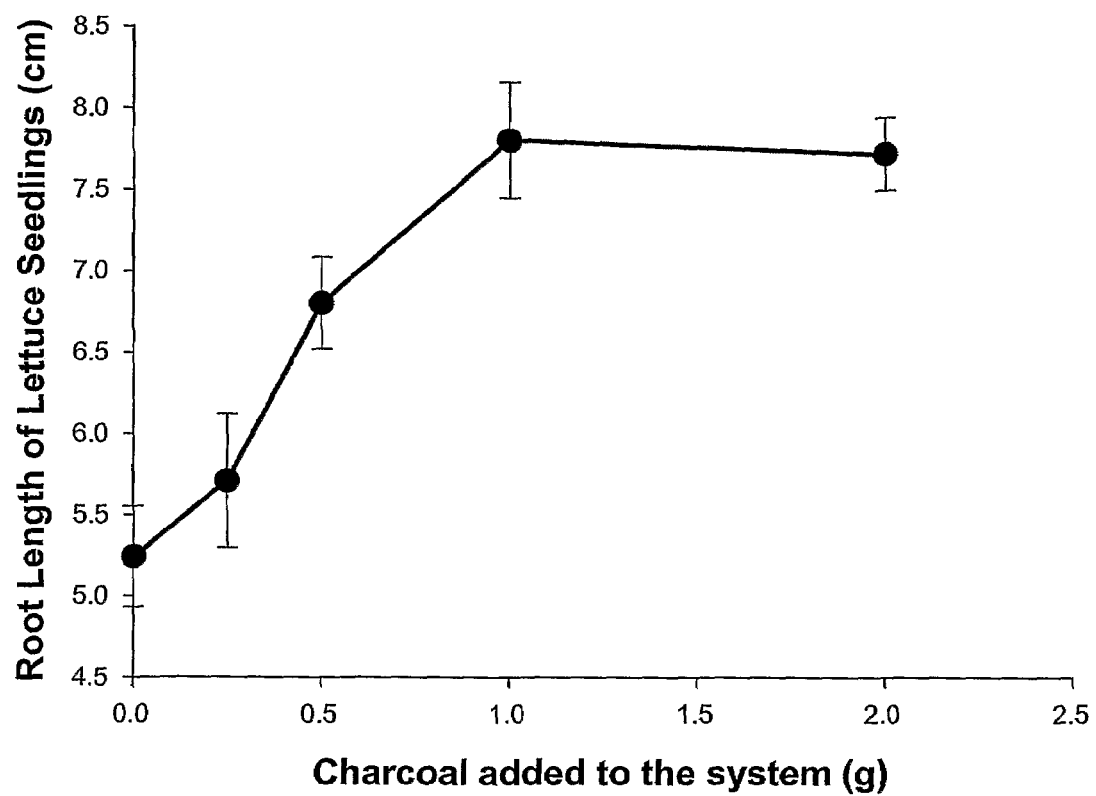
FIG. 22 shows the effect of soil amended with four concentrations (0.25, 0.5, 1.0, and 2.0 g) of activated charcoal on root growth of lettuce seedlings.
Figure 23:
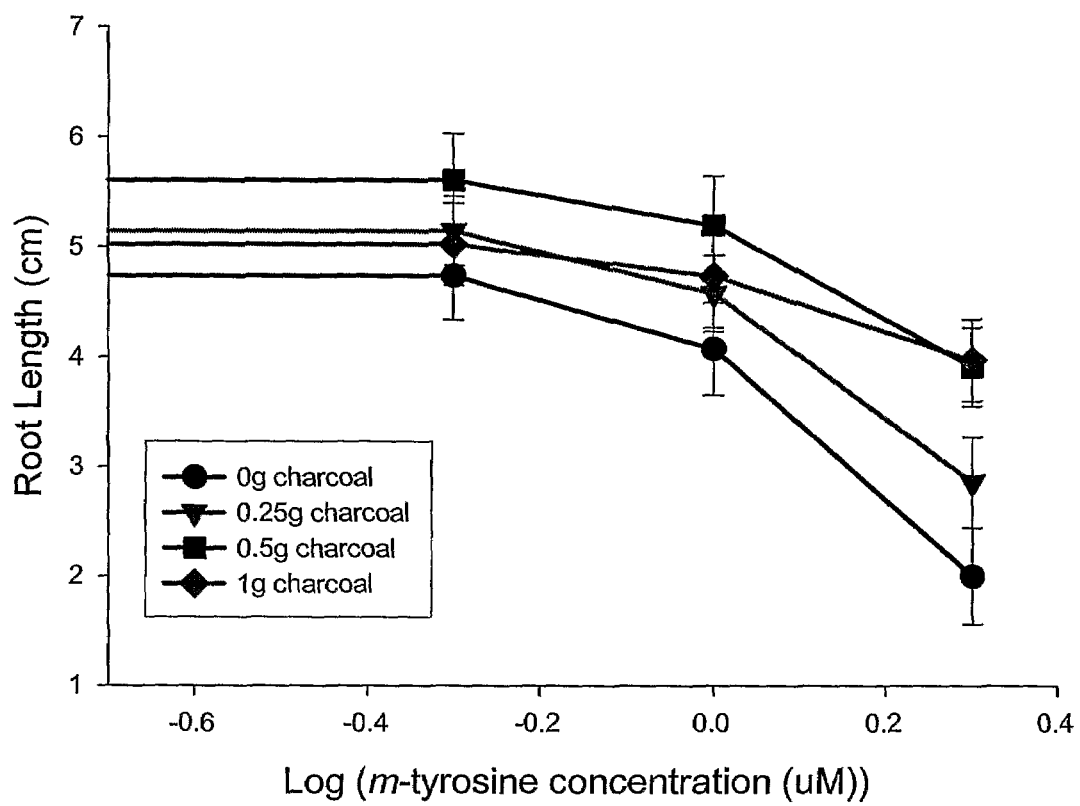
FIG. 23 shows the effect of soil amended with different concentrations of m-tyrosine and three concentrations (0.25, 0.5, and 1.0 g) of activated charcoal on root growth of lettuce seedlings.

Activated charcoal is often used to eliminate the interference or inhibition caused by organic molecules in soil-based systems (Inderjit et al., "Nature of the Interference Potential of Mugwort (Artemisia Vulgaris)," Weed Tech. 13:176-182 (1999); Mahall et al., "Root Communication Mechanisms and Intracommunity Distributions of Two Mojave Desert Schrubs," Ecology 73:1027-1043 (1992), which are hereby incorporated by reference in their entirety). By sequestering water-soluble organic constituents, the presence of activated carbon can remove allelochemicals from the soil in situ (Inderjit et al., "Bioassays and Field Studies for Allelopathy in Terrestrial Plants: Progress and Problems," Crit. Rev. Plant Sci. 22:221-238 (2003), which is hereby incorporated by reference in its entirety). Activated charcoal is usually used in field settings to remove residual herbicidal activity. Therefore, in the study described herein, the involvement of organic molecules in plant inhibition, in the presence of m-tyrosine, was addressed. The effect of m-tyrosine on lettuce seedlings root elongation grown in soil bioassays supplemented or not with activated charcoal was compared. Compared to the control, soil amended with different amounts of charcoal clearly impacted the toxicity of m-tyrosine on root growth of lettuce (FIGS. 22 and 23). Inhibition of root growth was still observed at low concentrations of activated charcoal; however, at higher concentrations, inhibition of root growth was much reduced in comparison to the control, suggesting that m-tyrosine was bound or inactivated by high soil concentrations of activated carbon. This experiment suggests that m-tyrosine can bind to organic soil constituents, resulting in reduced bioavailability and phytotoxicity. However, it is likely that some m-tyrosine remained available in the soil solution and was not completely absorbed, even at high carbon concentrations (FIG. 23).

Figure 24:
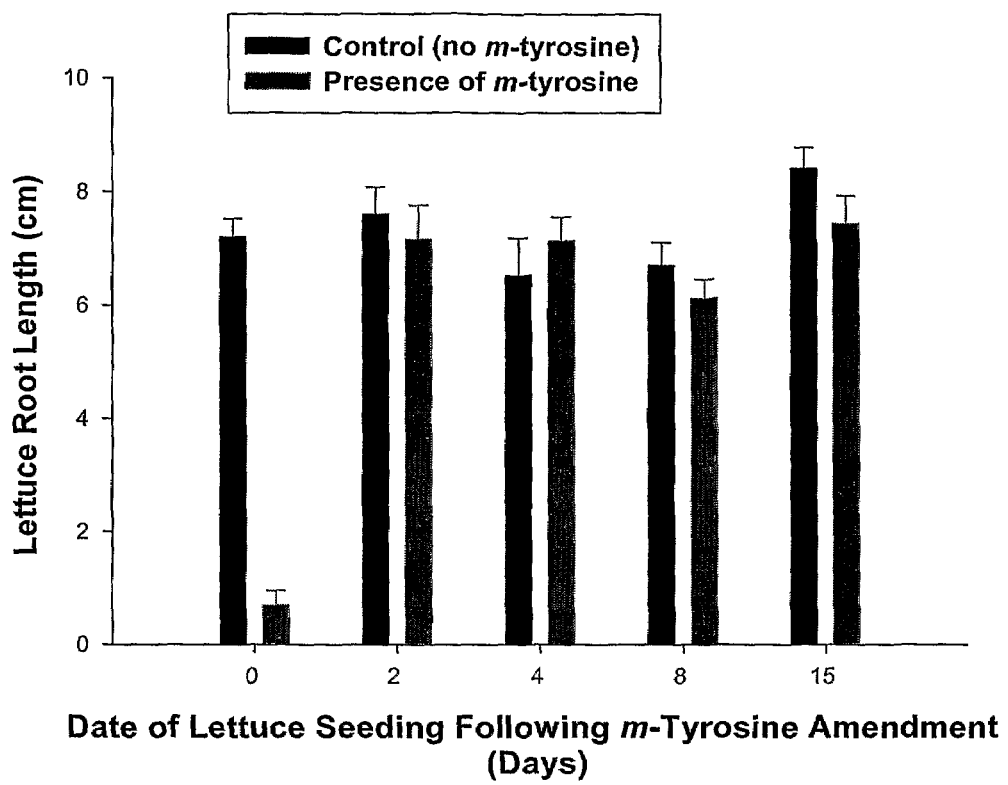
FIG. 24 shows the persistence of m-tyrosine in soil media as measured by lettuce seedling growth over time. m-Tyrosine was added to the soil media at date 0 and lettuce seeds were seeded after 0, 2, 4, 8, and 15 days.

Once allelochemicals are released into the environment, they are susceptible to decomposition or inactivation by microorganisms and also to chemical interactions which do not involve microorganisms (Rice, E. L., "Allelopathy," Orlando, Fla.: Academic Press (1984), which is hereby incorporated by reference in its entirety). Many environmental factors influence the persistence of allelochemicals in the soil (Burgos-Leon, W., "Phytotoxicité Induite Par les Résidus de Récolte de Sorghum Vulgare Dans les Sols Sableux de l'Ouest Africain," These de Doctorat, Université de Nancy, France, Nancy (1979), which is hereby incorporated by reference in its entirety). An additional study was performed to evaluate the persistence of m-tyrosine in soil-based growth media over time (FIG. 24). When lettuce seeds were seeded in MetroMix amended with m-tyrosine after two days prior to seeding, root and shoot growth inhibition was not significantly decreased compared to treatment at the time of seeding. These results indicate potential degradation of m-tyrosine between zero and two days after soil incorporation. In case of perennial species such as Festuca spp., consistent production and release of allelochemicals at phytotoxic levels is possible, even if degradation occurs over time, which may limit phytotoxicity. Continuous release of root exudates over time by the extensive living root system of fine fescues may result in replenishment of allelochemicals over time, given the apparently temporal persistence of m-tyrosine in soil settings. In comparison to other phenolics which are degraded within hours after application to soil settings, m-tyrosine exhibits comparable or greater levels of phytotoxicity (Blum et al., "Phenolic-Acid Content of Soils From Wheat-No Till, Wheat-Conventional Till, and Fallow-Conventional Till Soybean Cropping Systems," Journal of Chemical Ecology 17:1045-1068 (1991), which is hereby incorporated by reference in its entirety).

In conclusion, it has been demonstrated that m-tyrosine is active in a number of soil settings when present in significant concentrations for uptake by seedlings from the soil solution. It causes significant growth inhibition, particularly stunting of radicle elongation of both monocots and dicots. Phytotoxicity was not strongly affected by the addition of fertilizer nitrogen to soil media, nor by soil organic matter or textural alteration. In soil, the persistence and availability of ni-tyrosine impacted the presence of activated carbon which resulted in apparently decreased bioavailability of m-tyrosine and resulting phytotoxicity. In sand/loam soils, the persistence of m-tyrosine was limited, with an estimated half life of less than several hours. It is not surprising that persistence might be impacted by addition of organic carbon or by soil organic matter content, as many herbicides are similarly affected by soil type or addition of organic matter to soils (Cobb et al., "Herbicides and Their Mechanisms of Action Sheffield," Sheffield England: Academic Press (2000), which is hereby incorporated by reference in its entirety).

It is likely that m-tyrosine plays an important role in allelopathic interactions observed in fine fescue species; however, further experimentation under field settings to characterize the rate of release and relative persistence of m-tyrosine will be useful. m-Tyrosine has potential to be utilized as a natural or organic herbicide if bioavailability in soil settings can be somewhat enhanced by reformulation to allow for greater soil persistence, thereby enhancing inhibition of weed seedling growth over time.

Example 52

A Bioherbicide from *Festuca rubra*

Figure 25:
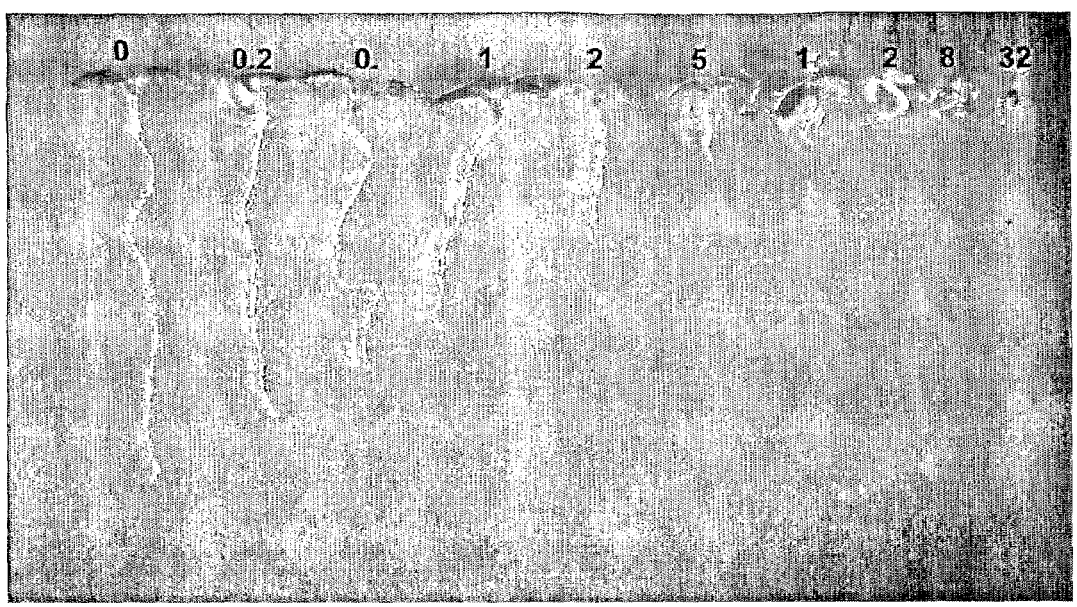
FIG. 25 shows a dose response curve for m-tyrosine, showing root growth inhibition after 7 days of growth, number represent concentrations in micromolar.

As part of an effort to investigate the mode of action of m-tyrosine, a series of additional experiments have been conducted using *Arabidopsis*, the results of which are described below:

Effect of m-tyrosine on *Arabidopsis thaliana*: Using *Arabidopsis thaliana*, an excellent plant model because of it well characterized genetics and the availability of mutants, the toxicity of m-tyrosine was determined and a dose response curve was elaborated. Root length of *Arabidopsis* is reduced by 50% when m-tyrosine is applied to the growth media at a concentration of 2 μM. This dose response curve was obtained with a mixture of D and L m-tyrosine. See FIG. 25.

Figure 26:
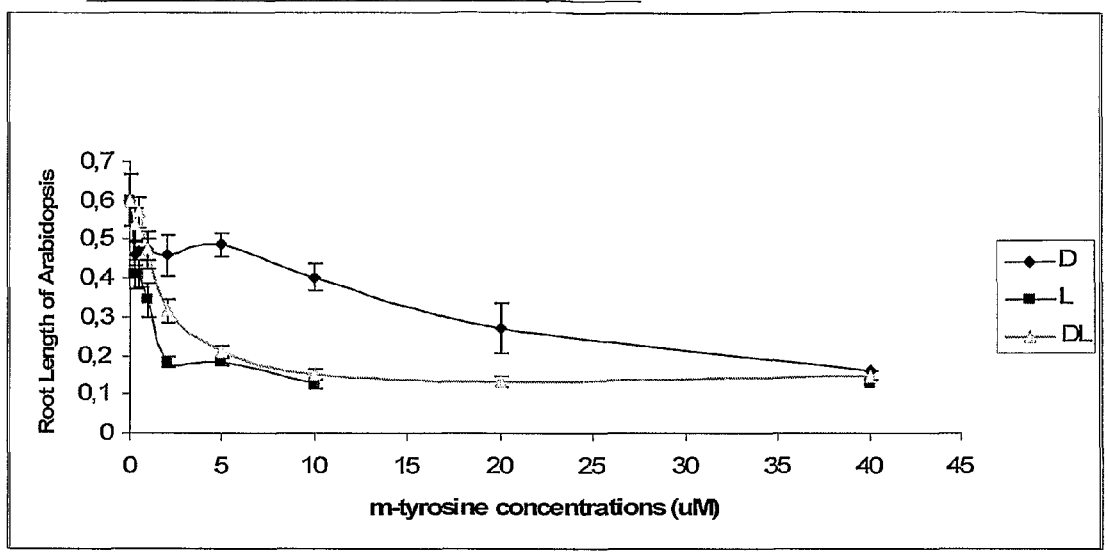
FIG. 26 shows a comparison of the toxicity of three forms of m-tyrosine (D, L, and DL) on *Arabidopsis thaliana* seedlings.

Effect of D versus L enantiomers of m-tyrosine: The L and DL forms are of roughly equal toxicity, while D-m-tyrosine is less toxic at low concentrations; however, at 40 μM, the same level of toxicity is observed for the three forms. See FIG. 26.

Figure 27:
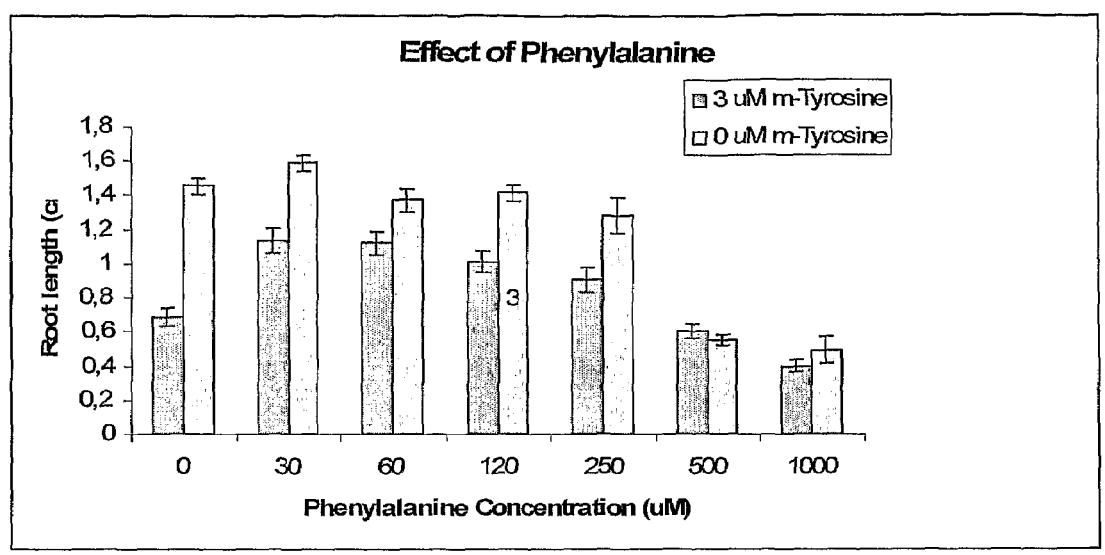
FIG. 27 shows the effect of the addition of phenylalanine on root growth inhibition initiated by m-tyrosine.

Effect of phenylalanine and p-tyrosine on the toxicity of m-tyrosine: A likely cause of m-tyrosine toxicity is that it interferes with tyrosine or phenylalanine metabolism. Addition of phenylalanine restored root growth to 80% of the control levels (FIG. 27). However, p-tyrosine, even at concentrations up to 1 mM, did not rescue root growth inhibition initiated by 3 μM of m-tyrosine.

The deaminated form of m-tyrosine, m-hydroxyphenylpyruvic acid, is as toxic as m-tyrosine; however, the root growth of *Arabidopsis* is not rescued when phenylalanine is added to the media.

The toxicity of m-hydroxyphenylpyruvic acid indicates that a larger variety of structural derivatives of m-tyrosine are of interest.

The structure space to be included should be based on the m-hydroxyphenyl motive, with variation of the side chain, including: (i) longer side chains; (ii) variation of the amino group substitution site (including hydroxyl, oxo, halogens, sulfides, as well as acyaled and alkylated amino and hydroxyl groups); (iii) variation of the functional group at the terminal carbon atom, consider hydroxy, amide, ester, imide, hydroxylamide, etc.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of inhibiting weed growth, said method comprising:

providing an m-tyrosine compound, wherein said m-tyrosine compound has a formula of Formula I:

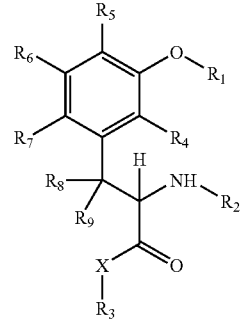

Formula I wherein
  $R_1$ and $R_2$ are independently selected from the group consisting of H, alkyl, alkenyl, alkynyl, and cycloalkyl;
  $R_3$ is selected from the group consisting of H, alkyl, alkenyl, alkynyl, and cycloalkyl;
  X is O;
  $R_4$, $R_6$, and $R_7$ are independently selected from the group consisting of H, hydroxyl, halogen, amino, and nitro;
  $R_5$ is selected from the group consisting of H, halogen, amino, and nitro; and
  $R_8$ and $R_9$ are independently selected from the group consisting of H, hydroxyl, halogen, amino, methyl, and halogenated methyl,
  or providing a salt of said m-tyrosine compound and
  treating a weed or weed seed with the m-tyrosine compound or the salt of said m-tyrosine compound under conditions effective to inhibit growth of said weed or weed seed in a growth medium.

2. The method according to claim 1, wherein the m-tyrosine compound has a formula of Formula I, wherein:
  $R_4$, $R_5$, $R_6$, $R_7$, $R_8$, and $R_9$ comprise H;
  $R_1$ and $R_2$ are independently selected from the group consisting of H, alkyl, alkenyl, alkynyl, and cycloalkyl;
  $R_3$ is selected from the group consisting of H, alkyl, alkenyl, alkynyl, and cycloalkyl; and
  X is O.

3. The method according to claim 1, wherein the m-tyrosine compound is in isolated form.

4. The method according to claim 1, wherein said providing comprises isolating the m-tyrosine compound from a source plant that produces the m-tyrosine compound.

5. The method according to claim 4, wherein the m-tyrosine compound is isolated from tissue of the source plant, said tissue being selected from the group consisting of root tissue, leaf tissue, shoot tissue, and foliage tissue.

6. The method according to claim 5, wherein said tissue is living tissue or dead tissue.

7. The method according to claim 4, wherein said source plant comprises a *Festuca* species.

8. The method according to claim 7, wherein said *Festuca* species is *Festuca rubra*.

9. The method according to claim 1, wherein said treating comprises applying the compound or the salt of said compound to the surface of the growth medium, prior to emergence of the weed from the growth medium, in an amount sufficient to inhibit growth of the weed or weed seed.

10. The method according to claim 9, wherein the compound or the salt of said compound is applied in granular form or liquid form.

11. The method according to claim 9, wherein said compound or the salt of said compound is applied at a level of about 0.5 to about 12.0 pounds per acre.

12. The method according to claim 1, wherein said treating comprises applying the compound or the salt of said compound to foliage of the weed in an amount sufficient to inhibit growth of the weed.

13. The method according to claim 12, wherein said applying is carried out by spraying the foliage with the compound or the salt of said compound.

14. The method according to claim 12, wherein the compound or the salt of said compound is applied at a level of about 0.5 to about 12.0 pounds per acre.

15. The method according to claim 1, wherein said treating comprises simultaneously applying the compound or the salt of said compound to the growth medium surface and to foliage of the weed in an amount sufficient to inhibit growth of the weed and/or weed seed.

16. The method according to claim 1, wherein said weed or weed seed is selected from the group consisting of a grass weed (monocot weed) and a broadleaf weed (dicot weed).

17. The method according to claim 16, wherein the weed is a grass weed and is selected from the group consisting of crabgrass, barnyardgrass, and annual bluegrass.

18. The method according to claim 16, wherein the weed is a broadleaf weed and is selected from the group consisting of dandelion, white clover, black medic, lettuce, birdsfoot trefoil, common chickweed, common purslane, and curly cress.

19. The method according to claim 1, wherein said growth medium is soil.

20. The method according to claim 1 further comprising admixing the compound or the salt of said compound with water, soil, fertilizers, and/or carriers.

21. A method of enhancing growth of a non-weed plant by inhibiting growth of weeds that are located proximate to said non-weed plant, said method comprising:

providing an m-tyrosine compound, wherein said m-tyrosine compound has a formula of Formula I:

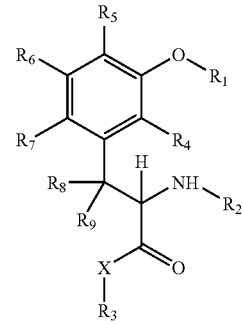

Formula I wherein
$R_1$ and $R_2$ are independently selected from the group consisting of H, alkyl, alkenyl, alkynyl, and cycloalkyl;
$R_3$ is selected from the group consisting of H, alkyl, alkenyl, alkynyl, and cycloalkyl;
X is O;
$R_4$, $R_6$, and $R_7$ are independently selected from the group consisting of H, hydroxyl, halogen, amino, and nitro;
$R_5$ is selected from the group consisting of H, halogen, amino, and nitro; and
$R_8$ and $R_9$ are independently selected from the group consisting of H, hydroxyl, halogen, amino, methyl, and halogenated methyl,
or providing a salt of said m-tyrosine compound and
treating a weed or weed seed with the m-tyrosine compound or the salt of said m-tyrosine compound under conditions effective to inhibit growth of said weed or weed seed in a growth medium, thereby enhancing growth of non-weed plants growing in said growth medium.

22. The method according to claim 21, wherein the m-tyrosine compound has a formula of Formula I, wherein:
$R_4$, $R_5$, $R_6$, $R_7$, $R_8$, and $R_9$ comprise H;
$R_1$ and $R_2$ are independently selected from the group consisting of H, alkyl, alkenyl, alkynyl, and cycloalkyl,
$R_3$ is selected from the group consisting of H, alkyl, alkenyl, alkynyl, alkoxy, and cycloalkyl; and
X is O.

23. The method according to claim 21, wherein the m-tyrosine compound is in isolated form.

24. The method according to claim 21, wherein said providing comprises isolating the m-tyrosine compound from a source plant that produces the m-tyrosine compound.

25. The method according to claim 24, wherein the m-tyrosine compound is isolated from tissue of the source plant, said tissue being selected from the group consisting of root tissue, leaf tissue, shoot tissue, and foliage tissue.

26. The method according to claim 25, wherein said tissue is living tissue or dead tissue.

27. The method according to claim 24, wherein said source plant comprises a *Festuca* species.

28. The method according to claim 27, wherein said *Festuca* species is *Festuca rubra*.

29. The method according to claim 21, wherein said treating comprises applying the compound or the salt of said compound to the surface of the growth medium, prior to emergence of the weed from the growth medium, in an amount sufficient to inhibit growth of the weed or weed seed.

30. The method according to claim 29, wherein the compound or the salt of said compound is applied in granular form or liquid form.

31. The method according to claim 29, wherein the compound or the salt of said compound is applied at a level of about 0.5 to about 12.0 pounds per acre.

32. The method according to claim 21, wherein said treating comprises applying the compound or the salt of said compound to foliage of the weed in an amount sufficient to inhibit growth of the weed.

33. The method according to claim 32, wherein said applying is carried out by spraying the foliage with the compound or the salt of said compound.

34. The method according to claim 32, wherein the compound or the salt of said compound is applied at a level of about 0.5 to about 12.0 pounds per acre.

35. The method according to claim 21, wherein said treating comprises simultaneously applying the compound or the salt of said compound to the growth medium surface and to foliage of the weed in an amount sufficient to inhibit growth of the weed and/or weed seed.

36. The method according to claim 21, wherein said weed or weed seed is selected from the group consisting of a grass weed (monocot weed) and a broadleaf weed (dicot weed).

37. The method according to claim 36, wherein the weed is a grass weed and is selected from the group consisting of crabgrass, barnyardgrass, and annual bluegrass.

38. The method according to claim 36, wherein the weed is a broadleaf weed and is selected from the group consisting of dandelion, white clover, black medic, lettuce, birdsfoot trefoil, common chickweed, common purslane, and curly cress.

39. The method according to claim 21, wherein said non-weed plant is selected from the group consisting of turf grasses, crop plants, and ornamental plants.

40. The method according to claim 39, wherein the non-weed plant is a turf grass and is selected from the group consisting of fine fescue, tall fescue, Kentucky bluegrass, Bermudagrass, bent grass, annual ryegrass, and perennial ryegrass.

41. The method according to claim 39, wherein the non-weed plant is a crop plant and is selected from the group consisting of alfalfa, rice, wheat, barley, rye, cotton, sunflower, peanut, corn, potato, sweet potato, bean, pea, chicory, lettuce, endive, cabbage, brussel sprouts, beet, parsnip, cauliflower, broccoli, turnip, radish, spinach, onion, garlic, eggplant, pepper, celery, carrot, squash, pumpkin, zucchini, cucumber, apple, cherry, peach, pear, melon, citrus, strawberry, grape, raspberry, pineapple, soybean, tobacco, tomato, sorghum, sugarcane, and the like.

42. The method according to claim 39, wherein the non-weed plant is an ornamental plant and is selected from the group consisting of annual bedding plants, perennial bedding plants, herbaceous ornamental plants, and woody ornamental plants.

43. The method according to claim 21, wherein said growth medium is soil.

44. The method according to claim 21 further comprising admixing the compound or the salt of said compound with water, soil, fertilizers, and/or carriers.

* * * * *